(12) United States Patent
Cristau et al.

(10) Patent No.: US 8,524,743 B2
(45) Date of Patent: Sep. 3, 2013

(54) BIS(DIFLUOROMETHYL)PYRAZOLES AS FUNGICIDES

(75) Inventors: Pierre Cristau, Köln (DE); Sebastian Hoffmann, Neuss (DE); Joachim Kluth, Langenfeld (DE); Tomoki Tsuchiya, Düsseldorf (DE); Pierre Wasnaire, Düsseldorf (DE); Jürgen Benting, Leichlingen (DE); Daniela Portz, Vettweiß (DE); Ulrike Wachendorff-Neumann, Neuwied (DE)

(73) Assignee: Bayer Cropscience AG, Monheim (DE)

( * ) Notice: Subject to any disclaimer, the term of this patent is extended or adjusted under 35 U.S.C. 154(b) by 69 days.

(21) Appl. No.: 12/975,150

(22) Filed: Dec. 21, 2010

(65) Prior Publication Data

US 2011/0224257 A1    Sep. 15, 2011

Related U.S. Application Data

(60) Provisional application No. 61/288,484, filed on Dec. 21, 2009.

(30) Foreign Application Priority Data

Dec. 21, 2009  (EP) .................................. 09180073

(51) Int. Cl.
  *A01N 43/78* (2006.01)
  *C07D 417/14* (2006.01)
(52) U.S. Cl.
  USPC ...... 514/326; 514/318; 514/365; 514/217.04; 514/217.1; 514/210.8; 546/209; 546/193; 546/199
(58) Field of Classification Search
  USPC ................ 514/318, 326, 365, 217.04, 217.1, 514/210.18; 546/209, 193, 199
  See application file for complete search history.

(56) References Cited

U.S. PATENT DOCUMENTS

| | | | |
|---|---|---|---|
| 4,245,432 A | 1/1981 | Dannelly | |
| 4,272,417 A | 6/1981 | Barke et al. | |
| 4,808,430 A | 2/1989 | Kouno | |
| 5,876,739 A | 3/1999 | Turnblad et al. | |
| 5,925,645 A | 7/1999 | Schmidt et al. | |
| 7,943,774 B2* | 5/2011 | Cristau et al. ................ | 546/209 |
| 2003/0176428 A1 | 9/2003 | Schneidersmann et al. | |
| 2009/0156592 A1* | 6/2009 | Pasteris et al. ............. | 514/232.8 |
| 2010/0137245 A1 | 6/2010 | Cristau et al. | |
| 2010/0190828 A1 | 7/2010 | Cristau et al. | |
| 2010/0240619 A1* | 9/2010 | Gregory et al. ............... | 514/154 |
| 2010/0286147 A1* | 11/2010 | Hanagan et al. ............ | 514/235.8 |
| 2011/0105429 A1 | 5/2011 | Cristau et al. | |
| 2012/0122929 A1* | 5/2012 | Tsuchiya et al. .............. | 514/326 |

FOREIGN PATENT DOCUMENTS

| | | |
|---|---|---|
| WO | WO 89/10396 A1 | 11/1989 |
| WO | WO 96/33270 A1 | 10/1996 |
| WO | WO 02/28186 A2 | 4/2002 |
| WO | WO 02/080675 A1 | 10/2002 |
| WO | WO 2004/108692 A1 | 12/2004 |
| WO | WO 2005/040159 A1 | 5/2005 |
| WO | WO 2006/133216 A2 | 12/2006 |
| WO | WO 2007/014290 A2 | 2/2007 |
| WO | WO 2007/024782 A2 | 3/2007 |
| WO | WO 2007/027777 A2 | 3/2007 |
| WO | WO 2008/013622 A2 | 1/2008 |
| WO | WO 2008/013925 A4 | 1/2008 |
| WO | WO 2008/091594 A2 | 7/2008 |
| WO | WO 2009/055514 A2 | 4/2009 |
| WO | WO 2005/094445 A2 | 7/2009 |
| WO | WO 2009/094407 A2 | 7/2009 |
| WO | WO 2010/065579 A2 | 6/2010 |
| WO | WO 2010/123791 A1 | 10/2010 |
| WO | WO2012055837 | * 3/2012 |

OTHER PUBLICATIONS

Pasteries et al. "Fungicidal . . . " CA148:185136 (2008).*
Gregory et al. "Heterocyclic compounds . . . " CA150:554518 (2009).*
Hanagan et al. "iSOXAZOLYL-Thiazole . . . " CA151:234956 (2009).*
Cristau et al. "Preparation/\ . . . " CA152:454087 (2010).*
Cristau et al. "Bis(difluoromethyl . . . " CA155:123398 (2011).*
Tsuchiya et al. "Heteroarylpiperidine . . . " CA156:337332 (2012).*
Hillebrand et al. "Heteroarylpiperidine . . . " CA156:588353 (2012).*
Albrecht, B. K., et al., "Discovery and optimization of substituted piperidines as potent, selective, CNS-penetrant α4β2 nicotinic acetycholine receptor potentiators," *Bioorg. Med. Chem. Letters.* 18(2008):5209-5212, Elsevier, Ltd., England (2008).
Brown, D. G., et al., "A Convenient Synthesis of Dimethyl (Diazomethyl)phosphonate (Seyferth/Gilbert Reagent)," *J. Org. Chem.* 61:2540-2541, American Chemical Society, USA (1996).

(Continued)

*Primary Examiner* — Celia Chang
(74) *Attorney, Agent, or Firm* — Sterne, Kessler, Goldstein & Fox P.L.L.C.

(57) ABSTRACT

Bis(difluoromethyl)pyrazole derivatives of the formula (I)

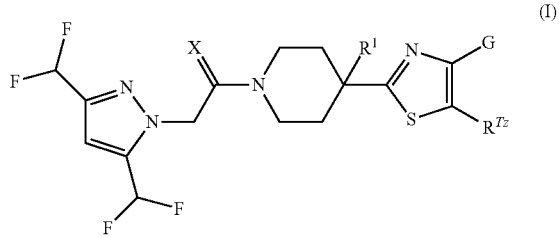

in which the symbols $R^1$, X and G are each as defined in the description, and agrochemically active salts, metal complexes and N-oxides thereof, and use thereof for controlling phytopathogenic harmful fungi, and also processes for preparing compounds of the formula (I).

14 Claims, No Drawings

(56) References Cited

OTHER PUBLICATIONS

Chen, Y.L. et al., "Synthesis and β-lactamase Inhibitory Activity of Thiazolyl Penam Sulfones," *J. Antibio.* 41(1):134-138, Nature Publishing Group, England (Jan. 1988).

Corey, E. J. and Fuchs, P. L., "A synthetic method for formyl-ethynyl conversion (RCHO-R≡CH or RC≡CR')," *Tetrahedron Letters* 36:3769-3772, Pergamon Press, England (1972).

Dondoni, A., et al., "A New Concenient Preparataion of 2-,4-, and 5-Thiazolecarboxaldehydes and Their Conversion into the Corresponding Cabonitrile N-Oxides: Synthesis 3-Thiazolylisoxazoles and 3-Thiazolylisoxazolines," *Synthesis 11*: 998-1001, Thieme Publishing Group, Germany (1987).

Draber, W. and Wegler, R., "Natürliche Pflanzenwurchsstoffe—Phytohormone: 2. Gibberelline," in Chemie der Pflanzenschultz- und Schädlingsbekämpfungsmittel, vol. 2, Wegler, R., ed., pp. 401-412, Springer-Verlag, Germany (1970).

Dvorko, G. F., et al., "Kinetics and Mechanism of Unimolecular Heterolysis of Cage-Like Compounds: XIX,* Effect of the Nucleofuge Nature on the Activation Parameters of Heretolysis of 1-Halo-1-methylcylcohexanes in Cyclohexane. Heterolysis Rate Ratio in Aprotic and Protic Solvents," *Russ. J. of Org. Chem.* 43(1):50-55, Pleiades Publishing Ltd., Russia (2007).

Green, T. W., and Wuts, P. G. M., "Protection from the Amino Group," in *Protective Groups in Organic Chemistry*, 3rd Ed., John Wiley & Sons, USA (1998) pp. 494-653.

Jensen, O. E. and Senning, A., "Studies on Amino Acids and Peptides XII[1] Synthesis of Thiated Analogues of Boc-S-Ala-Aib-S-Ala-OMe and Ac-S-Ala-Aib-S-Ala-OMe," *Tetrahedron* 42(23):655-6564, Pergamon Press, England (1986).

Julia, M. and Paris, J-M., "Syntheses A L'aide de Sulfones V[(+)]—Methode de Synthese Generale de Doubles Liasons," *Tetrahedron Letters* 49:4833-4836, Pergamon Press, England (1973).

Kikelj. D., and Urleb, U., "Synthesis by Substituent Modification," *Science Synthesis 11*(2001) pp. 749-751.

Le Flohic, A., et al., "Reactivity of unsaturated sultones synthesized from unsaturated alcohols by ring-cloning metathesis. Application to the racemic synthesis of the orginally proposed structure of mycothiazole," *Tetrahedron* 62:9017-9037, Elsevier Ltd., USA (2006).

Le Flohic, A., et al., "Total Synthesis of (±)-Mycothiazole and Formal Enantioselective Approach," *Organic Letters* 7(2):339-342, American Chemical Society, USA (2004).

March, J., "Advanced Organic Chemistry-Reactions, Mechanisms and Structures," 4th Ed., John Wiley & Sons, USA (1992) pp. 388-390, 392-400, 406-407, 409, 411-415, 416-419, 430-435,442-443, 496-500, 531-534, 701-703, 910-918, and 1201-1202.

Maryanoff, B. E. and Reitz, A. B., "The Wittig olefination reaction and modifications involving phosphoryl-stabilized carbanions. Stereochemistry, mechanism, and selected synthetic aspects," *Chem. Rev.* 84(4):863-927, American Chemical Society, USA (1989).

Montalbetti, C. A. G. N. and Falque, V., "Amide bond formation and peptide coupling," *Tetrahedron* 61:10827-10852, Tetrahedron Report No. 740, Pergamon Press, England (2005).

Mylari, B. L., et al., "Novel, Potent Aldose Reductase Inhibitors: 3,4-Dihydro-4-oxo-3-[[5-(trifluoromethyl)-2-benzothiazoyl]methyl]-1-phthalazine-acetic Acid (Zopolrestat) and Congeners," *J. Med. Chem.* 34:108-122, American Chemical Society, USA (1991).

Ohmiya, H., et al., "Cobalt-Catalyzed Cross-Coupling Reactions of Alkyl Halides with Allylic and Benzylic Grignard Reagents and Their Applications to Tandem Radical Cyclization/Cross-Coupling Reactions," *Chem. Eur. J.* 10:5640-5648, Wiley-VCH Verlag GmnH & Co. KhaA, Germany (2004).

Peterson, D., "A Carbonyl Olefination Reaction Using Silyl-Substituted Organometallic Compounds," *J. Org. Chem.* 33(2):780-784, American Chemical Society, USA (1968).

Rodrick, R., et al., "Calix[4]arenesulfonylamides. Synthesis, structure and influence on $Mg^{2+}$ ATP-dependent calcium pumps," *Tetrahedron Letters* 46:7459-7462, Elsevier Ltd., USA (2005).

Roth, G.J., et al., "Further Improvements of the Synthesis of Alkynes from Aldehydes," *Synthesis 1*:59-62, Georg Thieme Verlag Stuttgart New York, USA (2004).

Shao, J. and Panek, J. S., "Total Synthesis of Cystothiazoles A and B," *Organic Letters* 6(18):3083-3085, American Chemical Society, USA (2004).

English language translation of Draber, W. and Wegler, R., "Natürliche Pflanzenwuchsstoffe—Phytohormone: 2. Gibberelline," in Chemie der Pflanzenschultz- und Schädlingsbekämpfungsmittel, vol. 2, Wegler, R., ed., pp. 401-412, Springer-Verlag, Germany (1970).

International Search Report for International Application No. PCT/EP2010/070156, European Patent Office, the Netherlands, mailed on Feb. 15, 2011.

* cited by examiner

BIS(DIFLUOROMETHYL)PYRAZOLES AS FUNGICIDES

The invention relates to bis(difluoromethyl)pyrazole derivatives, to agrochemically active salts thereof, to use thereof and to methods and compositions for controlling phytopathogenic harmful fungi in and/or on plants or in and/or on seed of plants, to processes for producing such compositions and treated seed, and to use thereof for controlling phytopathogenic harmful fungi in agriculture, horticulture and forestry, in animal health, in the protection of materials and in the domestic and hygiene sector. The present invention further relates to a process for preparing bis(difluoromethyl)pyrazole derivatives.

It is already known that particular substituted pyrazole derivatives can be used as fungicidal crop protection compositions (see WO 07/014290, WO 08/013925, WO 08/013622, WO 08/091594, WO 08/091580, WO 09/055514, WO 09/094407, WO 09/094445, WO 09/132785, WO 10/037479, WO 10/065579, WO 10/066353, WO 10/123791; see also patent applications with application numbers: DE102010000662.9, PCT/EP2010/003499, EP09174510.9, EP09174614.9; EP09180073.0, EP10161264.6, EP10163067.1, EP10164099.3, EP10172486.2, EP10174012.4, EP10189067.1). However, specifically at relatively low application rates, the fungicidal activity of these compounds is not always sufficient.

Since the ecological and economic demands made on modern crop protection compositions are increasing constantly, for example with respect to activity spectrum, toxicity, selectivity, application rate, formation of residues and favourable manufacture, and problems with resistances, for example, can also occur, there is a constant need to develop novel crop protection compositions, especially fungicides, which, at least in some areas, have advantages over the known ones.

It has now been found that, surprisingly, the present bis(difluoromethyl)pyrazole derivatives achieve at least some aspects of the objects mentioned and are suitable for use as crop protection compositions, especially as fungicides.

The invention relates to compounds of the formula (I)

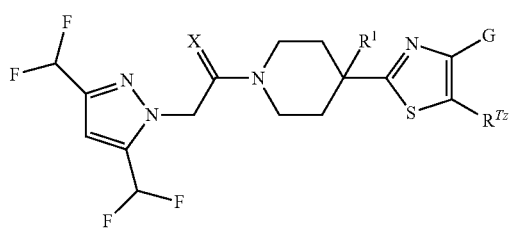

(I)

in which the symbols are each defined as follows:
X is oxygen or sulphur,
G is

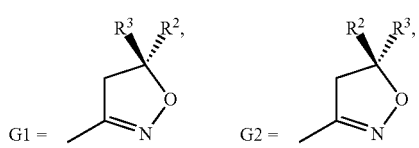

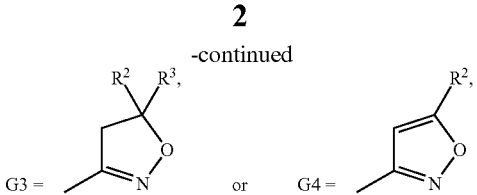

$R^1$ is hydrogen or halogen.
$R^2$ is $C_1$-$C_6$-alkyl or $C_1$-$C_6$-haloalkyl,
or
$R^2$ is a $C_3$-$C_8$-cycloalkyl which may contain up to two substituents, where the substituents are each independently selected from the following list:
cyano, halogen, hydroxyl, oxo, $C_1$-$C_4$-haloalkyl, $C_1$-$C_4$-haloalkoxy, $C_1$-$C_4$-alkoxy, $C_1$-$C_4$-haloalkoxy, $C_1$-$C_4$-alkylthio, $C_1$-$C_4$-haloalkylthio or phenyl,
or
$R^2$ is a $C_5$-$C_8$-cycloalkenyl which may contain up to two substituents, where the substituents are each independently selected from the following list:
cyano, halogen, hydroxyl, oxo, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio or phenyl,
or
$R^2$ is a phenyl which may contain up to two substituents, where the substituents are each independently selected from the following list:
amino, halogen, cyano, hydroxyl, SH, nitro, C(=O)H, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_4$-$C_{10}$-alkylcycloalkyl, $C_4$-$C_{10}$-cycloalkylalkyl, $C_6$-$C_{14}$-cycloalkylcycloalkyl, $C_4$-$C_{10}$-halocycloalkylalkyl, $C_5$-$C_{10}$-alkylcycloalkylalkyl, $C_3$-$C_8$-cycloalkenyl, $C_3$-$C_8$-halocycloalkenyl, $C_2$-$C_6$-alkoxyalkyl, $C_4$-$C_{10}$-cycloalkoxyalkyl, $C_3$-$C_8$-alkoxyalkoxyalkyl, $C_2$-$C_6$-alkylthioalkyl, $C_2$-$C_6$-alkylsulphinylalkyl, $C_2$-$C_6$-alkylsulphonylalkyl, $C_2$-$C_6$-alkylaminoalkyl, $C_3$-$C_8$-dialkylaminoalkyl, $C_2$-$C_6$-haloalkylaminoalkyl, $C_4$-$C_{10}$-cycloalkylaminoalkyl, $C_2$-$C_6$-alkylcarbonyl, $C_2$-$C_6$-haloalkylcarbonyl, $C_4$-$C_8$-cycloalkylcarbonyl, $C_2$-$C_6$-alkoxycarbonyl, $C_4$-$C_8$-cycloalkoxycarbonyl, $C_5$-$C_{10}$-cycloalkylalkoxycarbonyl, $C_2$-$C_6$-alkylaminocarbonyl, $C_3$-$C_8$-dialkylaminocarbonyl, $C_4$-$C_8$-cycloalkylaminocarbonyl, $C_2$-$C_6$-haloalkoxyalkyl, $C_1$-$C_6$-hydroxyalkyl, $C_1$-$C_6$-alkoxy, $C_1$-$C_6$-haloalkoxy, $C_3$-$C_8$-cycloalkoxy, $C_3$-$C_8$-halocycloalkoxy, $C_4$-$C_{10}$-cycloalkylalkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_2$-$C_6$-alkoxyalkoxy, $C_2$-$C_6$-alkylcarbonyloxy, $C_2$-$C_6$-haloalkylcarbonyloxy, $C_4$-$C_8$-cycloalkylcarbonyloxy, $C_3$-$C_6$-alkylcarbonylalkoxy, $C_1$-$C_6$-alkylthio, $C_1$-$C_6$-haloalkylthio, $C_3$-$C_6$-cycloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_3$-$C_8$-cycloalkylsulphonyl, tri($C_1$-$C_4$-alkyl)silyl, $C_1$-$C_6$-alkylsulphonylamino, $C_1$-$C_6$-haloalkylsulphonylamino or -LQ,
or
$R^2$ is naphthyl, dihydronaphthalenyl, tetrahydronaphthalenyl, hexahydronaphthalenyl, octahydronaphthalenyl or indenyl which may contain up to two substituents, where the substituents are each independently selected from the following list:
cyano, nitro, halogen, $C_1$-$C_6$-alkyl, $C_1$-$C_4$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_4$-alkyl)silyl, benzyl, phenyl, hydroxyl, SH, oxo, $C_1$-$C_6$-alkoxy, $C_1$-$C_6$-haloalkoxy, $C_2$-$C_6$-alkenyloxy, $C_2$-$C_6$-alkynyloxy, $C_1$-$C_6$-alkylthio or $C_1$-$C_6$-haloalkylthio, or $R^2$ is a 5- or 6-membered heteroaryl radical which may contain up to two substituents, where the substituents are each independently selected from the following list:

substituents on carbon: halogen, cyano, nitro, hydroxyl, SH, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_6$-$C_{14}$-cycloalkylcycloalkyl, $C_5$-$C_{10}$-alkylcycloalkylalkyl, $C_2$-$C_4$-alkoxyalkyl, $C_2$-$C_4$-alkylcarbonyl, $C_2$-$C_6$-alkoxycarbonyl, $C_2$-$C_6$-alkylaminocarbonyl, $C_3$-$C_8$-dialkylaminocarbonyl, $C_1$-$C_4$-hydroxyalkyl, $C_1$-$C_4$-alkoxy, $C_1$-$C_4$-haloalkoxy, $C_2$-$C_6$-alkylcarbonyloxy, $C_2$-$C_6$-alkylcarbonylthio, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, tri($C_1$-$C_4$-alkyl)silyl or -LQ, substituents on nitrogen: $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_1$-$C_4$-alkylsulphonyl, C(=O)H, C(=O)Me, C(=O)OMe, benzyl or phenyl, or $R^2$ and $R^3$, together with the carbon atom to which they are bonded, form a 5- to 12-membered unsubstituted or substituted, partly saturated or unsaturated, mono- or bicyclic ring system which may contain up to three further heteroatoms selected from N, O and S, where no two oxygen atoms are adjacent and where any possible substituents are selected independently from halogen, $C_1$-$C_4$-alkyl, $C_1$-$C_4$-haloalkyl, $C_1$-$C_4$-alkoxy, $C_1$-$C_4$-haloalkoxy, oxo, hydroxyl, benzyl and phenyl, $R^3$ is hydrogen, cyano, $C_1$-$C_3$-alkyl or $C_1$-$C_3$-haloalkyl, $R^{Tz}$ is halogen or hydrogen L is a direct bond, —CH$_2$—, —(C=O)—, sulphur or oxygen, Q is a phenyl which may contain up to two substituents, where the substituents are each independently selected from the following list:

halogen, cyano, nitro, hydroxyl, SH, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_2$-$C_6$-alkoxyalkyl, $C_2$-$C_6$-alkylcarbonyl, $C_2$-$C_6$-haloalkylcarbonyl, $C_2$-$C_6$-alkoxycarbonyl, $C_1$-$C_6$-alkoxy, $C_1$-$C_6$-haloalkoxy, $C_3$-$C_8$-cycloalkoxy, $C_3$-$C_8$-halocycloalkoxy, $C_2$-$C_6$-alkenyloxy, $C_2$-$C_6$-alkynyloxy, $C_2$-$C_6$-alkoxyalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, tri($C_1$-$C_4$-alkyl)silyl or phenyl, or Q is a 5- or 6-membered heteroaryl radical which may contain up to two substituents, where the substituents are each independently selected from the following list:

substituents on carbon: halogen, cyano, nitro, hydroxyl, SH, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_6$-$C_{14}$-cycloalkylcycloalkyl, $C_5$-$C_{10}$-alkylcycloalkylalkyl, $C_2$-$C_4$-alkoxyalkyl, $C_2$-$C_4$-alkylcarbonyl, $C_2$-$C_6$-alkoxycarbonyl, $C_1$-$C_4$-alkoxy, $C_1$-$C_4$-haloalkoxy, $C_2$-$C_6$-alkylcarbonyloxy, $C_2$-$C_6$-alkylcarbonylthio, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, tri($C_1$-$C_4$-alkyl)silyl or phenyl, substituents on nitrogen: $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_4$-haloalkynyl, $C_3$-$C_6$-cycloalkyl, $C_1$-$C_4$-alkylsulphonyl, C(=O)H, C(=O)Me, C(=O)OMe or phenyl, and agrochemically active salts, metal complexes and N-oxides thereof.

The invention further provides for the use of the compounds of the formula (I) as a fungicide.

Inventive bis(difluoromethyl)pyrazole derivatives of the formula (I) and the agrochemically active salts, metal complexes and N-oxides thereof are very suitable for controlling phytopathogenic harmful fungi. The aforementioned inventive compounds exhibit potent fungicidal activity in particular, and can be used in crop protection, in the domestic and hygiene sector, and in the protection of materials.

The compounds of the formula (I) may be present either in pure form or as mixtures of different possible isomeric forms, especially of stereoisomers, such as E and Z, threo and erythro, and also optical isomers, such as R and S isomers or atropisomers, and, if appropriate, also of tautomers. Both the E and the Z isomers are claimed, as are the threo and erythro isomers, and also the optical isomers, all possible mixtures of these isomers, and also the possible tautomeric forms.

The bis(difluoromethyl)pyrazole derivatives usable in accordance with the invention are defined in general terms by the formula (I). Preferred radical definitions for the above formula shown and those specified below are specified hereinafter. These definitions apply equally to the end products of the formula (I) and to all intermediates (see also below under "Illustrations of the processes and intermediates").

X is preferably oxygen, $R^1$ is preferably hydrogen or fluorine,

G is preferably G1, G3 and G4,

G is more preferably

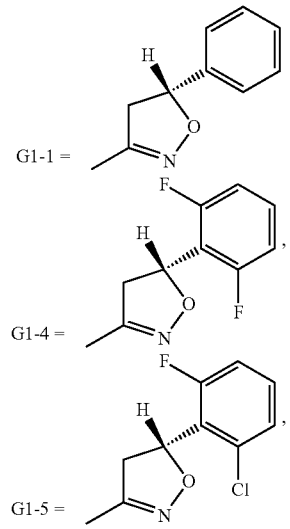

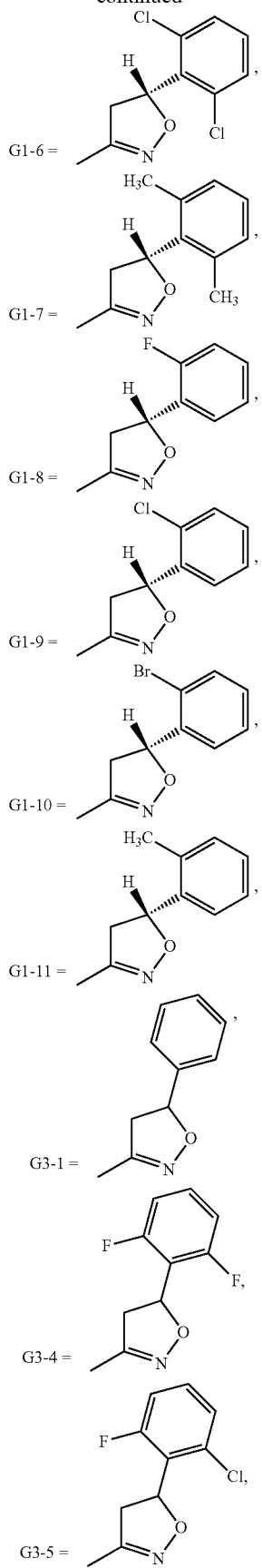
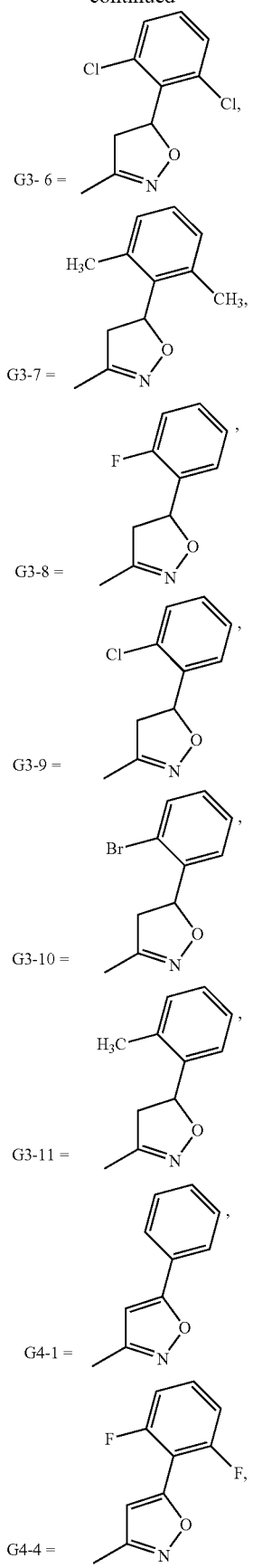

-continued

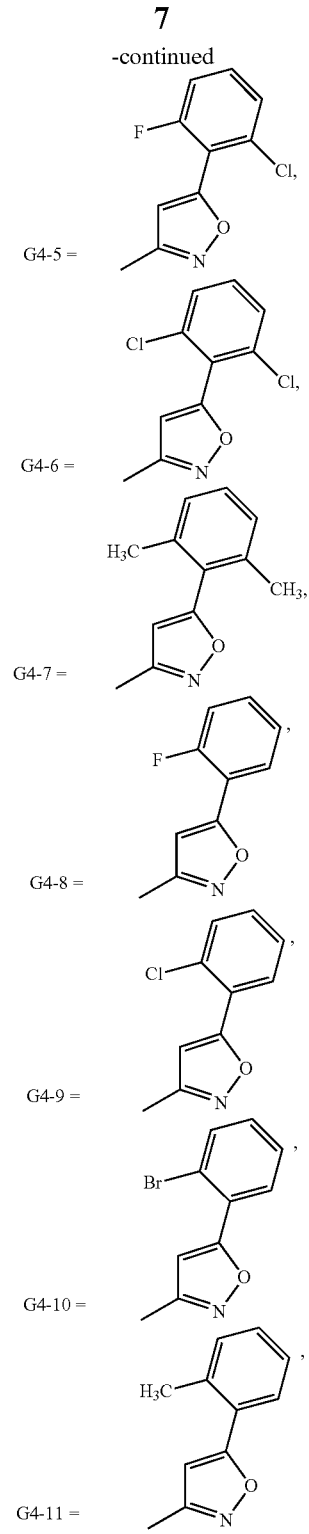

G4-5 =

G4-6 =

G4-7 =

G4-8 =

G4-9 =

G4-10 =

G4-11 =

$R^2$ is preferably a $C_3$-$C_8$-cycloalkyl which may contain up to two substituents, where the substituents are each independently selected from the following list:
cyano, halogen, hydroxyl, oxo, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio or phenyl, $R^2$ is also preferably a phenyl which may contain up to two substituents, where the substituents are each independently selected from the following list:
amino, halogen, cyano, hydroxyl, SH, nitro, C(=O)H, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_4$-$C_{10}$-alkylcycloalkyl, $C_4$-$C_{10}$-cycloalkylalkyl, $C_6$-$C_{14}$-cycloalkylcycloalkyl, $C_4$-$C_{10}$-halocycloalkylalkyl, $C_5$-$C_{10}$-alkylcycloalkylalkyl, $C_3$-$C_8$-cycloalkenyl, $C_3$-$C_8$-halocycloalkenyl, $C_2$-$C_6$-alkoxyalkyl, $C_4$-$C_{10}$-cycloalkoxyalkyl, $C_3$-$C_8$-alkoxyalkoxyalkyl, $C_2$-$C_6$-alkylthioalkyl, $C_2$-$C_6$-alkylsulphinylalkyl, $C_2$-$C_6$-alkylsulphonylalkyl, $C_2$-$C_6$-alkylaminoalkyl, $C_3$-$C_8$-dialkylaminoalkyl, $C_2$-$C_6$-haloalkylaminoalkyl, $C_4$-$C_{10}$-cycloalkylaminoalkyl, $C_2$-$C_6$-alkylcarbonyl, $C_2$-$C_6$-haloalkylcarbonyl, $C_4$-$C_8$-cycloalkylcarbonyl, $C_2$-$C_6$-alkoxycarbonyl, $C_4$-$C_8$-cycloalkoxycarbonyl, $C_5$-$C_{10}$-cycloalkylalkoxycarbonyl, $C_2$-$C_6$-alkylaminocarbonyl, $C_3$-$C_8$-dialkylaminocarbonyl, $C_4$-$C_8$-cycloalkylaminocarbonyl, $C_2$-$C_6$-haloalkoxyalkyl, $C_1$-$C_6$-hydroxyalkyl, $C_1$-$C_6$-alkoxy, $C_1$-$C_6$-haloalkoxy, $C_3$-$C_8$-cycloalkoxy, $C_3$-$C_8$-halocycloalkoxy, $C_4$-$C_{10}$-cycloalkylalkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_2$-$C_6$-alkoxyalkoxy, $C_2$-$C_6$-alkylcarbonyloxy, $C_2$-$C_6$-haloalkylcarbonyloxy, $C_4$-$C_8$-cycloalkylcarbonyloxy, $C_3$-$C_6$-alkylcarbonylalkoxy, $C_1$-$C_6$-alkylthio, $C_1$-$C_6$-haloalkylthio, $C_3$-$C_6$-cycloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_3$-$C_8$-cycloalkylsulphonyl, tri($C_1$-$C_4$-alkyl)silyl, $C_1$-$C_6$-alkylsulphonylamino, $C_1$-$C_6$-haloalkylsulphonylamino or -LQ.

$R^2$ is also preferably a 5- or 6-membered heteroaryl radical which may contain up to two substituents, where the substituents are each independently selected from the following list:
substituents on carbon: halogen, cyano, nitro, hydroxyl, SH, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_6$-$C_{14}$-cycloalkylcycloalkyl, $C_5$-$C_{10}$-alkylcycloalkylalkyl, $C_2$-$C_4$-alkoxyalkyl, $C_2$-$C_4$-alkylcarbonyl, $C_2$-$C_6$-alkoxycarbonyl, $C_2$-$C_6$-alkylaminocarbonyl, $C_3$-$C_8$-dialkylaminocarbonyl, $C_1$-$C_4$-hydroxyalkyl, $C_1$-$C_4$-alkoxy, $C_1$-$C_4$-haloalkoxy, $C_2$-$C_6$-alkylcarbonyloxy, $C_2$-$C_6$-alkylcarbonylthio, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, tri($C_1$-$C_4$-alkyl)silyl or -LQ,
substituents on nitrogen: $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_1$-$C_4$-alkylsulphonyl, C(=O)H, C(=O)Me, C(=O)OMe, benzyl or phenyl, $R^2$ is more preferably a phenyl which may contain up to two substituents, where the substituents are each independently selected from the following list:
amino, halogen, cyano, nitro, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_2$-$C_6$-alkoxyalkyl, $C_2$-$C_6$-alkylcarbonyl, $C_2$-$C_6$-haloalkylcarbonyl, $C_2$-$C_6$-alkoxycarbonyl, $C_1$-$C_6$-alkoxy, $C_1$-$C_6$-haloalkoxy, $C_3$-$C_8$-cycloalkoxy, $C_3$-$C_8$-halocycloalkoxy, $C_2$-$C_6$-alkenyloxy, $C_2$-$C_6$-alkynyloxy, $C_2$-$C_6$-alkoxyalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, or phenyl, $R^2$ is even more preferably a phenyl which may contain up to two substituents, where the substituents are each independently selected from the following list:

chlorine, fluorine, bromine, iodine, cyano, nitro, —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)CH_3$, —$C(CH_3)_3$, —$CH$=$CH_2$, —$CH$=$CHCH_3$, —$CH_2CH$=$CH_2$, —$CH$=$CHCH_2CH_3$, —$CH_2CH$=$CHCH_3$, —$CH_2CH_2CH$=$CH_2$, —$C$≡$CH$, —$C$≡$CCH_3$, —$CH_2C$≡$CH$, —$C$≡$CCH_2CH_3$, —$CH_2C$≡$CCH_3$, —$CH_2CH_2C$≡$CH$, —$CF_3$, —$CFH_2$, —$CF_2H$, —$CF_2CF_3$, —$CCl_3$, cyclopropyl, cyclobutyl, cyclopentyl, cyclohexyl, —$CH_2OCH_3$, —$CH_2OCH_2CH_3$, —$CH_2CH_2OCH_3$, —$CH_2OCH_2CH_2CH_3$, —$CH_2CH_2OCH_2CH_3$, —$CH_2CH_2CH_2OCH_3$, —$C(=O)CH_3$, —$C(=O)CH_2CH_3$, —$C(=O)CH_2CH_2CH_3$, —$C(=O)CH(CH_3)_2$, —$C(=O)CF_3$, —$C(=O)OCH_3$, —$C(=O)OCH_2CH_3$, —$C(=O)OCH_2CH_2CH_3$, —$C(=O)OCH(CH_3)_2$, —$OCH_3$, —$OCH_2CH_3$, —$OCH_2CH_2CH_3$, —$OCH(CH_3)_2$, —$OCH_2CH_2CH_2CH_3$, —$OCH_2CH(CH_3)_2$, —$OCH(CH_3)CH_2CH_3$, —$OC(CH_3)_3$, —$OCF_3$, —$OCF_2H$, —$OCH_2CF_3$, —$OCF_2CF_3$, O-cyclohexyl, O-cyclopentyl, O-cyclopropyl, —$SCH_3$, —$SCH_2CH_3$, —$SCH_2CH_2CH_3$, —$SCH(CH_3)_2$, —$SCH_2CH_2CH_2CH_3$, —$SCH_2CH(CH_3)_2$, —$SCH(CH_3)CH_2CH_3$, —$SC(CH_3)_3$, —$SCF_3$, —$SCF_2H$, —$SCH_2CF_3$, —$SCF_2CF_3$, —$S(=O)Me$, —$S(O)CF_3$, —$S(=O)_2Me$, —$S(O)_2CF_3$, —$OCH_2CH$=$CH_2$, —$OCH_2C$≡$CH$, —$OCH_2OCH_3$, —$OCH_2OCH_2CH_3$, —$OCH_2CH_2OCH_3$, —$OCH_2OCH(CH_3)_2$, trimethylsilyl or phenyl, $R^2$ is especially preferably a phenyl which may contain up to two substituents, where the substituents are each independently selected from the following list:

fluorine, chlorine, bromine, —$CH_3$ or phenyl, $R^3$ is preferably hydrogen, cyano or $C_1$-$C_3$-alkyl, $R^3$ is more preferably hydrogen or methyl, ethyl, n-propyl, isopropyl, $R^3$ is even more preferably hydrogen, $R^{Tz}$ is preferably chlorine or hydrogen and more preferably hydrogen, L is preferably a direct bond or oxygen, Q is preferably a phenyl which may contain up to two substituents, where the substituents are each independently selected from the following list:

halogen, cyano, hydroxyl, nitro, SH, $C_1$-$C_6$-alkyl, $C_1$-$C_6$-haloalkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-haloalkylthio or phenyl, Q is also preferably a 5- or 6-membered heteroaryl radical which may contain up to two substituents, where the substituents are each independently selected from the following list:

substituents on carbon:
halogen, cyano, hydroxyl, nitro, SH, $C_1$-$C_6$-alkyl, $C_1$-$C_6$-haloalkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-haloalkylthio or phenyl, substituents on nitrogen: $C_1$-$C_6$-alkyl, $C_2$-$C_6$-alkenyl, $C_2$-$C_6$-alkynyl, $C_3$-$C_6$-cycloalkyl or phenyl, and agrochemically active salts, metal complexes and N-oxides thereof.

The radical definitions and explanations given above in general terms or stated within preferred ranges can, however, also be combined with one another as desired, i.e. including between the particular ranges and preferred ranges. They apply both to the end products and correspondingly to precursors and intermediates. Moreover, individual definitions may not apply.

Preference is given to compounds of the formula (I) in which all radicals in each case have the preferred definitions mentioned above.

Particular preference is given to compounds of the formula (I) in which all radicals in each case have the more preferred definitions mentioned above.

Very particular preference is given to compounds of the formula (I) in which all radicals in each case have the even more preferred definitions mentioned above.

Special preference is given to compounds of the formula (I) in which all radicals in each case have the especially preferred definitions mentioned above.

Preference is further given to compounds of the formula (I) in which

X is oxygen.

G is G3 and/or G4 and is especially G3, $R^1$ is fluorine or hydrogen and is especially hydrogen, $R^2$ is phenyl, 2-fluorophenyl, 2,6-difluorophenyl, 2-acetylphenyl, 3-acetylphenyl, 2-hydroxy-phenyl, 2-nitrophenyl, 2-[(2-methoxyethoxy)methyl]phenyl, 2-[(ethyl-sulphanyl)methyl]phenyl, 2-[(cyclopropylmethoxy)carbonyl]phenyl, 2-(allyloxy)phenyl, 3-(but-2-yn-1-yloxy)phenyl, 2-(butoxymethyl)phenyl, 2-fluoro-6-formylphenyl, 2-[(2-methylprop-2-en-1-yl)oxy]phenyl, 2-(2-methoxyethoxy)phenyl, 2-[(3-methylbut-2-en-1-yl)oxy]phenyl, 3-(prop-2-yn-1-yloxy)phenyl, 4-(prop-2-yn-1-yloxy)phenyl, 3-formylphenyl, 2-(cyclohexylmethoxy)phenyl, 2-(pent-2-yn-1-yloxy)phenyl, 2-formylphenyl, 2-(cyclopropylcarbamoyl)phenyl, 2-(but-2-yn-1-yloxy)-6-fluorophenyl, 2-fluoro-6-(prop-2-yn-1-yloxy)phenyl, 2-[(cyclohexylcarbonyl)oxy]phenyl, 2-[(cyclopropyl-carbonyl)oxy]phenyl, 3-(pent-2-yn-1-yloxy)phenyl, 2-(but-2-yn-1-yloxy)phenyl, 2-[(3,3,3-trifluoropropanoyl)oxy]phenyl, 2-[(methylsulphonyl)amino]phenyl, 2-ethynylphenyl, 2-(prop-2-yn-1-yloxy)phenyl, 4-[(methylsulphonyl)amino]phenyl, 2-aminophenyl, 3-hydroxyphenyl, 2-(methoxycarbonyl)phenyl, 2-(chloromethyl)phenyl, 4-(pent-2-yn-1-yloxy)phenyl, 4-(but-2-yn-1-yloxy)phenyl, 2-chloro-6-(prop-2-yn-1-yloxy)phenyl, 2-chloro-6-(2-methoxyethoxy)phenyl, 2-(allyloxy)-6-chlorophenyl, 2-[(2,2,2-trifluoroethoxy)methyl]phenyl, 2-[(ethylsulphonyl)methyl]phenyl or 2-(hydroxymethyl)phenyl, and $R^2$ is especially phenyl, 2-fluorophenyl or 2,6-difluorophenyl, $R^3$ is hydrogen, $R^{Tz}$ is hydrogen.

and agrochemically active salts, metal complexes and N-oxides thereof.

According to the type of substituents defined above, the compounds of the formula (I) have acidic or basic properties and can form salts, if appropriate also internal salts or adducts, with inorganic or organic acids or with bases or with metal ions. If the compounds of the formula (I) bear amino, alkylamino or other groups which induce basic properties, these compounds can be reacted with acids to give salts, or they are obtained directly as salts in the synthesis. If the compounds of the formula (I) bear hydroxyl, carboxyl or other groups which induce acidic properties, these compounds can be reacted with bases to give salts. Suitable bases are, for example, hydroxides, carbonates, hydrogencarbonates of the alkali metals and alkaline earth metals, especially those of sodium, potassium, magnesium and calcium, and also ammonia, primary, secondary and tertiary amines having $C_1$-$C_4$-alkyl groups, mono-, di- and trialkanolamines of $C_1$-$C_4$-alkanols, choline and chlorocholine.

The salts obtainable in this way likewise have fungicidal, herbicidal and insecticidal properties.

Examples of inorganic acids are hydrohalic acids, such as hydrogen fluoride, hydrogen chloride, hydrogen bromide and hydrogen iodide, sulphuric acid, phosphoric acid and nitric acid, and acidic salts such as $NaHSO_4$ and $KHSO_4$. Useful organic acids are, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, saturated or mono- or diunsaturated $C_6$-$C_{20}$ fatty acids, alkylsulphuric monoesters, alkylsulphonic acids (sulphonic acids having straight-chain or branched alkyl radicals having 1 to 20 carbon atoms), arylsulphonic acids or aryldisulphonic acids (aromatic radicals, such as phenyl and naphthyl, which bear one or two sulphonic acid groups), alkylphosphonic acids (phosphonic acids having straight-chain or branched alkyl radicals having 1 to 20 carbon atoms), arylphosphonic acids or aryldiphosphonic acids (aromatic radicals, such as phenyl and naphthyl, which bear one or two phosphonic acid radicals), where the alkyl and aryl radicals may bear further substituents, for example p-toluenesulphonic acid, salicylic acid, p-aminosalicylic acid, 2-phenoxybenzoic acid, 2-acetoxybenzoic acid, etc.

Useful metal ions are especially the ions of the elements of the second main group, especially calcium and magnesium, of the third and fourth main groups, especially aluminium, tin and lead, and also of the first to eighth transition groups, especially chromium, manganese, iron, cobalt, nickel, copper, zinc and others. Particular preference is given to the metal ions of the elements of the fourth period. These metals may be present in the different valencies that they can assume.

Optionally substituted groups may be mono- or polysubstituted, where the substituents in the case of polysubstitutions may be the same or different.

In the definitions of the symbols given in the formulae above, collective terms were used which are generally representative of the following substituents:

halogen: fluorine, chlorine, bromine and iodine;

alkyl: saturated, straight-chain or branched hydrocarbon radicals having 1 to 8 carbon atoms, for example (but not limited to) $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

alkenyl: unsaturated, straight-chain or branched hydrocarbon radicals having 2 to 8 carbon atoms and one double bond in any position, for example (but not limited to) $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl 1,1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkynyl: straight-chain or branched hydrocarbon groups having 2 to 8 carbon atoms and one triple bond in any position, for example (but not limited to) $C_2$-$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

alkoxy: saturated, straight-chain or branched alkoxy radicals having 1 to 8 carbon atoms, for example (but not limited to) $C_1$-$C_6$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethyl butoxy, 1,1,2-trimethylpropoxy, 1,2,2-trimethylpropoxy, 1-ethyl-1-methylpropoxy and 1-ethyl-2-methylpropoxy;

alkylthio: saturated, straight-chain or branched alkylthio radicals having 1 to 8 carbon atoms, for example (but not limited to) $C_1$-$C_6$-alkylthio such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

alkoxycarbonyl: an alkoxy group which has 1 to 6 carbon atoms (as specified above) and is bonded to the skeleton via a carbonyl group (—CO—);

alkylsulphinyl: saturated, straight-chain or branched alkylsulphinyl radicals having 1 to 8 carbon atoms, for example (but not limited to) $C_1$-$C_6$-alkylsulphinyl such as methylsulphinyl, ethylsulphinyl, propylsulphinyl, 1-methylethylsulphinyl, butylsulphinyl, 1-methylpropylsulphinyl, 2-methylpropylsulphinyl, 1,1-dimethylethylsulphinyl, pentylsulphinyl, 1-methylbutylsulphinyl, 2-methylbutylsulphinyl, 3-methylbutylsulphinyl, 2,2-dimethylpropylsulphinyl, 1-ethylpropylsulphinyl, hexylsulphinyl, 1,1-dimethylpropylsulphinyl, 1,2-dimethylpropylsulphinyl, 1-methylpentylsulphinyl, 2-methylpentylsulphinyl, 3-methylpentylsulphinyl, 4-methylpentylsulphinyl, 1,1-dimethylbutylsulphinyl, 1,2-dimethylbutylsulphinyl, 1,3-dimethylbutylsulphinyl, 2,2-dimethylbutylsulphinyl, 2,3-dimethylbutylsulphinyl, 3,3-dimethylbutylsulphinyl, 1-ethylbutylsulphinyl, 2-ethylbutylsulphinyl, 1,1,2-trimethylpropylsulphinyl, 1,2,2-trimethylpropylsulphinyl, 1-ethyl-1-methylpropylsulphinyl and 1-ethyl-2-methylpropylsulphinyl;

alkylsulphonyl: saturated, straight-chain or branched alkylsulphonyl radicals having 1 to 8 carbon atoms, for example (but not limited to) $C_1$-$C_6$-alkylsulphonyl such as methylsulphonyl, ethylsulphonyl, propylsulphonyl, 1-methylethylsulphonyl, butylsulphonyl, 1-methylpropylsulphonyl, 2-methylpropylsulphonyl, 1,1-dimethylethylsulphonyl, pentylsulphonyl, 1-methylbutylsulphonyl, 2-methylbutylsulphonyl, 3-methylbutylsulphonyl, 2,2-dimethylpropylsulphonyl, 1-ethylpropylsulphonyl, hexylsulphonyl, 1,1-dimethylpropylsulphonyl, 1,2-dimethylpropylsulphonyl, 1-methylpentylsulphonyl, 2-methylpentylsulphonyl, 3-methylpentylsulphonyl, 4-methylpentylsulphonyl, 1,1-dimethylbutylsulphonyl, 1,2-dimethylbutylsulphonyl, 1,3-dimethylbutylsulphonyl, 2,2-dimethylbutylsulphonyl, 2,3-dimethylbutylsulphonyl, 3,3-dimethylbutylsulphonyl, 1-ethylbutylsulphonyl, 2-ethylbutylsulphonyl, 1,1,2-trimethylpropylsulphonyl, 1,2,2-trimethylpropylsulphonyl, 1-ethyl-1-methylpropylsulphonyl and 1-ethyl-2-methylpropylsulphonyl;

cycloalkyl: monocyclic, saturated hydrocarbon groups having 3 to 10 carbon ring members, for example (but not limited to) cyclopropyl, cyclopentyl and cyclohexyl;

haloalkyl: straight-chain or branched alkyl groups having 1 to 8 carbon atoms (as specified above), where some or all of the hydrogen atoms in these groups may be replaced by halogen atoms as specified above, for example (but not limited to) $C_1$-$C_4$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl;

haloalkoxy: straight-chain or branched alkoxy groups having 1 to 8 carbon atoms (as specified above), where some or all of the hydrogen atoms in these groups may be replaced by halogen atoms as specified above, for example (but not limited to) $C_1$-$C_3$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy;

haloalkylthio: straight-chain or branched alkylthio groups having 1 to 8 carbon atoms (as specified above), where some or all of the hydrogen atoms in these groups may be replaced by halogen atoms as specified above, for example (but not limited to) $C_1$-$C_3$-haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, pentafluoroethylthio and 1,1,1-trifluoroprop-2-ylthio;

heteroaryl: 5 or 6-membered fully unsaturated monocyclic ring system containing one to four heteroatoms from the group of oxygen, nitrogen and sulphur; if the ring contains two or more oxygen atoms, they are not directly adjacent;

5-membered heteroaryl: containing one to four nitrogen atoms or one to three nitrogen atoms and one sulphur or oxygen atom: 5-membered heteroaryl groups which, in addition to carbon atoms, may contain one to four nitrogen atoms or one to three nitrogen atoms and one sulphur or oxygen atom as ring members, for example (but not limited to) 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

5-membered heteroaryl which contains one to four nitrogen atoms and is attached via nitrogen, or benzofused 5-membered heteroaryl which contains one to three nitrogen atoms and is attached via nitrogen: 5-membered heteroaryl groups which, in addition to carbon atoms, may contain one to four nitrogen atoms or one to three nitrogen atoms as ring members, and in which two adjacent carbon ring members or one nitrogen and one adjacent carbon ring member may be bridged by a buta-1,3-diene-1,4-diyl group in which one or two carbon atoms may be replaced by nitrogen atoms, where these rings are bonded to the skeleton via one of the nitrogen ring members, for example (but not limited to) 1-pyrrolyl, 1-pyrazolyl, 1,2,4-triazol-1-yl, 1-imidazolyl, 1,2,3-triazol-1-yl and 1,3,4-triazol-1-yl;

6-membered heteroaryl containing one to four nitrogen atoms: 6-membered heteroaryl groups which, in addition to carbon atoms, may contain one to three or one to four nitrogen atoms as ring members, for example (but not limited to) 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzofused 5-membered heteroaryl which contains one to three nitrogen atoms or one nitrogen atom and one oxygen or sulphur atom: for example (but not limited to) indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl and 1,3-benzoxazol-7-yl;

benzofused 6-membered heteroaryl containing one to three nitrogen atoms: for example (but not limited to) quinolin-2-yl, quinolin-3-yl, quinolin-4-yl, quinolin-5-yl, quinolin-6-yl, quinolin-8-yl, isoquinolin-1-yl, isoquinolin-3-yl, isoquinolin-4-yl, isoquinolin-5-yl, isoquinolin-6-yl, isoquinolin-7-yl and isoquinolin-8-yl;

heterocyclyl: a three- to fifteen-membered saturated or partially unsaturated heterocycle containing one to four heteroatoms from the group of oxygen, nitrogen and sulphur: mono-, bi- or tricyclic heterocycles which contain, in addition to carbon ring members, one to three nitrogen atoms and/or one oxygen or sulphur atom or one or two oxygen and/or sulphur atoms; if the ring contains two or more oxygen atoms, they are not directly adjacent; for example (but not limited to) oxiranyl, aziridinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl;

leaving group: $S_N1$ or $S_N2$ leaving group, for example chlorine, bromine, iodine, alkylsulphonates (—$OSO_2$-alkyl, e.g. —$OSO_2CH_3$, —$OSO_2CF_3$) or arylsulphonates (—$OSO_2$-aryl, e.g. —$OSO_2Ph$, —$OSO_2PhMe$).

In the naming of combinations of a plurality of radicals, for example Cx-Cy-alkylcarbonyl or Cx-Cy-alkoxyalkyl, the expression Cx-Cy in each case denotes the sum total of all carbon atoms present in the overall fragment in each case. X and Y are each whole numbers, where the number Y is greater than the number X.

Not included are combinations which contravene natural laws and which the person skilled in the art would therefore exclude based on his/her expert knowledge. Ring structures having three or more adjacent oxygen atoms, for example, are excluded.

Illustration of the Processes and Intermediates

The bis(difluoromethyl)pyrazole derivatives of the formula (I) can be prepared in different ways. First of all, the possible processes are shown schematically hereinafter. Unless stated otherwise, the radicals stated are each as defined above.

Process A

Scheme 1: Process A

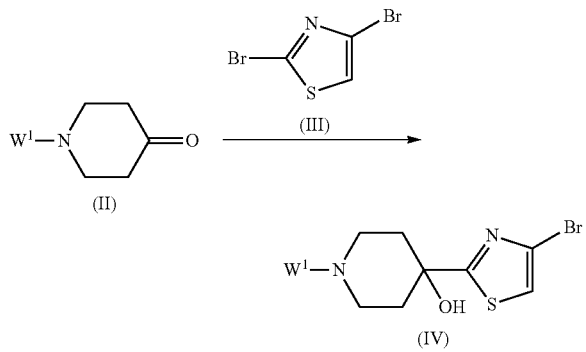

$W^1$ is acetyl, $C_1$-$C_4$-alkoxycarbonyl, benzyl, benzyloxycarbonyl or [3,5-bis(difluoromethyl)-1H-pyrazol-1-yl]acetyl Process A describes the preparation of compounds of the structure (IV) by reaction of compounds of the structure (II) with (III).

One means of preparing the intermediate (IV) from compound (II) is shown in Scheme 1 (Process A). A compound of the general formula (IV) is obtained from a compound of the general formula (III) by halogen-metal exchange and subsequent addition of a compound of the formula (II) (see, for example, *Org. Lett.* 2004, 6, 3083-3085).

Process A is performed in the presence of a suitable organometallic compound. Preferred organometallic compounds are organolithium compounds (for example butyllithium) or Grignard reagents (for example isopropylmagnesium halide).

Process A is preferably performed using one or more diluents. Useful solvents in the performance of the process are preferably aprotic solvents, for example dioxane, glyme, diethyl ether or tetrahydrofuran. Particular preference is given to the use of tetrahydrofuran.

In the performance of process A, the reaction temperatures can be varied within a relatively wide range. In the case of the halogen-metal exchange reactions, the temperatures employed are generally from −120° C. to +150° C. preferably temperatures from −120° C. to +60° C., most preferably −120° C. to 0° C. After the addition of compound (II), preference is given to working at −80° C. to +50° C.

To perform process A, generally from 1 to 2 mol, preferably 1 mol, of the organometallic compound are used per mole of compound of the formula (III). The reaction time is 1 to 48 hours. The workup is effected by the customary methods. If necessary, the compounds are purified by recrystallization, distillation or chromatography, or can optionally also be used in the next step without prior purification.

Process B

Scheme 2: Process B

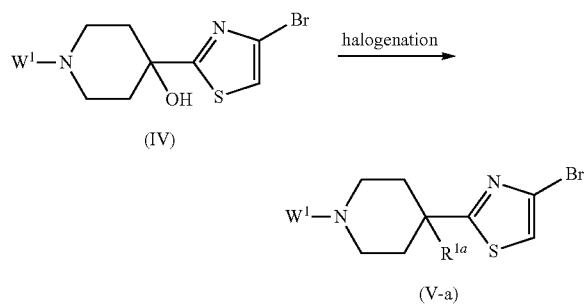

W[1] is acetyl, $C_1$-$C_4$-alkoxycarbonyl, benzyl, benzyloxycarbonyl or [3,5-bis(difluoromethyl)-1H-pyrazol-1-yl]acetyl
R[1a] is F, Cl, Br, I
Process B describes the preparation of compounds of the structure (V-a) by halogenating compounds of the structure (IV).

A compound of the general formula (V-a) in which R[1a]=F, Cl, Br and I is obtained from a compound of the general formula (IV) by halogenation (see, for example, WO 06/133216, WO 04/108692, *J. Med. Chem.*, 1991, 34, 108-122, EP0796846, *J. Antibiot.*, 1988, 41, 134-138, *Bioorg. Med. Chem. Lett.*, 2008, 18, 5209-5212, *Chem. Eur. J.*, 2004, 5640-5648, *Russ. J. Org. Chem.*, 2007, 50-55).

The solvents used may be all customary solvents which are inert under the reaction conditions, or the reaction can be performed in mixtures of two or more of these solvents. Preference is given to using the solvent dichloromethane.

The halogen source used may, for example, be diethylaminosulphur trifluoride, Selectfluor, Deoxofluor, thionyl chloride, $PBr_3$ and methanesulphonyl chloride.

The starting materials and the halogenating agent are used in equimolar amounts. The halogenating agent can also be used in excess. The reaction is normally performed at temperatures of −80 to +80 and preferably at 0 to +40, but it can also be performed at reflux temperature of the reaction mixture. The reaction time varies as a function of the scale of the reaction and the reaction temperature, but is generally between a few minutes and 48 hours.

After the reaction has ended, the compounds (V-a) are separated from the reaction mixture by one of the customary separation techniques. If necessary, the compounds are purified by recrystallization, distillation or chromatography, or can optionally also be used in the next step without prior purification.

Process C

Scheme 3: Process C

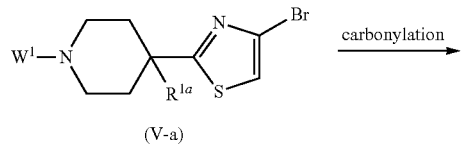

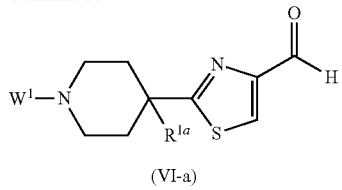

W[1] is acetyl, $C_1$-$C_4$-alkoxycarbonyl, benzyl, benzyloxycarbonyl or [3,5-bis(difluoromethyl)-1H-pyrazol-1-yl]acetyl
R[1a] is F, Cl, Br, I One means of preparing the intermediate (VI-a) from compound (V-a) is shown in Scheme 3 (Process C).

A compound of the general formula (VI-a) is obtained from a compound of the general formula (V-a) by halogen-metal exchange and subsequent addition of an electrophile (e.g. DMF); see, for example, *Tetrahedron*, 2006, 62, 9017-9037; *Org. Lett.* 2005, 7, 339-342; *Synthesis*, 1987, 11, 998-1001.

Process C is performed in the presence of a suitable organometallic compound. Preferred organometallic compounds are organolithium compounds (for example butyllithium).

Process C is preferably performed using one or more diluents. Useful solvents in the performance of process C are preferably aprotic solvents (for example dioxane, glyme, diethyl ether or tetrahydrofuran). Particular preference is given to diethyl ether.

In the performance of process A, the reaction temperatures can be varied within a relatively wide range. In the case of the halogen-metal exchange reactions, the temperatures employed are generally from −120° C. to +150° C., preferably temperatures from −120° C. to +60° C., most preferably −120° C. to −70. After the addition of compound (II), preference is given to working at −80° C. to +50° C.

To perform process C, generally 1 to 2 mol, preferably 1 mol, of the organometallic compound and of the electrophile are used per mole of compound of the formula (V-a). The reaction time is 1 to 48 hours. Work-up is carried out by customary methods. If necessary, the compounds are purified by recrystallization, distillation or chromatography, or can optionally also be used in the next step without prior purification.

Process D

Scheme 4: Process D

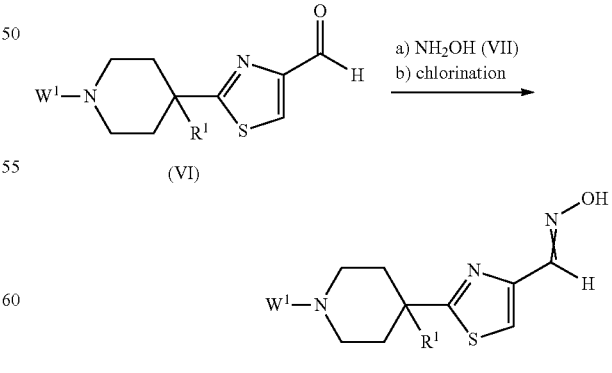

W[1] is acetyl, $C_1$-$C_4$-alkoxycarbonyl, benzyl, benzyloxycarbonyl or [3,5-bis(difluoromethyl)-1H-pyrazol-1-yl]acetyl One means of preparing the intermediate (VIII) from compound (VI) is shown in Scheme 4 (Process D).

A compound of the general formula (VIII) is obtained by condensation of an aldehyde of the formula (VI) with hydroxylamine (VII) and subsequent chlorination (see, for example, WO 05/0040159, WO 08/013622 and Synthesis 1987, 11, 998-1001).

In process D, aldehyde (VI) (VI where $R^1$=H is available from Maybridge) and hydroxylamine (VII) am first reacted (Scheme 4, step (a)). The corresponding oxime is subsequently chlorinated in the presence of a suitable chlorinating agent. Preferred chlorinating reagents are N-chlorosuccinimide, HClO and chlorine. After step (a) of process D, the reaction mixture can be worked up by customary methods or converted further directly in step (b).

Process D is preferably performed using one or more diluents. In step (a) of process D according to the invention, preference is given to using protic solvents, for example ethanol, as the solvent. After the formation of the corresponding oxime from compound (VI), the reaction mixture is diluted in step (b) with a further solvent, for example tetrahydrofuran, and then admixed with aqueous sodium hypochlorite. The chlorination can likewise be effected with the aid of N-chlorosuccinimide in DMF.

In the performance of process D, the reaction temperatures can be varied within a relatively wide range. In general, the temperatures employed are from −10° C. to +150° C. preferably temperatures from 0° C. to +100° C., most preferably reflux temperature of the solvent in step (a), and 0° C. to 30° C. in step (b).

To perform process D, generally 1 to 2 mol, preferably 1 mol, of hydroxylamine (VII) and generally 1 to 5 mol, preferably 1 mol, of a chlorinating reagent are used per mole of compound of the formula (VI). The reaction time is 1 to 48 hours. The workup is effected by customary methods. If necessary, the compounds are purified by recrystallization, distillation or chromatography, or can optionally also be used in the next step without prior purification.

Process E

A compound of the general formula (X-a) or (I-a) is obtained from an alkene of the general formula (IX) and compound (VIII) by a cycloaddition reaction (see, for example, WO08/013622, and Synthesis, 1987, 11, 998-1001).

The alkenes (IX) are commercially available or can be prepared from commercially available precursors by methods described in the literature (for example from ketones or aldehydes by a Wittig or Horner-Wadsworth-Emmons olefination: Chem. Rev. 1989, 89, 863-927 and Julia olefination: Tetrahedron Lett., 1973, 14, 4833-4836; Peterson olefination: J. Org. Chem. 1968, 33, 780).

Process E is performed in the presence of a suitable base. Preferred bases are tertiary amines (e.g. triethylamine), and alkali metal or alkaline earth metal carbonates, hydrogencarbonates and phosphates.

Process E is preferably performed using one or more diluents. In the performance of process E, inert organic solvents are a preferred option (for example toluene and hexane). Water is likewise a possible solvent. Alternatively, process E can be performed in an excess of the alkene (IX).

Typically, a suitable base and the olefin (IX) are initially charged and compound (VIII) is added. Alternatively, compounds (VIII) and (IX) are initially charged and a suitable base is added.

In the performance of process E, the reaction temperatures can be varied within a relatively wide range. In general, the temperatures employed are from −120° C. to +150° C., preferably temperatures of −10° C. to +100° C., most preferably 0° C. to 30° C.

To perform process E, generally 0.5 to 5 mol, preferably 1 mol, of the alkene (IX) are used per mole of compound of the formula (VIII). The reaction time is 1 to 48 hours. The workup is effected by customary methods. If necessary, the compounds are purified by recrystallization, distillation or chromatography, or can optionally also be used in the next step without prior purification.

Process F

Scheme 5: Process E

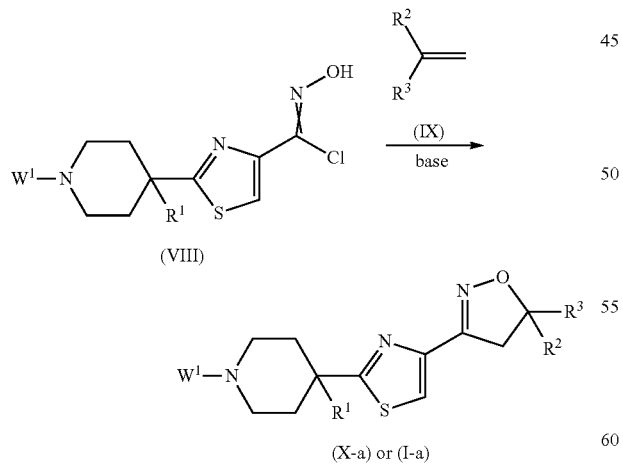

$W^1$ is acetyl, $C_1$-$C_4$-alkoxycarbonyl, benzyl, benzyloxycarbonyl or [3,5-bis(difluoromethyl)-1H-pyrazol-1-yl]acetyl One means of preparing the intermediate (X-a) or the inventive compounds of the formula (I-a) from compound (VIII) is shown in Scheme 5 (Process E).

Scheme 6: Process F

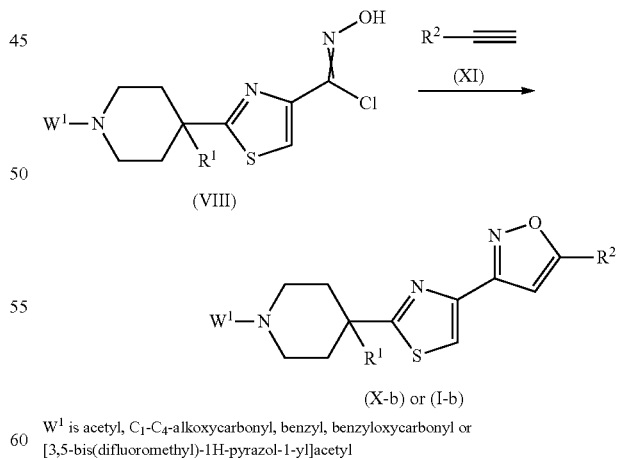

$W^1$ is acetyl, $C_1$-$C_4$-alkoxycarbonyl, benzyl, benzyloxycarbonyl or [3,5-bis(difluoromethyl)-1H-pyrazol-1-yl]acetyl One means of preparing the intermediate (X-b) or the inventive compounds of the formula (I-b) from compound (VIII) is shown in Scheme 6 (Process F).

A compound of the general formula (X-b) or (I-b) is obtained from an alkyne of the general formula (XI) and compound (VIII) by a cycloaddition reaction (see, for example, WO 08/013622, WO 05/040159 and *Synthesis*, 1987, 11, 998-1001).

The alkynes (XI) are commercially available or can be prepared from commercially available precursors by methods described in the literature (for example from ketones or aldehydes by a Corey-Fuchs reaction: *Tetrahedron Lett.* 1972, 36, 3769-3772, Seyferth-Gilbert homologization: *J. Org. Chem.*, 1996, 61, 2540-2541, or with Bestmann-Ohira's reagent: *Synthesis* 2004, 1, 59-62).

Process F is performed in the presence of a suitable base. Preferred bases are tertiary amines (e.g. triethylamine), and alkali metal or alkaline earth metal carbonates, hydrogencarbonates and phosphates.

Process F is preferably performed using one or more diluents. In the performance of process F, inert organic solvents are a preferred option, for example toluene and hexane. Water is likewise a possible solvent. Alternatively, process F can be performed in an excess of the alkyne (XI).

Typically, a suitable base and the alkyne (XI) are initially charged and compound (VIII) is added. Alternatively, compounds (VIII) and (XI) are initially charged and a suitable base is added.

In the performance of process F, the reaction temperatures can be varied within a relatively wide range. In general, the temperatures employed are from −120° C. to +150° C., preferably temperatures of −10° C. to +100° C., most preferably 0° C. to 30° C.

To perform process F, generally 0.5 to 5 mol, preferably 1 mol, of the alkyne (XI) are used per mole of compound of the formula (VIII). The reaction time is 1 to 48 hours. The workup is effected by customary methods. If necessary, the compounds are purified by recrystallization, distillation or chromatography, or can optionally also be used in the next step without prior purification.
Process G sis with hydrogen in the presence of a catalyst (for example palladium on activated carbon).

Useful solvents are all customary solvents which are inert under the reaction conditions, for example alcohols (e.g. methanol, ethanol, propanol), cyclic and acyclic ethers (e.g. diethyl ether, tetrahydrofuran, dioxane), aromatic hydrocarbons (e.g. benzene, toluene, xylene), halogenated hydrocarbons (e.g. dichloromethane, chloroform, carbon tetrachloride), halogenated aromatic hydrocarbons (e.g. chlorobenzene, dichlorobenzene), nitriles (e.g. acetonitrile), carboxylic esters (e.g. ethyl acetate), amides (e.g. N,N-dimethylformamide, N,N-dimethylacetamide), dimethyl sulphoxide, 1,3-dimethyl-2-imidazolinone, water and acetic acid, or the reaction can be performed in mixtures of two or more of these solvents.

Acids which can be used for this reaction of deprotection of t-butoxycarbonyl and benzyloxycarbonyl groups are, for example, trifluoroacetic acid, hydrochloric acid or other acids as described in the literature (for example "*Protective Groups in Organic Synthesis*"; Third Edition; 1999; pp. 494-653).

The reaction is normally performed at temperatures of 0° C. to +150° C. and preferably at room temperature, but it can also be performed at reflux temperature of the reaction mixture. The reaction time varies as a function of the scale of the reaction and the reaction temperature, but is generally between half an hour and 72 hours.

After the reaction has ended, the compounds (XII) are separated from the reaction mixture by one of the customary separation techniques. If necessary, the compounds are purified by recrystallization, distillation or chromatography, or can, if desired, also be used in the next step without prior purification. It is also possible to isolate the compound of the general formula (XII) as a salt, for example as a salt of hydrochloric acid or of trifluoroacetic acid.
Process H Scheme 7: Process G

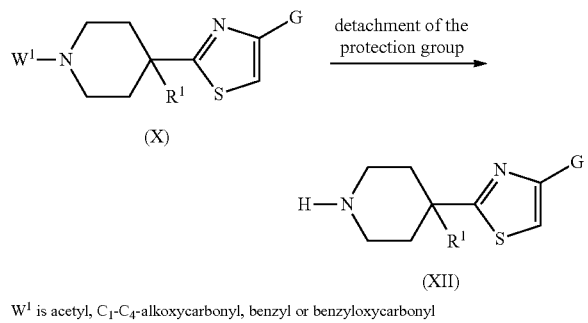

$W^1$ is acetyl, $C_1$-$C_4$-alkoxycarbonyl, benzyl or benzyloxycarbonyl

Scheme 8: Process H

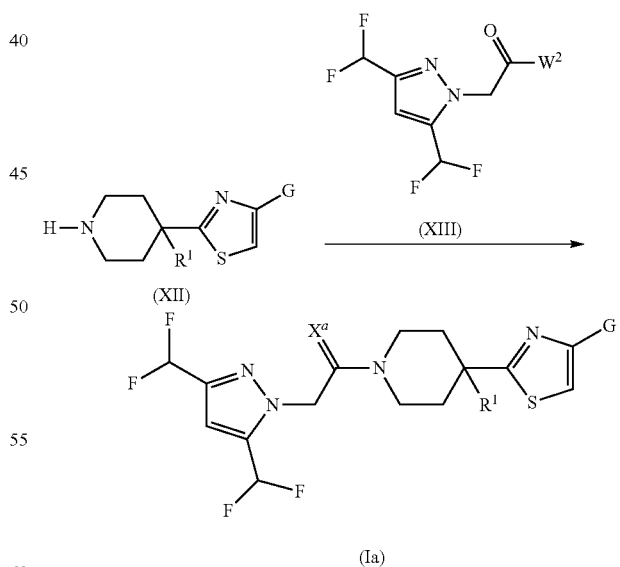

$W^2$ is chlorine or OH
$X^a$ is oxygen

One means of preparing compounds of the formula (XII) from corresponding compounds (X) is shown in Scheme 7.

A compound of the formula (X) is converted to a compound of the formula (XII) by suitable methods for removing protecting groups, which are described in the literature ("*Protective Groups in Organic Synthesis*"; Third Edition; 1999; 494-653, and literature cited therein).

tert-Butoxycarbonyl and benzyloxycarbonyl protecting groups can be removed in an acidic medium (for example with hydrochloric acid or trifluoroacetic acid). Acetyl protecting groups can be removed under basic conditions (for example with potassium carbonate or caesium carbonate). Benzylic protecting groups can be removed by hydrogenoly- One means of preparing compounds of the formula (Ia) from corresponding compounds (XII) is shown in Scheme 8.

A compound with the general formula (Ia) can be synthesized analogously to methods described in the literature (see, for example WO 07/147336), by a coupling reaction of a compound with the corresponding general formula (XII) with a substrate of the general formula (XIIIa) where $W^{2a}$=chlorine, optionally in the presence of an acid scavenger/base.

Compounds (XIIIa) ($W^{2a}$=chlorine) or (XIIIb) ($W^{2b}$=OH) are either commercially available or can be prepared by processes described in the literature (see, for example, WO 08/013622 and WO 08/013925). In addition, a substrate with the general formula (XIIIa) where $W^{2a}$=chlorine can be prepared from the corresponding acid ($W^{2b}$=OH) by chlorination using processes known from the literature (e.g. *Tetrahedron* 2005, 61, 10827-10852, and literature cited therein).

The substituents $R^2$ can be modified by reaction methods which are common knowledge to those skilled in the art at all stages of the synthesis in which they occur. For example, OH, $NH_2$ or SH functionalities can be alkylated by known methods with suitable halides or sulphates (see, for example, J. March: Advanced Organic Chemistry—Reactions, Mechanisms, and Structures, 4th Ed. (1992), Wiley, New York, pages 388-390, 406-407, 411-415), acrylated using suitable carboxylic acids, carbonyl chlorides or carboxylic anhydrides (see J. March: Advanced Organic Chemistry—Reactions, Mechanisms, and Structures, 4th Ed. (1992), Wiley, New York, pages 392-400, 409, 417-419) or sulphonylated using suitable sulphonyl chlorides (see J. March: Advanced Organic Chemistry—Reactions, Mechanisms, and Structures, 4th Ed. (1992), Wiley. New York, pages 496-500). It is also possible to convert hydroxyl compounds with halogenating agents to corresponding halides (see, for example, J. March: Advanced Organic Chemistry—Reactions, Mechanisms, and Structures, 4th Ed. (1992), Wiley, New York, pages 431-434). These halides in turn can be etherified with the aid of suitable hydroxyl compounds (see, for example, J. March: Advanced Organic Chemistry—Reactions, Mechanisms, and Structures, 4th Ed. (1992). Wiley, New York, pages 388-390). It is also possible to reduce carbonyl functionalities by familiar methods to corresponding hydroxyl compounds (see, for example, J. March: Advanced Organic Chemistry—Reactions, Mechanisms, and Structures, 4th Ed. (1992), Wiley, New York, pages 443, 910-918) or, in the case of aldehydes, to carboxylic acids (see, for example, J. March: Advanced Organic Chemistry—Reactions, Mechanisms, and Structures, 4th Ed. (1992), Wiley, New York, pages 701-703), which can in turn be converted to the corresponding esters (see, for example, J. March: Advanced Organic Chemistry— Reactions, Mechanisms, and Structures, 4th Ed. (1992). Wiley, New York, pages 393-396). Finally, thioethers can be oxidized using suitable oxidizing agents to sulphoxides or sulphones (see, for example, J. March: Advanced Organic Chemistry—Reactions, Mechanisms, and Structures, 4th Ed. (1992), Wiley, New York, pages 1201-1202). Examples of such reactions can be found in the synthesis part of this application.

The solvents used may be all customary solvents which are inert under the reaction conditions, for example cyclic and acyclic ethers (e.g. diethyl ether, tetrahydrofuran, dioxane), aromatic hydrocarbons (e.g. benzene, toluene, xylene), halogenated hydrocarbons (e.g. dichloromethane, chloroform, carbon tetrachloride), halogenated aromatic hydrocarbons (e.g. chlorobenzene, dichlorobenzene) and nitriles (e.g. acetonitrile), or the reaction can be performed in mixtures of two or more of these solvents. The preferred solvents are tetrahydrofuran and dichloromethane.

At least one equivalent of an acid scavenger/a base (for example Hünig's base, triethylamine or commercially available polymeric acid scavengers) is used, in relation to the starting material of the general formula (XII). If the starting material is a salt, at least two equivalents of the acid scavenger are required.

The reaction is normally performed at temperatures of 0 to 100 and preferably at 20 to 30, but it can also be performed at reflux temperature of the reaction mixture. The reaction time varies as a function of the scale of the reaction and the reaction temperature, but is generally between a few minutes and 48 hours.

After the reaction has ended, the compounds (I) are separated from the reaction mixture by one of the customary separation techniques. If necessary, the compounds are purified by recrystallization, distillation or chromatography, or can optionally also be used in the next step without prior purification.

Alternatively, a compound of the formula (Ia) can also be synthesized from the corresponding compound of the formula (XII) with a substrate of the formula (XIIIb) where $W^{2b}$=OH in the presence of a coupling reagent, analogously to methods described in the literature (e.g. *Tetrahedron* 2005, 61, 10827-10852, and references cited therein).

Suitable coupling reagents are, for example, peptide coupling reagents (for example N-(3-dimethylaminopropyl)-N'-ethylcarbodiimide mixed with 4-dimethylaminopyridine, N-(3-dimethylaminopropyl)-N'-ethylcarbodiimide mixed with 1-hydroxybenzotriazole, bromotripyrrolidinophosphonium hexafluorophosphate, O-(7-azabenzotriazol-1-yl)-N,N,N',N'-tetramethyluronium hexafluorophosphate, etc.).

If appropriate, a base, for example triethylamine or Hünig's base, can be used in the reaction.

The solvents used may be all customary solvents which are inert under the reaction conditions, for example alcohols (e.g. methanol, ethanol, propanol), cyclic and acyclic ethers (e.g. diethyl ether, tetrahydrofuran, dioxane), aromatic hydrocarbons (e.g. benzene, toluene, xylene), halogenated hydrocarbons (e.g. dichloromethane, chloroform, carbon tetrachloride), halogenated aromatic hydrocarbons (e.g. chlorobenzene, dichlorobenzene), nitriles (e.g. acetonitrile) and amides (e.g. N,N-dimethylformamide, N,N-dimethylacetamide), or the reaction can be performed in mixtures of two or more of these solvents. The preferred solvent is dichloromethane.

The reaction is normally performed at temperatures of 0□-100□ and preferably at 0□-30° C., but it can also be carried out at reflux temperature of the reaction mixture. The reaction time varies as a function of the scale of the reaction and the reaction temperature, but is generally between a few minutes and 48 hours.

After the reaction has ended, the compounds (Ia) are separated from the reaction mixture by one of the customary separation techniques. If necessary, the compounds are purified by recrystallization, distillation or chromatography, or can optionally also be used in the next step without prior purification.

Process I

Scheme 9: Process I

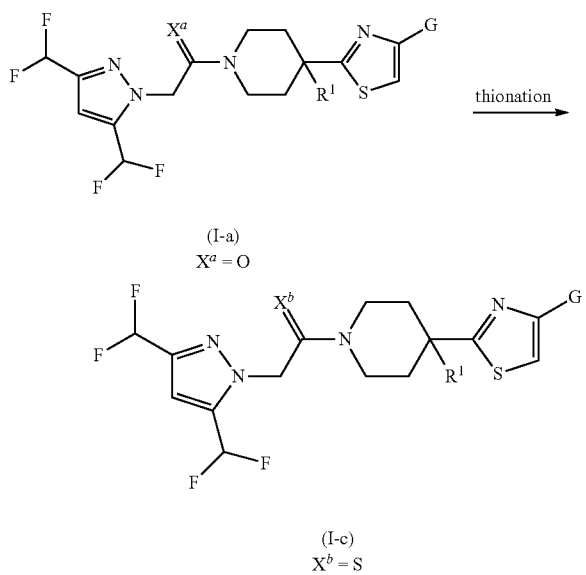

One means of preparing compounds of the formula (I-c) in which $X^b$=sulphur from corresponding compounds (Ia) in which $X^a$ is oxygen is shown in Scheme 9.

The solvents used may be all customary solvents which are inert under the reaction conditions, for example alcohols (e.g. methanol, ethanol, propanol), cyclic and acyclic ethers (e.g. diethyl ether, tetrahydrofuran, dioxane), aromatic hydrocarbons (e.g. benzene, toluene, xylene), halogenated hydrocarbons (e.g. dichloromethane, chloroform, carbon tetrachloride), halogenated aromatic hydrocarbons (e.g. chlorobenzene, dichlorobenzene), nitriles (e.g. acetonitrile), carboxylic esters (e.g. ethyl acetate) and amides (e.g. N,N-dimethylformamide, N,N-dimethylacetamide), and the reaction can be performed in mixtures of two or more of these solvents. The preferred solvents are chloroform and 1,2-dimethoxyethane.

Suitable thionating reagents are, for example, Lawesson's reagent (see *Tetrahedron* 1986, 42, 6555-6564, *Tetrahedron Lett.* 1993, 46, 7459-7462) and phosphorus pentasulphide. The starting material and the thionating reagent are used in equimolar amounts, but the thionating reagent may optionally also be used in excess.

The reaction is normally performed at temperatures of 0☐ to 150☐ and preferably at 0☐ to 100☐, but it can also be performed at reflux temperature of the reaction mixture. The reaction time varies as a function of the scale of the reaction and the reaction temperature, but is generally between a few minutes and 48 hours.

After the reaction has ended, the compounds (Ib) in which $X^b$=sulphur are separated from the reaction mixture by one of the customary separation techniques. If necessary, the compounds are purified by recrystallization, distillation or chromatography.

Process J

Scheme 10: Process J

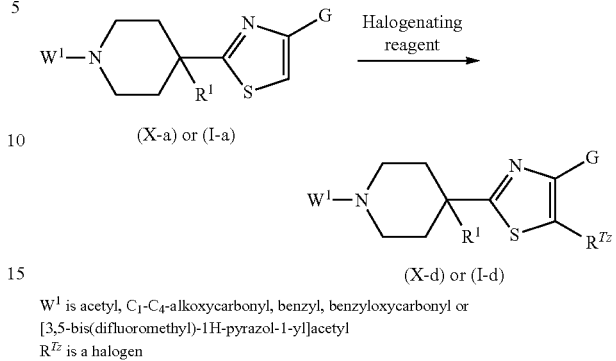

$W^1$ is acetyl, $C_1$-$C_4$-alkoxycarbonyl, benzyl, benzyloxycarbonyl or [3,5-bis(difluoromethyl)-1H-pyrazol-1-yl]acetyl
$R^{Tz}$ is a halogen One means of preparing the intermediate (X-d) or the inventive compounds of the formula (I-d) from compound (X-a) or (I-a) is shown in Scheme 10 (Process J).

A compound of the general formula (X-d) or (I-d) is obtained from compound (X-a) or (I-a) by halogenation (see, for example, WO 08/013622, WO 05/040159 and *Synthesis*, 1987, 11, 998-1001).

The solvents used may be all customary solvents which are inert under the reaction conditions, such as cyclic and acyclic ethers (e.g. diethyl ether, tetrahydrofuran, dioxane), aromatic hydrocarbons (e.g. benzene, toluene, xylene), halogenated hydrocarbons (e.g. dichloromethane, chloroform, carbon tetrachloride), halogenated aromatic hydrocarbons (e.g. chlorobenzene, dichlorobenzene), nitriles (e.g. acetonitrile), carboxylic acids (e.g. acetic acid) and carboxylic esters (e.g. ethyl acetate), and the reaction can be performed in mixtures of two or more of these solvents. The preferred solvents are chloroform and acetic acid.

Preferred halogenating reagents are, for example, N-chlorosuccinimide, HClO and chlorine (chlorinating reagents), N-bromosuccinimide, HBrO and bromine (brominating reagents), N-fluorodibenzenesulphonimide (NFSI) and $F_2$ (fluorinating reagents) or N-iodosuccinimide, ICl and iodine (iodinating reagents; see J. March: Advanced Organic Chemistry—Reactions, Mechanisms, and Structures, 4th Ed. (1992), Wiley, New York, pages 531-534; D. Kikelj, U. Urleb in Science of Synthesis, 11 (2001), pages 749-751). The starting material and the halogenating reagent are used in equimolar amounts, but the halogenating reagent can optionally also be used in excess.

The reaction is normally performed at temperatures of −10° C. to −1-200° C., and preferably at 0° C. to 100° C., but it can also be performed at reflux temperature of the reaction mixture. The reaction time varies as a function of the scale of the reaction and of the reaction temperature, but is generally between a few minutes and 48 hours.

After the reaction has ended, the compounds (X-d) or (I-d) are separated from the reaction mixture by one of the customary separation techniques. If necessary, the compounds are purified by recrystallization, distillation or chromatography.

The invention further provides for the non-medical use of the inventive bis(difluoromethyl)pyrazole derivatives for control of unwanted microorganisms.

The invention further provides a composition for controlling unwanted microorganisms, comprising at least one bis(difluoromethyl)pyrazole derivative according to the present invention.

The invention also relates to a method for controlling unwanted microorganisms, characterized in that the inventive bis(difluoromethyl)pyrazole derivatives are applied to the microorganisms and/or in their habitat.

The invention further relates to seed which has been treated with at least one inventive bis(difluoromethyl)pyrazole derivative.

The invention finally provides a method for protecting seed against unwanted microorganisms by using seed treated with at least one bis(difluoromethyl)pyrazole derivative according to the present invention.

The inventive substances have potent microbicidal action and can be used to control unwanted microorganisms, such as fungi and bacteria, in crop protection and in the protection of materials.

The inventive bis(difluoromethyl)pyrazole derivatives of the formula (I) have very good fungicidal properties and can be used in crop protection, for example for controlling Plasmodiophoromycetes. Oomycetes, Chytridiomycetes, Zygomycetes, Ascomycetes, Basidiomycetes and Deuteromycetes.

Bactericides can be used in crop protection, for example to control Pseudomonadaceae. Rhizobiaceae, Enterobacteriaceae, Corynebacteriaceae and Streptomycetaceae.

The inventive fungicidal compositions can be used for curative or protective control of phytopathogenic fungi. The invention therefore also relates to curative and protective methods for controlling phytopathogenic fungi by means of use of the inventive active ingredients or compositions which are applied to the seed, the plant or plant parts, the fruit or the soil in which the plants grow.

The inventive compositions for controlling phytopathogenic fungi in crop protection comprise an effective but non-phytotoxic amount of the inventive active ingredients. An "effective but non-phytotoxic amount" means an amount of the inventive composition which is sufficient for adequate control of the fungal disease of the plant or to eradicate the fungal disease completely, and which, at the same time, does not cause any significant symptoms of phytotoxicity. In general, this application rate may vary within a relatively wide range. It depends on several factors, for example on the fungus to be controlled, the plant, the climatic conditions and the ingredients of the inventive compositions.

All plants and plant parts can be treated in accordance with the invention. Plants are understood here to mean all plants and plant populations such as desired and unwanted wild plants or crop plants (including naturally occurring crop plants). Crop plants may be plants which can be obtained by conventional breeding and optimization methods or by biotechnological and genetic engineering methods or combinations of these methods, including the transgenic plants and including the plant varieties which can or cannot be protected by varietal property rights. Plant parts are understood to mean all parts and organs of plants above and below the ground, such as shoot, leaf, flower and root, examples of which include leaves, needles, stalks, stems, flowers, fruit bodies, fruits, seeds, roots, tubers and rhizomes. Parts of plants also include harvested plants and vegetative and generative propagation material, for example seedlings, tubers, rhizomes, cuttings and seeds.

The plants which can be treated in accordance with the invention include the following: cotton, flax, grapevine, fruit, vegetables, such as Rosaceae sp. (for example pome fruits such as apples and pears, but also stone fruits such as apricots, cherries, almonds and peaches, and soft fruits such as strawberries), Ribesioidae sp., Juglandaceae sp., Betulaceae sp., Anacardiaceae sp., Fagaceae sp., Moraceae sp., Oleaceae sp., Actinidaccae sp., Lauraceae sp., Musaceae sp. (for example banana plants and banana plantations), Ruhiaceae sp. (for example coffee), Theaceae sp., Sterculiceae sp., Rutaceae sp. (for example lemons, oranges and grapefruit); Solanaceae sp. (for example tomatoes). Liliaceae sp., Asleraceae sp. (for example lettuce), Umbelliferae sp., Cruciferae sp., Chenopodiaceae sp., Cucurbitaceae sp. (for example cucumber), Alliaceae sp. (for example leeks, onions), Papilionaceue sp. (for example peas); major crop plants such as Gramineae sp. (for example maize, turf, cereals such as wheat, rye, rice, barley, oats, millet and triticale), Asteraceae sp. (for example sunflower), Brassicaceae sp. (for example white cabbage, red cabbage, broccoli, cauliflower, Brussels sprouts, pak choi, kohlrabi, radishes, and oilseed rape, mustard, horseradish and cress), Fabacae sp. (for example beans, peanuts), Papilionaceae sp. (for example soybean), Solanaceae sp. (for example potatoes), Chenopmliaceae sp. (for example sugar beet, fodder beet, Swiss chard, beetroot); useful plants and ornamental plants in gardens and forests; and in each case genetically modified types of these plants.

Non-limiting examples of pathogens of fungal diseases which can be treated in accordance with the invention include the following:

diseases caused by powdery mildew pathogens, for example *Blumeria* species, for example *Blumeria graminis; Podosphaera* species, for example *Podosphaera leucotricha; Sphaerotheca* species, for example *Sphaerotheca fuliginea; Uncinula* species, for example *Uncinula necator;* diseases caused by rust disease pathogens, for example *Gymnosporangium* species, for example *Gymnosporangium sabinae; Hemileia* species, for example *Hemileia vastatrix; Phakopsora* species, for example *Phakopsora pachyrhizi* or *Phakopsora meibomiae; Puccinia* species, for example *Puccinia recondita, Puccinia graminis* or *Puccinia striiformis; Uromyces* species, for example *Uromyces appendiculatus;* diseases caused by pathogens from the group of the Oomycetes, for example *Albugo* species, for example *Albugo candida; Bremia* species, for example *Bremia lactucae; Peronospora* species, for example *Peronospora pisi* or *P. brassicae; Phytophthora* species, for example *Phytophthora infestans; Plasmopara* species, for example *Plasmopara viticola; Pseudoperonospora* species, for example *Pseudoperonospora humuli* or *Pseudoperonospora cubensis; Pythium* species, for example *Pythium ultimum;* leaf blotch diseases and leaf wilt diseases caused, for example, by *Alternaria* species, for example *Alternaria solani; Cercospora* species, for example *Cercospora beticola; Cladiosporium* species, for example *Cladiosporium cucumerinum; Cochliobolus* species, for example *Cochliobolus sativus* (conidial form: *Drechslera,* syn: *Helminthosporium*) or *Cochliobolus miyabeanus; Colletotrichum* species, for example *Colletotrichum lindemuthanium; Cycloconium* species, for example *Cycloconium oleaginum; Diaporthe* species, for example *Diaporthe citri; Elsinoe* species, for example *Elsinoe fawcettii; Gloeosporium* species, for example *Gloeosporium laeticolor; Glomerella* species, for example *Glomerella cingulata; Guignardia* species, for example *Guignardia bidwelli; Leptosphaeria* species, for example *Leptosphaeria maculans; Magnaporthe* species, for example *Magnaporthe grisea; Microdochium* species, for example *Microdochium nivale; Mycosphaerella* species, for example *Mycosphaerella graminicola, Mycosphaerella arachidicola* or *Mycosphaerella fijiensis; Phaeosphaeria* species, for example *Phaeosphaeria nodorum; Pyrenophora* species, for example *Pyrenophora teres* or *Pyrenophora tritici repentis; Ramularia* species, for example *Ramularia collo-cygni* or *Ramularia areola; Rhynchosporium* species, for example *Rhynchosporium secalis; Septoria* species, for example *Septoria apii* or *Septoria lycopersici; Stagonospora* species, for example *Stagonospora nodorum; Typhula* species, for example *Typhula incamata; Venturia* species, for example *Venturia inaequalis;* root and stem diseases caused, for example, by *Corticium* species, for example *Corticium gratninearum; Fusarium* species, for example *Fusarium oxysporum; Gaeumannomyces* species, for example *Gaeumannomyces graminis; Plasmodiophora* species, for example *Plasmodiophora brassicae; Rhizoctonia* species, for example *Rhizoctonia solani; Sarocladium* species, for example *Sarocladium oryzae; Sclerotium* species, for example *Sclerotium olyzae; Tapesia* species, for example *Tapesia acuformis; Thielaviopsis* species, for example *Thielaviopsis basicola;* ear and panicle diseases (including corn cobs) caused, for example, by *Alternaria* species, for example *Alternaria* spp.; *Aspergillus* species, for example *Aspergillus flavus; Cladosporium* species, for example *Cladosporium cladosporioides; Claviceps* species, for example *Claviceps purpurea; Fusarium* species, for example *Fusarium culmorum; Gibberella* species, for example *Gibberella zeae; Monographella* species, for example *Monographella nivalis; Stagonospora* species, for example *Stagonospora nodorum;* diseases caused by smut fungi, for example *Sphacelotheca* species, for example *Sphacelotheca reiliana; Tilletia* species, for example *Tilletia caries* or *Tilletia controversa; Urocystis* species, for example *Urocystis occulta; Ustilago* species, for example *Ustilago nuda;* fruit rot caused, for example, by *Aspergillus* species, for example *Aspergillus flavus; Botrytis* species, for example *Botrytis cinerea: Penicillium* species, for example *Penicillium expansum* or *Penicillium purpurogenum; Rhizopus* species, for example *Rhizopus stolonifer; Sclerotinia* species, for example *Sclerotinia sclerotionnu; Verticilium* species, for example *Verticilium alboatrum;* seed- and soil-borne rot and wilt diseases, and also seedling diseases, caused, for example, by *Alternaria* species, for example *Alternaria brassicicola; Aphanomyces* species, for example *Aphanomyces euteiches; Ascochyta* species, for example *Ascochyta lentis; Aspergillus* species, for example *Aspergillus flavus; Cladosporium* species, for example *Cladosporium herbarum; Cochliobolus* species, for example *Cochliobolus sativus* (conidial form: *Drechslera, Bipolaris* Syn: *Helminthosporium*); *Colletotrichum* species, for example *Colletotrichum coccodes; Fusarium* species, for example *Fusarium culmorum; Gibberella* species, for example *Gibberella zeae; Macrophomina* species, for example *Macrophomina phaseolina; Microdochium* species, for example *Microdochium nivale; Monographella* species, for example *Monographella nivalis; Penicillium* species, for example *Penicillium expansum; Phoma* species, for example *Phoma lingam; Phomopsis* species, for example *Phomopsis sojae; Phytophthora* species, for example *Phytophthora cactorum; Pyrenophora* species, for example *Pyrenophora graminea; Pyricularia* species, for example *Pyricularia oryzae; Pythium* species, for example *Pythium ultimum; Rhizoctonia* species, for example *Rhizoctonia solani; Rhizopus* species, for example *Rhizopus oryzae; Sclerotium* species, for example *Sclerotium rolfsii; Septoria* species, for example *Septoria nodorum; Typhula* species, for example *Typhula incamata; Verticillium* species, for example *Verticillium dahliae;* cancers, galls and witches' broom caused, for example, by *Nectria* species, for example *Nectria galligena;* wilt diseases caused, for example, by *Monilinia* species, for example *Monilinia laxa;* deformations of leaves, flowers and fruits caused, for example, by *Exobasidium* species, for example *Exobasidium vexans; Taphrina* species, for example *Taphrina deformans;* degenerative diseases in woody plants, caused, for example, by *Esca* species, for example *Phaeomoniella chlainydospora, Phaeoacremonium aleophilum* or *Fomitiporia mediterranea; Ganodenna* species, for example *Ganoderma boninense;* diseases of flowers and seeds caused, for example, by *Botrytis* species, for example *Botrytis cinerea;* diseases of plant tubers caused, for example, by *Rhizoctonia* species, for example *Rhizoctonia solani; Helminthosporium* species, for example *Helminthosporium solani;* diseases caused by bacterial pathogens, for example *Xanthomonas* species, for example *Xanthomonas campestris* pv. *oryzae; Pseudomonas* species, for example *Pseudomonas syringae* pv. *lachrymans; Erwinia* species, for example *Erwinia amylovora.*

Preference is given to controlling the following diseases of soybeans:

Fungal diseases on leaves, stems, pods and seeds caused, for example, by *alternaria* leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)). dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*). phyllostica leaf spot (*Phyllostica sojaecola*), pod and stem blight (*Phomopsis sojae*), powdery mildew (*Microsphaera diffusa*), pyrenochaeta leaf spot (*Pyrenochaeta glycines*). rhizoctonia aerial, foliage, and web blight (*Rhizoctonia solani*), rust (*Phakopsora pachyrhizi, Phakopsora meibomiae*), scab (*Sphaceloma glycines*). stemphylium leaf blight (*Stemphylium bohyosum*), target spot (*Corynespora cassiicola*).

Fungal diseases on roots and the stem base caused, for example, by black root rot (*Calonectria crotalariae*), charcoal rot (*Macrophomina phascolina*), fusarium blight or wilt, root rot, and pod and collar rot (*Fusarium oxysporum. Fusarium orthoceras, Fusarium semitectum, Fusarium equiseti*). mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*). phytophthora rot (*Phytophthora megasperma*), brown stem rot (*Phialophora gregata*), pythium rot (*Pythium aphanidermatum, Pythium irregulars, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The inventive active ingredients also have very good fortifying action in plants. They are therefore suitable for mobilizing the defences of the plant against attack by undesirable microorganisms.

Plant-strengthening (resistance-inducing) substances are understood to mean, in the present context, those substances which are capable of stimulating the defence system of plants in such a way that the treated plants, when subsequently inoculated with undesirable microorganisms, display a high degree of resistance to these microorganisms.

In the present case, undesirable microorganisms are understood to mean phytopathogenic fungi and bacteria. The inventive substances can thus be used to protect plants for a certain period after the treatment against attack by the pathogens mentioned. The period for which protection is provided generally extends over 1 to 10 days, preferably 1 to 7 days, after the treatment of the plants with the active ingredients.

The fact that the active ingredients are well tolerated by plants at the concentrations necessary for controlling plant diseases permits treatment of above-ground parts of plants, of propagation stock and seeds, and of the soil.

The inventive active ingredients can be used particularly successfully for controlling diseases in viticulture and potato, fruit and vegetable growing, for example especially against downy mildew fungi and Oomycetes, for example *Phytophthora, Plasmopara, Pseudoperonospora* and *Pythium* species.

The inventive active ingredients are also suitable for enhancing the yield of crops. In addition, they have low toxicity and are well tolerated by plants.

If appropriate, the inventive compounds can, at certain concentrations or application rates, also be used as herbicides, safeners, growth regulators or compositions to improve plant properties, or as microbicides, for example as fungicides, antimycotics, bactericides, viricides (including compositions to counteract viroids) or as compositions to counteract MLO (mycoplasma-like organisms) and RLO (rickettsia-like organisms). If appropriate, they can also be used as insecticides. If appropriate, they can also be used as intermediates or precursors for the synthesis of other active ingredients.

The inventive active ingredients, when they are well tolerated by plants, have favourable homeotherm toxicity and are well tolerated by the environment, are suitable for protecting plants and plant organs, for enhancing harvest yields, for improving the quality of the harvested material in agriculture, in horticulture, in animal husbandry, in forests, in gardens and leisure facilities, in the protection of stored products and of materials, and in the hygiene sector. They may be preferably used as crop protection compositions. They are effective against normally sensitive and resistant species, and against all or some stages of development.

The inventive treatment of the plants and plant parts with the active ingredients or compositions is effected directly or by action on their surroundings, habitat or storage space by the customary treatment methods, for example by dipping, spraying, atomizing, irrigating, evaporating, dusting, logging, broadcasting, foaming, painting, spreading-on, watering (drenching), drip irrigating and, in the case of propagation material, especially in the case of seeds, also by dry seed treatment, wet seed treatment, slurry treatment, by incrusting, by coating with one or more coats, etc. It is also possible to apply the active ingredients by the ultra-low volume method or to inject the active ingredient preparation or the active ingredient itself into the soil.

The inventive active ingredients or compositions can also be used in the protection of materials, for protecting industrial materials against attack and destruction by unwanted microorganisms, for example fungi.

Industrial materials in the present context are understood to mean inanimate materials which have been prepared for use in industry. For example, industrial materials which are to be protected by inventive active ingredients from microbial change or destruction may be adhesives, sizes, paper and board, textiles, leather, wood, paints and plastic articles, cooling lubricants and other materials which can be infected with, or destroyed by, microorganisms. The range of materials to be protected also includes parts or production plants, for example cooling water circuits, which may be impaired by the proliferation of microorganisms. In the context of the present invention, industrial materials preferably include adhesives, sizes, paper and hoard, leather, wood, paints, cooling lubricants and heat-transfer liquids, more preferably wood. The inventive active ingredients or compositions may prevent adverse effects such as rotting, decay, discolouration, decolouration or formation of mould.

The inventive method for controlling unwanted fungi can also be employed for protecting storage goods. Storage goods are understood to mean natural substances of vegetable or animal origin, or processed products thereof, which are of natural origin and for which long-term protection is desired. Storage goods of vegetable origin, for example plants or plant parts, such as stems, leaves, tubers, seeds, fruits, grains, can be protected in the freshly harvested state or after processing by (pre)drying, moistening, comminuting, grinding, pressing or roasting. Storage goods also include timber, whether unprocessed, such as construction timber, electricity poles and barriers, or in the form of finished products, such as furniture. Storage goods of animal origin are, for example, hides, leather, furs and hairs. The inventive active ingredients may prevent adverse effects such as rotting, decay, discolouration, decolouration or formation of mould.

Microorganisms capable of degrading or changing the industrial materials include, for example, bacteria, fungi, yeasts, algae and slime organisms. The inventive active ingredients are preferably effective against fungi, especially moulds, wood-discoloring and wood-destroying fungi (Basidiomycetes), and against slime organisms and algae. Examples include microorganisms of the following genera: *Alternaria*, such as *Alternaria tenuis; Aspergillus*, such as *Aspergillus niger; Chaetomium*, such as *Chaetomium globosum; Coniophora*, such as *Coniophora puetana; Lentinus*, such as *Lentinus tigrinus; Penicillium*, such as *Penicillium glaucum; Polyporus*, such as *Polyponis versicolor; Aureobasidium*, such as *Aureobasidium pullulans; Sclerophoma*, such as *Sclerophoma pityophila; Trichoderma*, such as *Trichoderma viride; Eschcrichia*, such as *Eschcrichia coli; Pseudomonas*, such as *Pseudomonas aeruginosa; Staphylococcus*, such as *Staphylococcus aureus.*

The present invention further relates to a composition for controlling unwanted microorganisms, comprising at least one of the inventive bis(difluoromethyl)pyrazole derivatives. These are preferably fungicidal compositions which comprise agriculturally usable auxiliaries, solvents, carriers, surfactants or extenders.

According to the invention, a carrier is a natural or synthetic, organic or inorganic substance with which the active ingredients are mixed or bonded for better applicability, in particular for application to plants or plant parts or seed. The carrier, which may be solid or liquid, is generally inert and should be usable in agriculture.

Useful solid carriers include: for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and also granules of organic material such as paper, sawdust, coconut shells, corn cobs and tobacco stalks; suitable emulsifiers and/or foam formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates: suitable dispersants are nonionic and/or ionic substances, for example from the classes of the alcohol-POE and/or -POP ethers, acid and/or POP-POE esters, alkylaryl and/or POP-POE ethers, fat and/or POP-POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Further suitable oligomers or polymers are, for example, those derived from vinylic monomers, from acrylic acid, from EO and/or PO alone or in combination with, for example, (poly)alcohols or (poly)amines. It is also possible to use lignin and its sulphonic acid derivatives, unmodified and modified celluloses, aromatic and/or aliphatic sulphonic acids and also their adducts with formaldehyde.

The active ingredients can be converted to the customary formulations, such as solutions, emulsions, wettable powders, water- and oil-based suspensions, powders, dusts, pastes, soluble powders, soluble granules, granules for broadcasting, suspoemulsion concentrates, natural compounds impregnated with active ingredient, synthetic substances impregnated with active ingredient, fertilizers and also microencapsulations in polymeric substances.

The active ingredients can be applied as such, in the form of their formulations or the use forms prepared therefrom, such as ready-to-use solutions, emulsions, water- or oil-based suspensions, powders, wettable powders, pastes, soluble powders, dusts, soluble granules, granules for broadcasting, suspoemulsion concentrates, natural products impregnated with active ingredient, synthetic materials impregnated with active ingredient, fertilizers and also microencapsulations in polymeric substances. Application is carried out in a customary manner, for example by watering, spraying, atomizing, broadcasting, dusting, foaming, spreading, etc. It is also possible to apply the active ingredients by the ultra-low volume method, or to inject the active ingredient preparation or the active ingredient itself into the soil. It is also possible to treat the seed of the plants.

The formulations mentioned can be prepared in a manner known per se, for example by mixing the active ingredients with at least one customary extender, solvent or diluent, emulsifier, dispersant and/or binder or fixing agent, wetting agent, a water repellent, if appropriate siccatives and UV stabilizers and if appropriate dyes and pigments, antifoams, preservatives, secondary thickeners, stickers, gibberellins and also other processing auxiliaries.

The inventive compositions include not only formulations which are already ready for use and can be applied with a suitable apparatus to the plant or the seed, but also commercial concentrates which have to be diluted with water prior to use.

The inventive active ingredients may be present as such or in their (commercial) formulations and in the use forms prepared from these formulations as a mixture with other (known) active ingredients, such as insecticides, attractants, sterilants, bactericides, acaricides, nematicides, fungicides, growth regulators, herbicides, fertilizers, safeners and/or semiochemicals.

The auxiliaries used may be those substances which are suitable for imparting particular properties to the composition itself and/or to preparations derived therefrom (for example spray liquors, seed dressings), such as certain technical properties and/or also particular biological properties. Typical auxiliaries include: extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

Liquefied gaseous extenders or carriers are understood to mean liquids which are gaseous at standard temperature and under standard pressure, for example aerosol propellants such as halohydrocarbons, or else butane, propane, nitrogen and carbon dioxide.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

If the extender used is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

The inventive compositions may additionally comprise further components, for example surfactants. Useful surfactants include emulsifiers and/or foam formers, dispersants or wetting agents with ionic or nonionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is required if one of the active ingredients and/or one of the inert carriers is insoluble in water and when the application is effected in water. The proportion of surfactants is between 5 and 40 percent by weight of the inventive composition.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Other possible additives are perfumes, mineral or vegetable oils which have optionally been modified, waxes and nutrients (including trace nutrients), such as salts of iron, manganese, boron, copper, cobalt, molybdenum and zinc.

Stabilizers such as low-temperature stabilizers, preservatives, antioxidants, light stabilizers or other compositions which improve chemical and/or physical stability may also be present.

If appropriate, other additional components may also be present, for example protective colloids, binders, adhesives, thickeners, thixotropic substances, penetrants, stabilizers, sequestrants, complexing agents. In general, the active ingredients can be combined with any solid or liquid additive customarily used for formulation purposes.

The formulations generally contain between 0.05 and 99% by weight, 0.01 and 98% by weight, preferably between 0.1 and 95% by weight and more preferably between 0.5 and 90% of active ingredient, most preferably between 10 and 70 percent by weight.

The formulations described above can be used in an inventive method for controlling unwanted microorganisms, in which the inventive bis(difluoromethyl)pyrazole derivatives are applied to the microorganisms and/or in their habitat.

The inventive active ingredients can also be used, as such or in their formulations, in a mixture with known fungicides, bactericides, acaricides, nematicides or insecticides, in order thus to broaden, for example, the activity spectrum or to prevent development of resistance.

Useful mixing partners include, for example, known fungicides, insecticides, acaricides, nematicides or else bactericides (see also Pesticide Manual, 14th ed.).

A mixture with other known active ingredients, such as herbicides, or with fertilizers and growth regulators, safeners and/or semiochemicals is also possible.

The compounds are applied in a customary manner appropriate for the use forms.

The invention also includes a method for treating seed.

A further aspect of the present invention relates in particular to seed treated with at least one of the inventive bis(difluoromethyl)pyrazole derivatives. The inventive seeds are used in methods for the protection of seed from phytopathogenic harmful fungi. In these methods, seed treated with at least one inventive active ingredient is used.

The inventive active ingredients or compositions are also suitable for treating seed. A large part of the damage to crop plants caused by harmful organisms is triggered by the infection of the seed during storage or after sowing, and also during and after germination of the plant. This phase is particularly critical since the roots and shoots of the growing plant are particularly sensitive, and even only minor damage may result in the death of the plant. There is therefore great interest in protecting the seed and the germinating plant by using appropriate compositions.

The control of phytopathogenic harmful fungi by treating the seed of plants has been known for a long time and is the subject of constant improvements. However, the treatment of seed gives rise to a series of problems which cannot always be solved in a satisfactory manner. Thus, it is desirable to develop methods for protecting the seed and the germinating plant which dispense with, or at least reduce considerably, the additional application of crop protection compositions after sowing or after emergence of the plants. It is also desirable to optimize the amount of active ingredient used in such a way as to provide optimum protection for the seed and the germinating plant from attack by phytopathogenic fungi, but without damaging the plant itself by the active ingredient employed. In particular, methods for the treatment of seed should also take into consideration the intrinsic fungicidal properties of transgenic plants in order to achieve optimum protection of the seed and the germinating plant with a minimum of crop protection compositions being employed.

The present invention therefore also relates to a method for protecting seed and germinating plants from attack by animal pests and/or phytopathogenic harmful fungi by treating the seed with an inventive composition. The invention also relates to the use of the inventive compositions for treating seed for protection of the seed and of the germinating plant against phytopathogenic fungi. The invention further relates to seed which has been treated with an inventive composition for protection from phytopathogenic fungi.

The control of animal pests and/or phytopathogenic harmful fungi which damage plants post-emergence is effected primarily by treating the soil and the above-ground parts of plants with crop protection compositions. Owing to the concerns regarding a possible impact of the crop protection compositions on the environment and the health of humans and animals, there are efforts to reduce the amount of active ingredients applied.

One of the advantages of the present invention is that, because of the particular systemic properties of the inventive compositions, treatment of the seed with these compositions protects not only the seed itself but also the resulting plants after emergence from animal pests and/or phytopathogenic harmful fungi. In this manner, the immediate treatment of the crop at the time of sowing or shortly thereafter can be dispensed with.

It is also considered to be advantageous that the inventive active ingredients or compositions can be used especially also for transgenic seed where the plant growing from this seed is capable of expressing a protein which acts against pests. By treating such seed with the inventive active ingredients or compositions, even the expression of the insecticidal protein, for example, may control certain pests. Surprisingly, a further synergistic effect may be observed here, which additionally increases the effectiveness of the protection against attack by pests.

The inventive compositions are suitable for protecting seed of any plant variety which is employed in agriculture, in the greenhouse, in forests or in horticulture. In particular, the seed is that of cereals (such as wheat, barley, rye, millet and oats), maize, cotton, soybeans, rice, potatoes, sunflowers, beans, coffee, beets (for example sugarbeets and fodder beets), peanuts, vegetables (such as tomatoes, cucumbers, onions and lettuce), lawns and ornamental plants. The treatment of the seed of cereals (such as wheat, barley, rye and oats), maize and rice is of particular importance.

As also described below, the treatment of transgenic seed with the inventive active ingredients or compositions is of particular importance. This relates to the seed of plants containing at least one heterologous gene which enables the expression of a polypeptide or protein having insecticidal properties. The heterologous gene in transgenic seed may originate, for example, from microorganisms of the *Bacillus, Rhizobium, Pseudomonas, Serratia, Trichoderma, Clavibacter, Glomus* or *Gliocladium* species. This heterologous gene preferably originates from *Bacillus* sp., the gene product being effective against the European corn borer and/or the Western corn rootworm. The heterologous gene more preferably originates from *Bacillus thuringiensis*.

In the context of the present invention, the inventive composition is applied to the seed alone or in a suitable formulation. The seed is preferably treated in a state in which it is stable enough that no damage occurs during treatment. In general, the seed may be treated at any time between harvest and sowing. The seed typically used has been separated from the plant and freed from cobs, shells, stalks, coats, hairs or the flesh of the fruits. For example, it is possible to use seed which has been harvested, cleaned and dried to a moisture content of less than 15% by weight. Alternatively, it is also possible to use seed which, after drying, has been treated, for example, with water and then dried again.

When treating the seed, it must generally be ensured that the amount of the inventive composition and/or of further additives applied to the seed is selected such that the germination of the seed is not impaired, and the resulting plant is not damaged. This must be borne in mind in particular in the case of active ingredients which can exhibit phytotoxic effects at certain application rates.

The inventive compositions can be applied directly, i.e. without containing any other components and without having been diluted. In general, it is preferable to apply the compositions to the seed in the form of a suitable formulation. Suitable formulations and methods for treating seed are known to the person skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active ingredients which can be used in accordance with the invention can be converted to the customary seed-dressing formulations, such as solutions, emulsions, suspensions, powders, foams, slurries or other coating compositions for seed, and also ULV formulations.

These formulations are prepared in a known manner, by mixing the active ingredients or active ingredient combinations with customary additives, for example customary extenders and also solvents or diluents, dyes, wetting agents, dispersants, emulsifiers, antifoams, preservatives, secondary thickeners, adhesives, gibberellins, and also water.

Dyes which may be present in the seed-dressing formulations usable in accordance with the invention are all dyes which are customary for such purposes. In this context, it is possible to use either pigments, which are sparingly soluble in water, or dyes, which are soluble in water. Examples include the dyes known by the names Rhodamine B, C.I. Pigment Red 112 and C.I. Solvent Red 1.

Suitable wetting agents which may be present in the seed-dressing formulations usable in accordance with the invention are all substances which promote wetting and which are conventional in the formulation of active agrochemical ingredients. Preference is given to using alkylnaphthalenesulphonates, such as diisopropyl- or diisobutylnaphthalenesulphonates.

Useful dispersants and/or emulsifies which may be present in the seed-dressing formulations usable in accordance with the invention are all nonionic, anionic and cationic dispersants conventional in the formulation of active agrochemical ingredients. Preference is given to using nonionic or anionic dispersants or mixtures of nonionic or anionic dispersants. Suitable nonionic dispersants include especially ethylene oxide/propylene oxide block polymers, alkylphenol polyglycol ethers and tristryrylphenol polyglycol ethers, and the phosphated or sulphated derivatives thereof. Suitable anionic dispersants are especially lignosulphonates, polyacrylic acid salts and arylsulphonate/formaldehyde condensates.

Antifoams which may be present in the seed-dressing formulations usable in accordance with the invention are all foam-inhibiting substances conventional in the formulation of active agrochemical ingredients. Silicone antifoams and magnesium stearate can preferably be used.

Preservatives which may be present in the seed-dressing formulations usable in accordance with the invention are all substances which can be used for such purposes in agrochemical compositions. Examples include dichlorophene and benzyl alcohol hemiformal.

Secondary thickeners which may be present in the seed-dressing formulations usable in accordance with the invention are all substances useful for such purposes in agrochemical compositions. Preference is given to cellulose derivatives, acrylic acid derivatives, xanthan, modified clays and finely divided silica.

Adhesives which may be present in the seed-dressing formulations usable in accordance with the invention are all customary binders usable in seed-dressing products. Preference is given to polyvinylpyrrolidone, polyvinyl acetate, polyvinyl alcohol and tylose.

The gibberellins which may be present in the seed-dressing formulations usable in accordance with the invention may preferably be gibberellins A1, A3 (=gibberellic acid), A4 and A7; particular preference is given to using gibberellic acid. The gibberellins are known (cf. R. Wegler "Chemie der Pflanzenschutz-und Schädlingsbekämpfungsmittel" [Chemistry of Crop Protection Compositions and Pesticide Compositions], vol. 2, Springer Verlag, 1970, p. 401-412).

The seed-dressing formulations usable in accordance with the invention can be used for the treatment of a wide range of seed, either directly or after preceding dilution with water. Thus, the concentrates or the preparations obtainable therefrom by dilution with water can be used to dress the seed of cereals, such as wheat, barley, rye, oats and triticale, and also the seed of maize, rice, oilseed rape, peas, beans, cotton, sunflowers and beets, or else vegetable seed of a wide variety of types. The seed-dressing formulations usable in accordance with the invention or the dilute preparations thereof can also be used to dress seed of transgenic plants. In this context, additional synergistic effects may also occur in interaction with the substances formed by expression.

For treatment of seed with the seed-dressing formulations usable in accordance with the invention or the formulations prepared therefrom by addition of water, useful mixing equipment is all of that usable conventionally for the seed-dressing operation. Specifically, the procedure during the seed-dressing operation is to place the seed into a mixer, add the specific desired amount of seed-dressing formulations, either as such or after preceding dilution with water, and mix until the formulation is distributed homogeneously on the seed. If appropriate, this is followed by a drying process.

The application rate of the seed-dressing formulations usable in accordance with the invention may be varied within a relatively wide range. It depends on the particular content of the active ingredients in the formulations and on the seed. The application rates of active ingredient combination are generally between 0.001 and 50 g per kilogram of seed, preferably between 0.01 and 15 g per kilogram of seed.

In addition, the inventive compounds of the formula (I) also have very good antimycotic activity. They have a very broad antimycotic activity spectrum, in particular against dermatophytes and yeasts, moulds and diphasic fungi (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes, Microsporon* species, such as *Microsporon canis* and *audouinii*. The list of these fungi by no means constitutes a restriction in the mycotic spectrum covered, and is merely of illustrative character.

The inventive active ingredients of the formula (I) can therefore be used both in medical and in non-medical applications.

The active ingredients can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is also possible to apply the active ingredients by the ultra-low volume method, or to inject the active ingredient preparation or the active ingredient itself into the soil. It is also possible to treat the seed of the plants.

When the inventive active ingredients are used as fungicides, the application rates can be varied within a relatively wide range, depending on the kind of application. The application rate of the inventive active ingredients is when treating plant parts, for example leaves: from 0.1 to 10 000 g/ha, preferably from 10 to 1000 g/ha, more preferably from 50 to 300 g/ha (in the case of application by watering or dripping, it is even possible to reduce the application rate, particularly when inert substrates such as rockwool or perlite are used);

when treating seed: from 2 to 200 g per 100 kg of seed, preferably from 3 to 150 g per 100 kg of seed, more preferably from 2.5 to 25 g per 100 kg of seed, most preferably from 2.5 to 12.5 g per 100 kg of seed:

when treating the soil: from 0.1 to 10 000 g/ha, preferably from 1 to 5000 g/ha.

These application rates are mentioned merely by way of example and are not limiting in the context of the invention.

The inventive active ingredients are employed in the veterinary sector and in animal husbandry in a known manner by enteral administration in the form of, for example, tablets, capsules, portions, drenches, granules, pastes, boluses, the feed-through process and suppositories, by parenteral administration, for example by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active ingredient, such as collars, ear marks, tail marks, limb bands, halters, marking devices and the like.

When used for livestock, poultry, domestic animals and the like, the active ingredients of the formula (I) can be used as formulations (for example powders, emulsions, flowables) comprising the active ingredients in an amount of 1 to 80% by weight, either directly or after 100- to 10 000-fold dilution, or they may be used as a chemical bath.

The ready-to-use compositions may also comprise other insecticides if appropriate, and also one or more fungicides if appropriate.

With respect to possible additional partners for mixing, reference is made to the insecticides and fungicides mentioned above.

The inventive compounds can additionally be employed for anti-fouling protection of objects which come into contact with saltwater or brackish water, such as hulls, screens, nets, buildings, moorings and signalling systems in particular.

In addition, the inventive compounds can be used alone or in combinations with other active ingredients as anti-fouling compositions.

The inventive treatment method can be used for the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and, when introduced in the nuclear, chloroplastic or mitochondrial genome, imparts new or improved agronomic or other properties to the transformed plant by expressing a protein or polypeptide of interest or by down-regulating or silencing (an)other gene(s) present in the plant (for example by means of antisense technology, cosuppression technology or RNAi technology [RNA interference]). A heterologous gene present in the genome is also called a transgene. A transgene defined by its specific location in the plant genome is called a transformation or transgenic event.

Depending on the plant species or plant varieties, their location and growth conditions (soils, climate, vegetation period, diet), the inventive treatment may also result in super-additive ("synergistic") effects. For example, the following are possible effects exceeding the effects which were actually to be expected: reduced application rates and/or a widening of the activity spectrum and/or an increase in the activity of the active ingredients and compositions which can be used in accordance with the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processability of the harvested products.

At certain application rates, the inventive active ingredient combinations may also have a strengthening effect on plants. They are therefore suitable for mobilizing the defence system of the plant against attack by unwanted phytopathogenic fungi and/or microorganisms and/or viruses. This may in some cases be one of the reasons for the enhanced activity of the inventive combinations, for example against fungi. Plant-strengthening (resistance-inducing) substances should be understood in the present context also to mean those substances or substance combinations which are capable of stimulating the defence system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are understood to mean phytopathogenic fungi, bacteria and viruses. The inventive substances can therefore be employed for protection of plants from attack by the abovementioned pathogens within a certain period of time after the treatment. The period within which protection is achieved generally lasts for from 1 to 10 days, preferably 1 to 7 days, after the treatment of the plants with the active ingredients.

Plants and plant varieties which are preferably treated in accordance with the invention include all plants which have genetic material which imparts particularly advantageous useful traits to these plants (whether obtained by breeding and/or biotechnology).

Plants and plant varieties which are likewise preferably treated in accordance with the invention are resistant to one or more biotic stress factors, i.e. said plants have an improved defence against animal and microbial pests, such as nematodes, insects, mites, phytopathogenic fungi, bacteria, viruses and/or viroids.

Plants and plant varieties which can likewise be treated in accordance with the invention are those plants which are resistant to one or more abiotic stress factors. Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or lack of shade.

Plants and plant varieties which can likewise be treated in accordance with the invention are those plants characterized by enhanced yield characteristics. Enhanced yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can also be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants which can be treated in accordance with the invention are hybrid plants that already express the characteristics of heterosis, or hybrid vigour, which results in generally higher yield, increased vigour, better health and better resistance towards biotic and abiotic stress factors. Such plants are typically obtained by crossing an inbred male-sterile parent line (the female parent) with another inbred male-fertile parent line (the male parent). Hybrid seed is typically harvested from the male-sterile plants and sold to growers. Male-sterile plants can sometimes (for example in maize) be produced by detasseling (i.e. mechanical removal of the male reproductive organs or male flowers); however, it is more typical for male sterility to be the result of genetic determinants in the plant genome. In that case, and especially when seed is the desired product to be harvested from the hybrid plants, it is typically favourable to ensure that male fertility in hybrid plants which contain the genetic determinants responsible for male sterility is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species. However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar.

Plants or plant varieties (obtained by plant biotechnology methods such as genetic engineering) which may be treated in accordance with the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes encoding a petunia EPSPS, a tomato EPSPS, or an *Eleusine* EPSPS. It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyl transferase enzyme. Glyphosate-tolerant plants can also be obtained by selecting plants containing naturally-occurring mutations of the abovementioned genes.

Other herbicide-resistant plants are for example plants which have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species for example). Plants expressing an exogenous phosphinothricin acetyltransferase have been described.

Further herbicide-tolerant plants are also plants that have been made tolerant to the herbicides inhibiting the enzyme hydroxyphenylpyruvatedioxygenase (HPPD). Hydroxyphenylpyruvatedioxygenases are enzymes that catalyse the reaction in which para, hydroxyphenylpyruvate (HPP) is transformed into homogentisate. Plants tolerant to HPPD inhibitors can be transformed with a gene encoding a naturally occurring resistant HPPD enzyme, or a gene encoding a mutated HPPD enzyme. Tolerance to HPPD-inhibitors can also be obtained by transforming plants with genes encoding certain enzymes enabling the formation of homogentisate despite the inhibition of the native HPPD enzyme by the HPPD-inhibitor. Tolerance of plants to HPPD inhibitors can also be improved by transforming plants with a gene encoding an enzyme prephenate dehydrogenase in addition to a gene encoding an HPPD-tolerant enzyme.

Further herbicide-resistant plants are plants that have been made tolerant to acetolactate synthase (ALS) inhibitors. Known ALS inhibitors include, for example, sulphonylurea, imidazolinone, triazolopyrimidines, pyrimidinyl oxy(thio)benzoates, and/or sulphonylaminocarbonyltriazolinone herbicides. Different mutations in the ALS enzyme (also known as acetohydroxyacid synthase, AHAS) are known to confer tolerance to different herbicides and groups of herbicides. The production of sulphonylurea-tolerant plants and imidazolinone-tolerant plants has been described in the international publication WO 1996/033270. Further sulphonylurea- and imidazolinone-tolerant plants have also been described, for example in WO 2007/024782.

Other plants tolerant to imidazolinone and/or sulphonylurea can be obtained by induced mutagenesis, by selection in cell cultures in the presence of the herbicide or by mutation breeding.

Plants or plant varieties (obtained by plant biotechnology methods such as genetic engineering) which may also be treated in accordance with the invention are insect-resistant transgenic plants, i.e. plants made resistant to attack by certain target insects. Such plants can be obtained by genetic transformation, or by selection of plants containing a mutation imparting such insect resistance.

In the present context, the term "insect-resistant transgenic plant" includes any plant containing at least one transgene comprising a coding sequence encoding:

1) an insecticidal crystal protein from *Bacillus thuringiensis* or an insecticidal portion thereof, such as the insecticidal crystal proteins listed online at: lifesci.sussex.ac.uk/Home/Neil_Crickmore/Bt/, or insecticidal portions thereof, for example proteins of the Cry protein classes Cry1Ab, Cry1Ac, Cry1F, Cry2Ab, Cry3Ae or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins; or
3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A.105 protein produced by maize event MON98034 (WO 2007/027777); or
4) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in maize events MON863 or MON88017, or the Cry3A protein in maize event MIR 604;
5) an insecticidal secreted protein from *Bacillus thuringiensis* or *Bacillus cereus*, or an insecticidal portion thereof, such as the vegetative insecticidal proteins (VIP) listed at: lifesci.sussex.ac.uk/Home/Neil_Crickmore/Bt/vip.html, for example proteins from the VIP3Aa protein class; or
6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins;
7) a hybrid insecticidal protein comprising parts from different secreted proteins from *Bacillus thuringiensis* or *Bacillus cereus*, such as a hybrid of the proteins in 1) above or a hybrid of the proteins in 2) above; or
8) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT 102.

Of course, insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants, by using different proteins insecticidal to the same target insect species but having a different mode of action, such as binding to different receptor binding sites in the insect.

Plants or plant varieties (obtained by plant biotechnology methods such as genetic engineering) which may also be treated in accordance with the invention are tolerant to abiotic stress factors. Such plants can be obtained by genetic transformation, or by selection of plants containing a mutation imparting such stress resistance. Particularly useful stress-tolerant plants include the following:
a. plants which contain a transgene capable of reducing the expression and/or the activity of the poly(ADP-ribose) polymerase (PARP) gene in the plant cells or plants;
b. plants which contain a stress tolerance-enhancing transgene capable of reducing the expression and/or the activity of the PARG-encoding genes of the plants or plant cells;
c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant varieties (obtained by plant biotechnology methods such as genetic engineering) which may also be treated in accordance with the invention show altered quantity, quality and/or storage stability of the harvested product and/or altered properties of specific ingredients of the harvested product such as, for example:
1) Transgenic plants which synthesize a modified starch which is altered with respect to its chemophysical traits, in particular the amylose content or the amylose/amylopectin ratio, the degree of branching, the average chain length, the distribution of the side chains, the viscosity behaviour, the gel resistance, the grain size and/or grain morphology of the starch in comparison to the synthesized starch in wild-type plant cells or plants, such that this modified starch is better suited for certain applications.
2) Transgenic plants which synthesize non-starch carbohydrate polymers or which synthesize non-starch carbohydrate polymers with altered properties in comparison to wild-type plants without genetic modification. Examples are plants which produce polyfructose, especially of the inulin and levan type, plants which produce alpha-1,4-glucans, plants which produce alpha-1,6-branched alpha-1,4-glucans, and plants producing alternan.
3) Transgenic plants which produce hyaluronan.

Plants or plant varieties (obtained by plant biotechnology methods such as genetic engineering) which may also be treated in accordance with the invention are plants, such as cotton plants, with altered fibre characteristics. Such plants can be obtained by genetic transformation, or by selection of plants containing a mutation imparting such altered fibre characteristics and include:
a) plants, such as cotton plants, which contain an altered form of cellulose synthase genes;
b) plants, such as cotton plants, which contain an altered form of rsw2 or rsw3 homologous nucleic acids;
c) plants, such as cotton plants, with an increased expression of sucrose phosphate synthase;
d) plants, such as cotton plants, with an increased expression of sucrose synthase;
e) plants, such as cotton plants, wherein the timing of the plasmodesmatal gating at the basis of the fibre cell is altered, for example through downregulation of fibre-selective β-1,3-glucanase;
f) plants, such as cotton plants, which have fibres with altered reactivity, for example through the expression of the N-acetylglucosaminetransferase gene including nodC and chitin synthase genes.

Plants or plant cultivars (obtained by plant biotechnology methods such as genetic engineering) which may also be treated in accordance with the invention are plants, such as oilseed rape or related *Brassica* plants, with altered oil profile characteristics. Such plants can be obtained by genetic transformation or by selection of plants containing a mutation imparting such altered oil characteristics and include:
a) plants, such as oilseed rape plants, which produce oil having a high oleic acid content;
b) plants, such as oilseed rape plants, which produce oil having a low linolenic acid content;
c) plants, such as oilseed rape plants, which produce oil having a low level of saturated fatty acids.

Particularly useful transgenic plants which may be treated in accordance with the invention are plants which comprise one or more genes which encode one or more toxins and are the transgenic plants available under the following trade names: YIELD GARD® (for example maize, cotton, soya beans), KnockOut® (for example maize), BiteGard® (for example maize), BT-Xtra® (for example maize), StarLink® (for example maize), Bollgard® (cotton), Nucotn® (cotton), Nucotn® 33B® (cotton), NatureGard® (for example maize), Protecta® and NewLeaf® (potato). Examples of herbicide-tolerant plants which may be mentioned are maize varieties, cotton varieties and soya bean varieties which are available under the following trade names: Roundup Ready® (tolerance to glyphosate, for example maize, cotton, soya beans), Liberty Link® (tolerance to phosphinothricin, for example oilseed rape), IMI® (tolerance to imidazolinone) and SCS® (tolerance to sulphonylurea, for example maize). Herbicide-resistant plants (plants bred in a conventional manner for herbicide tolerance) which may be mentioned include the varieties sold under the name Clearfield® (for example maize).

Particularly useful transgenic plants which may be treated in accordance with the invention are plants containing transformation events, or a combination of transformation events, and that are listed for example in the databases for various national or regional regulatory agencies (see for example gmoinfo.jrc.it/gmp_browse.aspx and agbios.com/dbase.php)

The plants listed can be treated in accordance with the invention in a particularly advantageous manner with the compounds of the general formula (I) and/or the inventive active ingredient mixtures. The preferred ranges stated above for the active ingredients or mixtures also apply to the treatment of these plants. Particular emphasis is given to the treatment of plants with the compounds or mixtures specifically mentioned in the present text.

The inventive active ingredients or compositions can thus be used to protect plants from attack by the pathogens mentioned for a certain period after treatment. The period for which protection is provided generally lasts for 1 to 28 days, preferably for 1 to 14 days, more preferably for 1 to 10 days, most preferably for 1 to 7 days after the treatment of the plants with the active ingredients, or for up to 200 days after a seed treatment.

The preparation and the use of the inventive active ingredients of the formula (I) are illustrated by the examples which follow. However, the invention is not limited to these examples.

General note: Unless stated otherwise, all chromatographic purification and separation steps were carried out on silica gel and with a solvent gradient of 0:100 ethyl acetate/cyclohexane to 100:0 ethyl acetate/hexane.

Preparation of Compounds of the Formula (I)

2-[3,5-Bis(difluoromethyl)-1H-pyrazol-1-yl]-1-{4-fluoro-4-[4-(5-phenyl-4,5-dihydro-1,2-oxazol-3-yl)-1,3-thiazol-2-yl]piperidin-1-yl}ethanone (I-5)

Process A tert-Butyl 4-(4-bromo-1,3-thiazol-2-yl)-4-hydroxypiperidine-1-carboxylate (IV-1)

To a solution of 2,4-dibromo-1,3-thiazole (8.8 g) in dichloromethane (180 ml) was added dropwise, at −78° C. under argon, n-butyllithium (1.6 M in tetrahydrofuran, 25 ml). The reaction mixture was stirred at −78° C. for 20 minutes and then tert-butyl 4-oxopiperidine-1-carboxylate was added. The mixture was stirred at room temperature for 30 minutes. The reaction mixture was subsequently admixed with saturated ammonium chloride solution at −30° C. and the aqueous phase was removed. After the aqueous phase had been extracted with dichloromethane, the combined organic phases were dried over sodium sulphate and concentrated under reduced pressure. The residue was purified by chromatography. This gave tert-butyl 4-(4-bromo-1,3-thiazol-2-yl)-4-hydroxypiperidine-1-carboxylate (15.3 g).

$^1$H NMR (DMSO-d$_6$): $\delta_{ppm}$: 1.43 (s, 9H), 1.70 (d, 2H), 1.88 (ddd, 2H), 3.11 (bs, 2H), 3.83 (d, 2H), 6.31 (s, 1H), 7.72 (s, 1H)

log P (HCOOH): 2.74

MS (ESI): 363 and 365 ([M+H]$^+$)

Process B tert-Butyl 4-(4-bromo-1,3-thiazol-2-yl)-4-fluoropiperidine-1-carboxylate (V-1)

tert-Butyl 4-(4-bromo-1,3-thiazol-2-yl)-4-hydroxypiperidine-1-carboxylate (17.7 g) was initially charged under argon at 0° C. in dichloromethane in a PE flask, and diethylaminosulphur trifluoride (DAST) (7.08 ml) was added dropwise. The cooling was removed. After stirring overnight, saturated aqueous sodium hydrogencarbonate solution was added and the mixture was extracted with dichloromethane. The organic extracts were dried over sodium sulphate and concentrated under reduced pressure. The residue was purified by chromatography. This gave tert-butyl 4-(4-bromo-1,3-thiazol-2-yl)-4-fluoropiperidine-1-carboxylate (18.0 g).

$^1$H NMR (DMSO-d$_6$): $\delta_{ppm}$: 1.42 (s, 9H), 2.13-2.00 (m, 4H), 3.14 (bs, 2H), 3.95-3.87 (m, 2H), 7.95 (s, 1H)

log P (HCOOH): 3.94

MS (ESI): 309 and 311 ([M-C(CH$_3$)$_3$+2H]$^+$)

Process C tert-Butyl 4-fluoro-4-(4-formyl-1,3-thiazol-2-yl)piperidine-1-carboxylate (VI-1)

To a solution of tert-butyl 4-(4-bromo-1,3-thiazol-2-yl)-4-fluoropiperidine-1-carboxylate (245 mg) in dichloromethane (5 ml) was added dropwise, at −78° C., n-butyllithium (1.6 M in tetrahydrofuran, 0.42 ml). Ater 20 min, N,N-dimethylformamide (0.16 ml) was added dropwise. After stirring at −78° C. for 30 minutes, saturated ammonium chloride solution was added, and the mixture was extracted with dichloromethane. The organic extracts were dried over sodium sulphate and concentrated under reduced pressure. The residue was purified by chromatography. This gave tert-butyl 4-fluoro-4-(4-formyl-1,3-thiazol-2-yl)piperidine-1-carboxylate (75 mg).

$^1$H NMR (DMSO-d$_6$): $\delta_{ppm}$: 1.43 (s, 9H), 2.18-2.04 (m, 4H), 3.17 (bs, 2H), 3.97-3.89 (m, 2H), 8.80 (s, 1H), 9.92 (s, 1H)

log P (HCOOH): 2.80

MS (ESI): 259 ([M-C(CH$_3$)$_3$+2 H]$^+$)

Processes D and E tert-Butyl 4-fluoro-4-{4-[(E/Z)-(hydroxyimino)methyl]-1,3-thiazol-2-yl}piperidine-1-carboxylate To a solution of tert-butyl 4-fluoro-4-(4-formyl-1,3-thiazol-2-yl)piperidine-1-carboxylate (3.49 g) in ethanol (50 ml) was added dropwise hydroxylamine (50% in water, 0.81 ml)

at room temperature. The reaction mixture was stirred at 60° C. for 1 hour, then the solvent was removed under reduced pressure. This gave tert-butyl 4-fluoro-4-{4-[(E/Z)-(hydroxyimino)methyl]-1,3-thiazol-2-yl}piperidine-1-carboxylate (3.49 g).

$^1$H NMR (DMSO-d$_6$): δ$_{ppm}$: 1.42 (s, 9H), 2.17-2.03 (m, 4H), 3.16 (bs, 2H), 3.94-3.86 (m, 2H), 7.96 (s, 1H), 8.17 (s, 1H)

log P (HCOOH): 2.53

MS (ESI): 230 ([M-COOC(CH$_3$)$_3$+2H]$^+$)

tert-Butyl 4-fluoro-4-[4-(5-phenyl-4,5-dihydro-1,2-oxazol-3-yl)-1,3-thiazol-2-yl]piperidine-1-carboxylate (X-a-1)

To a solution of tert-butyl 4-fluoro-4-{4-[(E/Z)-(hydroxyimino)methyl]-1,3-thiazol-2-yl}piperidine-1-carboxylate (500 mg) in tetrahydrofuran (5 ml) was added dropwise, at room temperature, styrene (0.21 ml), followed by hypochlorite (13% in water). After stirring at room temperature for 4 hours, the solvent was removed under reduced pressure. The residue was admixed with dichloromethane and water, and extracted with dichloromethane. The organic extracts were dried over sodium sulphate and concentrated under reduced pressure. The residue was purified by chromatography. This gave tert-butyl 4-fluoro-4-[4-(5-phenyl-4,5-dihydro-1,2-oxazol-3-yl)-1,3-thiazol-2-yl]piperidine-1-carboxylate (380 mg).

$^1$H NMR (DMSO-d$_6$): δ$_{ppm}$: 1.42 (s, 9H), 2.14-2.07 (m, 4H), 3.15 (bs, 2H), 3.38 (dd, 1H), 3.89 (dd, 1H), 3.93 (bs, 2H), 5.75 (dd, 1H), 7.34 (m, 1H), 7.42-7.39 (m, 4H), 8.21 (s, 1H)

log P (HCOOH): 4.28

MS (ESI): 332 ([M-COOC(CH$_3$)$_3$+2H]$^+$)

Process G

4-Fluoro-4-[4-(5-phenyl-4,5-dihydro-1,2-oxazol-3-yl)-1,3-thiazol-2-yl]piperidinium chloride (XII-1)

To a solution of tert-butyl 4-fluoro-4-[4-(5-phenyl-4,5-dihydro-1,2-oxazol-3-yl)-1,3-thiazol-2-yl]piperidine-1-carboxylate (380 mg) was added dropwise, at 0° C., a 4 molar solution of hydrochloric acid in 1,4-dioxane. The reaction mixture was stirred at 0° C. and then gradually warmed to room temperature. After stirring overnight, the solvent and excess hydrogen chloride were removed. This gave 4-fluoro-4-[4-(5-phenyl-4,5-dihydro-1,2-oxazol-3-yl)-1,3-thiazol-2-yl]piperidinium chloride (374 mg).

$^1$H NMR (DMSO-d$_6$): δ$_{ppm}$: 2.58-2.30 (m, 4H), 3.23-3.14 (m, 2H), 3.38 (dd, 1H), 3.56 (s, 2H), 3.90 (dd, 1H), 5.76 (dd, 1H), 7.42-7.33 (m, 5H), 8.25 (s, 1H), 9.08 (bs, 1H), 9.24 (bs, 1H)

log P (HCOOH): 1.17

MS (ESI): 332 ([M-Cl]$^+$)

Process H

2-[3,5-Bis(difluoromethyl)-1H-pyrazol-1-yl]-1-{4-fluoro-4-[4-(5-phenyl-4,5-dihydro-1,2-oxazol-3-yl)-1,3-thiazol-2-yl]piperidin-1-yl}ethanone (I-5)

To a solution of [3,5-bis(difluoromethyl)-1H-pyrazol-1-yl]acetic acid (230 mg) in dichloromethane (5 ml) were added oxalyl chloride (387 mg) and one drop of N,N-dimethylformamide. The reaction mixture was stirred at room temperature overnight. After removing the solvent under reduced pressure, the residue was then dissolved in dichloromethane (5 ml), and a solution of 4-fluoro-4-[4-(5-phenyl-4,5-dihydro-1,2-oxazol-3-yl)-1,3-thiazol-2-yl]piperidinium chloride (374 mg) and of Hünig's base (394 mg) in dichloromethane (5 ml) was added dropwise at 0° C. The reaction mixture was stirred at room temperature for 3 hours. After addition of conc. ammonium chloride solution, the aqueous phase was removed and extracted with ethyl acetate. The combined organic phases were dried over sodium sulphate and concentrated under reduced pressure. The residue was purified by chromatography. This gave 2-[3,5-bis(difluoromethyl)-1H-pyrazol-1-yl]-1-{4-fluoro-4-[4-(5-phenyl-4,5-dihydro-1,2-oxazol-3-yl)-1,3-thiazol-2-yl]piperidin-1-yl}ethanone (250 mg).

$^1$H NMR (DMSO-d$_6$): δ$_{ppm}$: 2.45-2.05 (m, 4H), 3.11 (m, 1H), 3.38 (dd, 1H), 3.48 (m, 1H), 3.95-3.86 (m, 2H), 4.26 (m, 1H), 5.39 (d, 1H), 5.50 (d, 1H), 5.76 (dd, 1H), 6.91 (s, 1H), 7.03 (t, 1H), 7.18 (t, 1H), 7.42-7.33 (m, 5H), 8.22 (s, 1H)

log P (HCOOH): 3.41

MS (ESI): 540 ([M+H]$^+$)

1-(4-{4-[5-(2-acetylphenyl)-4,5-dihydro-1,2-oxazol-3-yl]-1,3-thiazol-2-yl}piperidin-1-yl)-2-[3,5-bis(difluoromethyl)-1H-pyrazol-1-yl]ethanone (I-7)

Processes D and E tert-Butyl 4-{4-[5-(2-acetylphenyl)-4,5-dihydro-1,2-oxazol-3-yl]-1,3-thiazol-2-yl}piperidine-1-carboxylate (X-a-2)

To a solution of tert-butyl 4-{4-[(Z/E)-(hydroxyimino)methyl]-1,3-thiazol-2-yl}piperidine-1-carboxylate (4.5 g) and 1-(2-vinylphenyl)ethanone (2.32 g) in ethyl acetate (70 ml) were added, at room temperature, potassium hydrogencarbonate (7.23 g) and N-chlorosuccinimide (2.31 g), and then three drops of water. The reaction mixture was stirred at 60° C. for 3 hours, then admixed with ethyl acetate and water and extracted with ethyl acetate. The organic extracts were dried over sodium sulphate and concentrated under reduced pressure. The residue was purified by chromatography. This gave tort-butyl 4-{4-[5-(2-acetylphenyl)-4,5-dihydro-1,2-oxazol-3-yl]-1,3-thiazol-2-yl}piperidine-1-carboxylate (4.64 g).

$^1$H NMR (DMSO-d$_6$): δ$_{ppm}$: 1.41 (s, 9H), 1.60-1.48 (m, 2H), 2.04-1.98 (m, 2H), 2.63 (s, 3H), 2.89 (bs, 2H), 3.13 (dd, 1H), 3.27-3.18 (m, 1H), 4.07-3.95 (m, 3H), 6.12 (dd, 1H), 7.48 (dd, 1H), 7.56 (d, 1H), 7.61 (dd, 1H), 7.98 (s, 1H), 8.00 (d, 1H)

Process G

1-(2-{3-[2-(Piperidin-4-yl)-1,3-thiazol-4-yl]-4,5-dihydro-1,2-oxazol-5-yl}phenyl)ethanone hydrochloride (XII-2)

To a solution of tort-butyl 4-{4-[5-(2-acetylphenyl)-4,5-dihydro-1,2-oxazol-3-yl]-1,3-thiazol-2-yl}piperidine-1-carboxylate (500 mg) in 1,4-dioxane (5 ml) was added dropwise, at 0° C., a 4 molar solution of hydrogen chloride in 1,4-dioxane (4.2 ml). The reaction mixture was stirred at 0° C. and then gradually warmed to room temperature. After stirring overnight, the solvent and excess hydrogen chloride were removed. This gave 1-(2-{3-[2-(piperidin-4-yl)-1,3-thiazol-4-yl]-4,5-dihydro-1,2-oxazol-5-yl}phenyl)ethanone hydrochloride (430 mg).

$^1$H NMR (DMSO-d$_6$): δ$_{ppm}$: 1.99-1.85 (m, 2H), 2.23-2.15 (m, 2H), 2.63 (s, 3H), 3.08-2.97 (m, 2H), 3.14 (dd, 1H), 3.43-3.30 (m, 3H), 4.00 (dd, 1H), 6.12 (dd, 1H), 7.98 (dd, 1H), 7.56 (d, 1H), 7.62 (dd, 1H), 8.00 (d, 1H), 8.03 (s, 1H), 8.75 (bs, 1H), 9.03 (bs, 1H)

log P (HCOOH): 0.96

MS (ESI): 358 ([M-Cl]$^+$)

Process H

1-(4-{4-[5-(2-Acetylphenyl)-4,5-dihydro-1,2-oxazol-3-yl]-1,3-thiazol-2-yl}piperidin-1-yl)-2-[3,5-bis(difluoromethyl)-1H-pyrazol-1-yl]ethanone (I-7)

Solution A: To a solution of [3,5-bis(difluoromethyl)-1H-pyrazol-1-yl]acetic acid (280 mg) in dichloromethane (10 ml) were added dropwise, at room temperature, one drop of N,N-dimethylformamide and oxalyl chloride (0.295 ml). After stirring at room temperature for two hours, the solvent was removed and the residue was dissolved again in dichloromethane (10 ml) (solution A).

To a solution of 1-(2-{3-[2-(piperidin-4-yl)-1,3-thiazol-4-yl]-4,5-dihydro-1,2-oxazol-5-yl}phenyl)ethanone hydrochloride (441 mg) in dichloromethane (5 ml) was added, at room temperature, diisopropylethylamine (588 ml). After 15 minutes, solution A was added dropwise. After stirring at room temperature overnight, the reaction was admixed with water and extracted with ethyl acetate. The organic extracts were dried over sodium sulphate and concentrated under reduced pressure. The residue was purified by chromatography. This gave 1-(4-{4-[5-(2-acetylphenyl)-4,5-dihydro-1,2-oxazol-3-yl]-1,3-thiazol-2-yl}piperidin-1-yl)-2-[3,5-bis(difluoromethyl)-1H-pyrazol-1-yl]ethanone (590 mg).

2-{3-[2-(1-{[3,5-Bis(difluoromethyl)-1H-pyrazol-1-yl]acetyl}piperidin-4-yl)-1,3-thiazol-4-yl]-4,5-dihydro-1,2-oxazol-5-yl}benzaldehyde (I-26)

Processes D and E tert-Butyl 4-{4-[5-(2-formylphenyl)-4,5-dihydro-1,2-oxazol-3-yl]-1,3-thiazol-2-yl}piperidine-1-carboxylate (X-a-3)

tert-Butyl 4-{4-[(Z/E)-(hydroxyimino)methyl]-1,3-thiazol-2-yl}piperidine-1-carboxylate (5.6 g) and 2-vinylbenzaldehyde (2.61 g) were reacted analogously to I-7 (Processes D and E). This gave tert-butyl 4-{4-[5-(2-formylphenyl)-4,5-dihydro-1,2-oxazol-3-yl]-1,3-thiazol-2-yl}piperidine-1-carboxylate (5.69 g).

$^1$H NMR (DMSO-d$_6$): $\delta_{ppm}$: 1.41 (s, 9H), 1.60-1.48 (m, 2H), 2.04-1.98 (m, 2H), 2.89 (bs, 2H), 3.28-3.15 (m, 2H), 4.07-3.95 (m, 3H), 6.42 (dd, 1H), 7.64-7.57 (m, 2H), 7.72 (dd, 1H), 7.99 (s, 1H), 8.03 (d, 1H), 10.18 (s, 1H)

log P (HCOOH): 3.76

MS (ESI): 342 ([M-COOC(CH$_3$)$_3$+2H]$^+$)

Process G

2-{3-[2-(Piperidin-4-yl)-1,3-thiazol-4-yl]-4,5-dihydro-1,2-oxazol-5-yl}benzaldehyde hydrochloride (XII-3)

tert-Butyl 4-{4-[5-(2-formylphenyl)-4,5-dihydro-1,2-oxazol-3-yl]-1,3-thiazol-2-yl}piperidine-1-carboxylate (5.1 g) was reacted analogously to I-7 (Process G). This gave 2-{3-[2-(piperidin-4-yl)-1,3-thiazol-4-yl]-4,5-dihydro-1,2-oxazol-5-yl}benzaldehyde hydrochloride (4.35 g).

$^1$H NMR (DMSO-d$_6$): $\delta_{ppm}$: 2.02-1.89 (m, 2H), 2.23-2.15 (m, 2H), 3.08-2.97 (m, 2H), 3.18 (dd, 1H), 3.35-3.29 (m, 2H), 3.41-3.35 (m, 1H), 4.05 (dd, 1H), 6.42 (dd, 1H), 7.64-7.57 (m, 2H), 7.72 (dd, 1H), 8.02 (d, 1H), 8.03 (s, 1H), 10.19 (s, 1H)

log P (HCOOH): 0.76

MS (ESI): 342 ([M-Cl]$^+$)

Process H

2-{3-[2-(1-{[3,5-Bis(difluoromethyl)-1H-pyrazol-1-yl]acetyl}piperidin-4-yl)-1,3-thiazol-4-yl]-4,5-dihydro-1,2-oxazol-5-yl}benzaldehyde (I-26)

2-{3-[2-(Piperidin-4-yl)-1,3-thiazol-4-yl]-4,5-dihydro-1,2-oxazol-5-yl}benzaldehyde hydrochloride (432 mg) was reacted analogously to I-7 (Process G). This gave 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}benzaldehyde (330 mg).

2-[3,5-Bis(difluoromethyl)-1H-pyrazol-1-yl]-1-(4-{4-[5-(2-ethynylphenyl)-4,5-dihydro-1,2-oxazol-3-yl]-1,3-thiazol-2-yl}piperidin-1-yl)ethanone (I-38)

To a solution of 4-acetamidobenzenesulphonyl azide (140 mg) in acetonitrile (10 ml) was added, at room temperature, dimethyl 2-oxopropylphosphonate (97 mg). After stirring for 2 hours, 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}benzaldehyde (267 mg) in methanol (2 ml) was added to the reaction mixture. After stirring for 8 hours, the reaction mixture was admixed with ethyl acetate and water and extracted with ethyl acetate. The organic extracts were dried over sodium sulphate and concentrated under reduced pressure. The residue was purified by chromatography. This gave tert-2-[3,5-bis(difluoromethyl)-1H-pyrazol-1-yl]-1-(4-{4-[5-(2-ethynylphenyl)-4,5-dihydro-1,2-oxazol-3-yl]-1,3-thiazol-2-yl}piperidin-1-yl)ethanone (50 mg).

N-(2-{3-[2-(1-{[3,5-Bis(difluoromethyl)-1H-pyrazol-1-yl]acetyl}piperidin-4-yl)-1,3-thiazol-4-yl]-4,5-dihydro-1,2-oxazol-5-yl}phenyl)methanesulphonamide (I-37)

Processes D and E tert-Butyl 4-[4-(5-{2-[(methylsulphonyl)amino]phenyl}-4,5-dihydro-1,2-oxazol-3-yl)-1,3-thiazol-2-yl]piperidine-1-carboxylate (X-a-4)

tert-Butyl 4-{4-[(Z/E)-(hydroxyimino)methyl]-1,3-thiazol-2-yl}piperidine-1-carboxylate (1.35 g) and N-(2-vinylphenyl)methanesulphonamide (1.11 g) were reacted analogously to I-7 (Processes D and E). This gave tert-butyl 4-[4-(5-{2-[(methylsulphonyl)amino]phenyl}-4,5-dihydro-1,2-oxazol-3-yl)-1,3-thiazol-2-yl]piperidine-1-carboxylate (0.94 g).

$^1$H NMR (DMSO-d$_6$): $\delta_{ppm}$: 1.41 (s, 9H), 1.51-1.49 (m, 2H), 2.08-2.00 (m, 2H), 2.95-2.84 (m, 2H), 3.03 (s, 3H), 3.38-3.21 (m, 2H), 3.90 (dd, 1H), 4.05-3.96 (m, 2H), 6.09 (dd, 1H), 7.43-7.30 (m, 4H), 8.00 (s, 1H), 9.18 (bs, 1H)

log P (HCOOH): 3.00

MS (ESI): 407 ([M-COOC(CH$_3$)$_3$+2H]$^+$)

Process G

4-[4-(5-{2-[(Methylsulphonyl)amino]phenyl}-4,5-dihydro-1,2-oxazol-3-yl)-1,3-thiazol-2-yl]piperidinium chloride (XII-4)

tert-Butyl 4-[4-(5-{2-[(methylsulphonyl)amino]phenyl}-4,5-dihydro-1,2-oxazol-3-yl)-1,3-thiazol-2-yl]piperidine-1-carboxylate (900 mg) was reacted analogously to I-7 (Process G). This gave 4-[4-(5-{2-[(methylsulphonyl)amino]phenyl}-4,5-dihydro-1,2-oxazol-3-yl)-1,3-thiazol-2-yl]piperidinium chloride (1.00 g).

log P (HCOOH): 0.72
MS (ESI): 407 ([M-Cl+2H]$^+$)

Process H

N-(2-{3-[2-(1-{[3,5-Bis(difluoromethyl)-1H-pyrazol-1-yl]acetyl}piperidin-4-yl)-1,3-thiazol-4-yl]-4,5-dihydro-1,2-oxazol-5-yl}phenyl)methanesulphonamide (I-37)

4-[4-(5-{2-[(Methylsulphonyl)amino]phenyl}-4,5-dihydro-1,2-oxazol-3-yl)-1,3-thiazol-2-yl]piperidinium chloride (299 mg) was reacted analogously to I-7 (Process G). This gave N-(2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl)methanesulphonamide (215 mg).

2-[3,5-Bis(difluoromethyl)-1H-pyrazol-1-yl]-1-(4-{4-[5-(2-hydroxyphenyl)-4,5-dihydro-1,2-oxazol-3-yl]-1,3-thiazol-2-yl}piperidin-1-yl)ethanone (I-9)

Processes D and E tert-Butyl 4-{4-[5-(2-hydroxyphenyl)-4,5-dihydro-1,2-oxazol-3-yl]-1,3-thiazol-2-yl}piperidine-1-carboxylate (X-a-5)

To a solution of tert-butyl 4-{4-[(hydroxyimino)methyl]-1,3-thiazol-2-yl}piperidine-1-carboxylate (3.46 g) and 2-vinylphenol (1.60 g) in ethyl acetate (50 ml) were added, at room temperature, potassium hydrogencarbonate (5.55 g) and N-chlorosuccinimide (1.78 g), and then one drop of water. After stirring at 60° C. overnight, the reaction mixture was admixed with ethyl acetate and water and extracted with ethyl acetate. The organic extracts were dried over sodium sulphate and concentrated under reduced pressure. The residue was purified by chromatography. This gave tert-butyl 4-{4-[5-(2-hydroxyphenyl)-4,5-dihydro-1,2-oxazol-3-yl]-1,3-thiazol-2-yl}piperidine-1-carboxylate (1.70 g).

$^1$H NMR (DMSO-d$_6$, 400 MHz): δ$_{ppm}$: 1.41 (s, 9H), 1.49-1.61 (m, 2H), 1.98-2.06 (m, 2H), 2.82-2.96 (m, 2H), 3.80 (dd, 3.96-4.05 (m, 2H), 5.82 (dd, 1H), 6.79 (t, 1H), 6.85 (d, 1H), 7.13 (t, 1H), 7.20 (d, 1H), 7.98 (s, 1H), 9.70 (s, 1H)
log P (pH2.7): 3.22
MS (ESI): 330 ([M+H—C$_4$H$_9$OCO]$^+$)

Process G

4-{4-[5-(2-Hydroxyphenyl)-4,5-dihydro-1,2-oxazol-3-yl]-1,3-thiazol-2-yl}piperidinium chloride (XII-5)

To a solution of tert-butyl 4-{4-[5-(2-hydroxyphenyl)-4,5-dihydro-1,2-oxazol-3-yl]-1,3-thiazol-2-yl}piperidine-1-carboxylate (1.70 g) in dichloromethane was added dropwise, at 0° C. a 4 molar solution of hydrogen chloride (4.0 eq.) in 1,4-dioxane. The reaction mixture was stirred at 0° C. and then gradually warmed to room temperature. After stirring overnight, the solvent and excess hydrogen chloride were removed. This gave 4-{4-[5-(2-hydroxy-phenyl)-4,5-dihydro-1,2-oxazol-3-yl]-1,3-thiazol-2-yl}piperidinium chloride (1.45 g).

$^1$H NMR (DMSO-d$_6$, 400 MHz): δ$_{ppm}$: 1.85-1.98 (m, 2H), 2.15-2.23 (m, 2H), 2.98-3.09 (m, 2H), 3.26 (dd, 1H), 3.81 (dd, 1H), 5.83 (dd, 1H), 6.79 (t, 1H), 6.86 (d, 1H), 7.13 (t, 1H), 7.20 (d, 1H), 8.02 (s, 1H), 8.58 (bs, 1H), 8.87 (bs, 1H), 9.74 (s, 1H)
log P (pH2.7): 0.69
MS (ESI): 330 ([M+H]$^+$)

Process H

2-[3,5-Bis(difluoromethyl)-1H-pyrazol-1-yl]-1-(4-[4-[5-(2-hydroxyphenyl)-4,5-dihydro-1,2-oxazol-3-yl]-1,3-thiazol-2-yl]piperidin-1-yl)ethanone (I-9)

To a solution of [3,5-bis-(difluoromethyl)-1H-pyrazol-1-yl]acetic acid (982 mg) in dichloromethane (10 ml) are added, at 0° C., oxalyl chloride (1.50 g) and one drop of N,N-dimethylformamide. The reaction mixture is stirred at room temperature for 60 minutes. The solvent and the excess reagent are removed under reduced pressure. The solid residue is dissolved again in dichloromethane and added dropwise at 0° C. to a solution of 4-{4-[5-(2-hydroxyphenyl)-4,5-dihydro-1,2-oxazol-3-yl]-1,3-thiazol-2-yl}piperidinium chloride (1.45 g) and triethylamine (5.5 ml) in dichloromethane (14 ml). The reaction mixture is stirred at room temperature for 3 h. Then it is admixed with concentrated sodium hydrogencarbonate solution, and the aqueous phase is removed and extracted with ethyl acetate. The combined organic phases are dried over sodium sulphate and concentrated. Purification by column chromatography gives 2-[3,5-bis(difluoromethyl)-1H-pyrazol-1-yl]-1-(4-{4-[5-(2-hydroxyphenyl)-4,5-dihydro-1,2-oxazol-3-yl]-1,3-thiazol-2-yl}piperidin-1-yl)ethanone (900 mg).

2-[3,5-Bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone (I-21)

To a solution of 2-[3,5-bis(difluoromethyl)-1H-pyrazol-1-yl]-1-(4-{4-[5-(2-hydroxyphenyl)-4,5-dihydro-1,2-oxazol-3-yl]-1,3-thiazol-2-yl}piperidin-1-yl)ethanone (60 mg) and potassium carbonate (23 mg) in DMF (3 ml) are added, at room temperature, potassium iodide (10 mg) and 3-bromoprop-1-yne (21 mg). The reaction mixture is stirred at 80° C. for 9 h. Then the mixture is admixed with dilute hydrochloric acid and extracted with ethyl acetate. The combined organic phases are dried over sodium sulphate and concentrated. Purification by column chromatography gives 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone (40 mg).

2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl cyclohexanecarboxylate (I-32)

To a solution of 2-[3,5-bis(difluoromethyl)-1H-pyrazol-1-yl]-1-(4-{4-[5-(2-hydroxyphenyl)-4,5-dihydro-1,2-oxazol-3-yl]-1,3-thiazol-2-yl}piperidin-1-yl)ethanone (150 mg) and triethylamine (33 mg) in methylene chloride (10 ml) is added, at 0° C., a solution of cyclohexanecarbonyl chloride in methylene chloride (2 ml). The ice bath is removed and the reaction mixture is stirred at 0° C.-RT for 3 h. Then the mixture is admixed with dilute sodium hydrogencarbonate solution and extracted with methylene chloride. The combined organic phases are dried over sodium sulphate and concentrated. Purification by column chromatography gives 2-{3-[2-(1-[3,5-bis(difluoromethyl)-1H-pyrazol-1-yl]acetyl}piperidin-4-yl)-1,3-thiazol-4-yl]-4,5-dihydro-1,2-oxazol-5-yl)phenyl cyclohexanecarboxylate (150 mg).

2-[3,5-Bis(difluoromethyl)-1H-pyrazol-1-yl]-1-(4-{4-[5-(2-nitrophenyl)-4,5-dihydro-1,2-oxazol-3-yl]-1,3-thiazol-2-yl}piperidin-1-yl)ethanone (I-10)

Processes D and E tert-Butyl 4-{4-[5-(2-nitrophenyl)-4,5-dihydro-1,2-oxazol-3-yl]-1,3-thiazol-2-yl}piperidine-1-carboxylate (X-a-6)

To a solution of tert-butyl 4-(4-[(hydroxyimino)methyl]-1,3-thiazol-2-yl)piperidine-1-carboxylate (2.80 g) and 1-nitro-2-vinylbenzene (1.60 g) in ethyl acetate (50 ml) were added, at room temperature, potassium hydrogencarbonate (4.50 g) and N-chlorosuccinimide (1.44 g) and then one drop of water. After stirring at 60° C. overnight, the reaction mixture was admixed with ethyl acetate and water and extracted with ethyl acetate. The organic extracts were dried over sodium sulphate and concentrated under reduced pressure. The residue was purified by chromatography. This gave tert-butyl 4-{4-[5-(2-nitrophenyl)-4,5-dihydro-1,2-oxazol-3-yl]-1,3-thiazol-2-yl}piperidine-1-carboxylate (2.10 g).

$^1$H NMR (DMSO-$d_6$, 400 MHz): $\delta_{ppm}$: 1.40 (s, 9H), 1.48-1.60 (m, 2H), 1.98-2.06 (m, 2H), 2.81-2.96 (m, 2H), 3.40 (dd, 1H), 3.96-4.04 (m, 2H), 4.09 (dd, 1H), 6.24 (dd, 1H), 7.64 (t, 1H), 7.66 (d, 1H), 7.79 (t, 1H), 8.02 (s, 1H), 8.15 (d, 1H)

log P (pH2.7): 4.01

MS (ESI): 359 ([M+H—$C_4H_9OCO$]$^+$)

Process G

4-{4-[5-(2-Nitrophenyl)-4,5-dihydro-1,2-oxazol-3-yl]-1,3-thiazol-2-yl}piperidinium chloride (XII-6)

To a solution of tert-butyl 4-{4-[5-(2-nitrophenyl)-4,5-dihydro-1,2-oxazol-3-yl]-1,3-thiazol-2-yl}piperidine-1-carboxylate (2.10 g) in dichloromethane was added dropwise, at 0° C., a 4 molar solution of hydrogen chloride (4.0 eq.) in 1,4-dioxane. The reaction mixture was stirred at 0° C. and then gradually warmed to room temperature. After stirring overnight, the solvent and excess hydrogen chloride were removed. This gave 4-{4-[5-(2-nitrophenyl)-4,5-dihydro-1,2-oxazol-3-yl]-1,3-thiazol-2-yl}piperidinium chloride (1.60 g).

$^1$H NMR (DMSO-$d_6$, 400 MHz): $\delta_{ppm}$: 1.86-1.97 (m, 2H), 2.15-2.23 (m, 2H), 2.98-3.09 (m, 2H), 4.10 (dd, 1H), 6.24 (dd, 1H), 7.62 (t, 1H), 7.67 (d, 1H), 7.81 (t, 1H), 8.07 (s, 1H), 8.16 (d, 1H), 8.63 (bs, 1H), 8.91 (bs, 1H)

log P (pH2.7): 1.09

MS (ESI): 359 ([M+H]$^+$)

Process H

2-[3,5-Bis(difluoromethyl)-1H-pyrazol-1-yl]-1-(4-{4-[5-(2-nitrophenyl)-4,5-dihydro-1,2-oxazol-3-yl]-1,3-thiazol-2-yl}piperidin-1-yl)ethanone (I-10)

To a solution of [3,5-bis-(difluoromethyl)-1H-pyrazol-1-yl]acetic acid (0.37 g) in dichloromethane (10 ml) are added, at 0° C., oxalyl chloride (0.57 g) and one drop of N,N-dimethylformamide. The reaction mixture is stirred at room temperature for 60 minutes. The solvent and the excess reagent are removed under reduced pressure. The solid residue is dissolved again in dichloromethane and added dropwise, at 0° C., to a solution of 4-{4-[5-(2-nitrophenyl)-4,5-dihydro-1,2-oxazol-3-yl]-1,3-thiazol-2-yl}piperidinium chloride (0.59 g) and triethylamine (2.1 ml) in dichloromethane (14 ml). The reaction mixture is stirred at room temperature for 20 h. Then it is admixed with concentrated sodium hydrogencarbonate solution, and the aqueous phase is removed and extracted with ethyl acetate. The combined organic phases are dried over sodium sulphate and concentrated. Purification by column chromatography gives 2-[3,5-bis(difluoromethyl)-1H-pyrazol-1-yl]-1-(4-{4-[5-(2-nitrophenyl)-4,5-dihydro-1,2-oxazol-3-yl]-1,3-thiazol-2-yl}piperidin-1-yl)ethanone (170 mg).

1-(4-[4-[5-(2-Aminophenyl)-4,5-dihydro-1,2-oxazol-3-yl]-1,3-thiazol-2-yl]piperidin-1-yl)-2-[3,5-bis(difluoromethyl)-1H-pyrazol-1-yl]ethanone (I-41)

To a solution of 2-[3,5-bis(difluoromethyl)-1H-pyrazol-1-yl]-1-(4-{4-[5-(2-nitrophenyl)-4,5-dihydro-1,2-oxazol-3-yl]-1,3-thiazol-2-yl}piperidin-1-yl)ethanone (80 mg) in methanol (10 ml) is added, at room temperature, Pd/C (20 mg, 10%). The reaction mixture is stirred under a hydrogen atmosphere at room temperature for 3 hours, then volatile constituents are removed under reduced pressure. Purification by column chromatography gives 1-(4-{4-[5-(2-aminophenyl)-4,5-dihydro-1,2-oxazol-3-yl]-1,3-thiazol-2-yl}piperidin-1-yl)-2-[3,5-bis(difluoromethyl)-1H-pyrazol-1-yl]ethanone (25 mg).

2-[3,5-Bis(difluoromethyl)-1H-pyrazol-1-yl]-1-[4-(4-{5-[2-(cyclohexylmethoxy)phenyl]-4,5-dihydro-1,2-oxazol-3-yl}-1,3-thiazol-2-yl)piperidin-1-yl]ethanone (I-24)

Processes D and E tert-Butyl 4-(4-{5-[2-(cyclohexylmethoxy)phenyl]-4,5-dihydro-1,2-oxazol-3-yl}-1,3-thiazol-2-yl)piperidine-1-carboxylate (X-a-7)

To a solution of tea-butyl 4-{4-[(hydroxyimino)methyl]-1,3-thiazol-2-yl}piperidine-1-carboxylate (2.90 g) and 1-(cyclohexylmethoxy)-2-vinylbenzene (2.40 g) in ethyl acetate (300 ml) were added, at room temperature, potassium hydrogencarbonate (4.60 g) and N-chlorosuccinimide (1.48 g), and then one drop of water. The reaction mixture was stirred at 60° C. for 6 h, then admixed with ethyl acetate and water and extracted with ethyl acetate. The organic extracts were dried over sodium sulphate and concentrated under reduced pressure. The residue was purified by chromatography. This gave tert-butyl 4-(4-{5-[2-(cyclohexylmethoxy)phenyl]-4,5-dihydro-1,2-oxazol-3-yl}-1,3-thiazol-2-yl)piperidine-1-carboxylate (3.40 g).

¹H NMR (DMSO-d₆, 400 MHz): δ$_{ppm}$: 0.97-1.12 (m, 5H), 1.40 (s, 9H), 1.50-1.80 (m, 8H), 1.98-2.06 (m, 2H), 2.81-2.96 (m, 2H), 3.74-3.81 (m, 3H), 3.95-4.03 (m, 2H), 5.78 (dd, 1H), 6.92 (t, 1H), 7.00 (d, 1H), 7.26-7.33 (m, 2H), 7.97 (s, 1H)
  log P (pH2.7): 6.30
  MS (ESI): 426 ([M+H—C₄H₉OCO]⁺)

Process G 4-(4-{5-[2-(Cyclohexylmethoxy)phenyl]-4,5-dihydro-1,2-oxazol-3-yl}-1,3-thiazol-2-yl)-piperidinium chloride (XII-7)

To a solution of tert-butyl 4-(4-{5-[2-(cyclohexylmethoxy)phenyl]-4,5-dihydro-1,2-oxazol-3-yl}-1,3-thiazol-2-yl)piperidine-1-carboxylate (3.20 g) in dichloromethane was added dropwise, at 0° C. a 4 molar solution of hydrogen chloride (4.0 eq.) in 1,4-dioxane. The reaction mixture was stirred at 0° C. and then gradually warmed to room temperature. After stirring overnight, the solvent and excess hydrogen chloride were removed. This gave 4-(4-{5-[2-(cyclohexylmethoxy)phenyl]-4,5-dihydro-1,2-oxazol-3-yl}-1,3-thiazol-2-yl)piperidinium chloride (2.50 g).
  ¹H NMR (DMSO-d₆, 400 MHz): δ$_{ppm}$: 0.92-1.14 (m, 5H), 1.51-1.81 (m, 6H), 1.93-2.07 (m, 2H), 2.14-2.27 (m, 2H), 2.92-3.10 (m, 2H), 3.26-3.47 (m, 4H), 3.71-3.86 (m, 3H), 5.80 (dd, 1H), 6.91 (t, 1H), 7.01 (d, 1H), 7.25-7.34 (m, 2H), 8.01 (s, 1H), 9.30 (s, 1H), 9.52 (s, 1H)
  log P (pH2.7): 1.90
  MS (ESI): 426 ([M+H]⁺)

Process H

2-[3,5-Bis(difluoromethyl)-1H-pyrazol-1-yl]-1-[4-(4-{5-[2-(cyclohexylmethoxy)phenyl]-4,5-dihydro-1,2-oxazol-3-yl}-1,3-thiazol-2-yl)piperidin-1-yl]ethanone (I-24)

To a solution of [3,5-bis-(difluoromethyl)-1H-pyrazol-1-yl]acetic acid (1.49 g) in dichloromethane (10 ml) are added, at 0° C., oxalyl chloride (2.29 g) and one drop of N,N-dimethylformamide. The reaction mixture is stirred at room temperature for 60 minutes. The solvent and the excess reagent are removed under reduced pressure. The solid residue is dissolved again in dichloromethane and added dropwise, at 0° C., to a solution of 4-(4-{5-[2-(cyclohexylmethoxy)phenyl]-4,5-dihydro-1,2-oxazol-3-yl}-1,3-thiazol-2-yl)piperidinium chloride (2.55 g) and triethylamine (8.36 ml) in dichloromethane (14 ml). The reaction mixture is stirred at room temperature for 20 h. Then it is admixed with concentrated sodium hydrogencarbonate solution, and the aqueous phase is removed and extracted with ethyl acetate. The combined organic phases are dried over sodium sulphate and concentrated. Purification by column chromatography gives 2-[3,5-bis(difluoromethyl)-1H-pyrazol-1-yl]-1-[4-(4-{5-[2-(cyclohexylmethoxy)phenyl]-4,5-dihydro-1,2-oxazol-3-yl}-1,3-thiazol-2-yl)piperidin-1-yl]ethanone (1.87 g).

2-{3-[2-{[3,5-Bis(difluoromethyl)-1H-pyrazol-1-yl]acetyl}piperidin-4-yl)-1,3-thiazol-4-yl]-1,2-oxazol-5-yl}benzaldehyde (I-31)

Processes D and E tert-Butyl 4-{4-[5-(2-formylphenyl)-1,2-oxazol-3-yl]-1,3-thiazol-2-yl}piperidine-1-carboxylate (X-b-1)

To a solution of rest-butyl 4-{4-[(hydroxyimino)methyl]-1,3-thiazol-2-yl}piperidine-1-carboxylate (1.00 g) in DMF (10 ml) was added, at 50° C., N-chlorosuccinimide (0.51 g), and the mixture was stirred for 30 minutes. At room temperature, triethylamine (1.34 ml) and 2-ethynylbenzaldehyde (0.54 g) were added to the reaction mixture. After stirring at 50° C. for 2 hours, the reaction mixture was admixed with ethyl acetate and water and extracted with ethyl acetate. The organic extracts were dried over sodium sulphate and concentrated under reduced pressure. The residue was purified by chromatography. This gave tert-butyl 4-{4-[5-(2-formylphenyl)-1,2-oxazol-3-yl]-1,3-thiazol-2-yl}piperidine-1-carboxylate (95 mg).
  ¹H NMR (DMSO-d₆): δ$_{ppm}$: 1.42-1.41 (m, 9H), 1.69-1.50 (m, 2H), 2.12-1.98 (m, 2H), 2.90 (bs, 2H), 3.40-3.28 (m, 1H), 4.10-3.95 (m, 2H), 7.44 (s, 1H), 7.77 (dd, 1H), 7.87 (dd, 1H), 7.94 (d, 1H), 8.02 (d, 1H), 8.29 (s, 1H), 10.29 (s, 1H)
  log P (HCOOH): 4.10
  MS (ESI): 340 ([M-COOC(CH₃)₃+2H]⁺)

Processes G and H

2-{3-[2-(1-{[3,5-Bis(difluoromethyl)-1H-pyrazol-1-yl]acetyl}piperidin-4-yl)-1,3-thiazol-4-yl]-1,2-oxazol-5-yl}benzaldehyde (I-31)

To a solution of tert-butyl 4-{4-[5-(2-formylphenyl)-1,2-oxazol-3-yl]-1,3-thiazol-2-yl}piperidine-1-carboxylate (95 mg) in dichloromethane was added dropwise, at 0° C., a 4 molar solution of hydrogen chloride (2 ml) in 1,4-dioxane. The reaction mixture was stirred at 0° C. and then gradually warmed to room temperature. After stirring overnight, the solvent and excess hydrogen chloride were removed. This gave 4-{4-[5-(2-formylphenyl)-1,2-oxazol-3-yl]-1,3-thiazol-2-yl}piperidinium chloride (XII-8).
To a solution of [3,5-bis-(difluoromethyl)-1H-pyrazol-1-yl]acetic acid (51 mg) in dichloromethane (2 ml) are added, at 0° C., oxalyl chloride (57 μL) and one drop of N,N-dimethylformamide. The reaction mixture is stirred at room temperature for 60 minutes. The solvent and the excess reagent are removed under reduced pressure. The solid residue is again dissolved in dichloromethane and added dropwise at 0° C. to a solution of 4-{4-[5-(2-formylphenyl)-1,2-oxazol-3-yl]-1,3-thiazol-2-yl}piperidinium chloride and triethylamine (90 μl) in dichloromethane (2 ml). The reaction mixture is stirred at room temperature for 3 h. Then it is admixed with concentrated sodium hydrogencarbonate solution, and the aqueous phase is removed and extracted with ethyl acetate. The combined organic phases are dried over sodium sulphate and concentrated. Purification by column chromatography gives 2-{3-[2-(1-{[3,5-bis(difluoromethyl)-1H-pyrazol-1-yl]acetyl}piperidin-4-yl)-1,3-thiazol-4-yl]-1,2-oxazol-5-yl}benzaldehyde (36 mg).

Cyclopropylmethyl 2-{3-[2-{[3,5-bis(difluoromethyl)-1H-pyrazol-1-yl]acetyl}piperidin-4-yl)-1,3-thiazol-4-yl]-4,5-dihydro-1,2-oxazol-5-yl}benzoate (I-13)

Processes D and E tert-Butyl 4-(4-{5-[2-(methoxycarbonyl)phenyl]-4,5-dihydro-1,2-oxazol-3-yl}-1,3-thiazol-2-yl)piperidine-1-carboxylate (X-a-8)

text-Butyl 4-{4-[(Z/E)-(hydroxyimino)methyl]-1,3-thiazol-2-yl}piperidine-1-carboxylate (600 mg) and methyl 2-vinylbenzoate (406 mg) were reacted analogously to I-31 (Processes D and E). This gave tart-butyl 4-(4-{5-[2-

(methoxycarbonyl)phenyl]-4,5-dihydro-1,2-oxazol-3-yl}-1,3-thiazol-2-yl)piperidine-1-carboxylate (643 mg).

$^1$H NMR (DMSO-d$_6$): δ$_{ppm}$: 1.40 (s, 9H), 1.60-1.49 (m, 2H), 2.05-1.96 (m, 2H), 2.98-2.75 (m, 2H), 3.20 (dd, 1H), 3.26-3.20 (m, 1H), 3.88 (s, 3H), 4.02 (dd, 1H), 4.05-3.93 (m, 2H), 6.30 (dd, 1H), 7.48 (dd, 1H), 7.55 (d, 1H), 7.65 (dd, 1H), 7.96 (d, 1H), 8.00 (s, 1H)

log P (HCOOH): 4.14

MS (ESI): 372 ([M-COOC(CH$_3$)$_3$+2H]$^+$)

2-(3-{2-[1-(tert-Butoxycarbonyl)piperidin-4-yl]-1,3-thiazol-4-yl}-4,5-dihydro-1,2-oxazol-5-yl)benzoic acid (X-a-9)

To a solution of tert-butyl 4-(4-{5-[2-(methoxycarbonyl)phenyl]-4,5-dihydro-1,2-oxazol-3-yl}-1,3-thiazol-2-yl)piperidine-1-carboxylate (643 mg) in tetrahydrofuran (4 ml) and water (0.8 ml) is added, at room temperature, lithium hydroxide monohydrate (86 mg). The mixture is stirred at room temperature for 2 h and then admixed with ice-cold 1N HCl solution. The aqueous phase is extracted with ethyl acetate and then the combined organic phases are dried with sodium sulphate. The solids are filtered off and the solvent is distilled off. This gives 2-(3-{2-[1-(tert-butoxycarbonyl)piperidin-4-yl]-1,3-thiazol-4-yl}-4,5-dihydro-1,2-oxazol-5-yl)benzoic acid (377 mg).

$^1$H NMR (DMSO-d$_6$): δ$_{ppm}$: 1.40 (s, 9H), 1.56-1.48 (m, 2H), 2.04-1.99 (m, 2H), 2.88 (bs, 2H), 3.18 (dd, 1H), 3.28-3.19 (m, 1H), 4.04-3.98 (m, 3H), 6.48 (dd, 1H), 7.43 (d, 1H), 7.52 (d, 1H), 7.60 (dd, 1H), 7.96 (d, 1H), 8.01 (s, 1H)

log P (HCOOH): 3.18

MS (ESI): 358 ([M-COOC(CH$_3$)$_3$+2 H]$^+$)

tert-Butyl 4-[4-(5-{2-[(cyclopropylmethoxy)carbonyl]phenyl}-4,5-dihydro-1,2-oxazol-3-yl)-1,3-thiazol-2-yl]piperidine-1-carboxylate (X-a-10)

To a solution of 2-(3-{2-[1-(tert-butoxycarbonyl)piperidin-4-yl]-1,3-thiazol-4-yl}-4,5-dihydro-1,2-oxazol-5-yl)benzoic acid (300 mg) in dichloromethane (10 ml) are added, at room temperature, cyclopropylmethanol (47 mg), 4-dimethylaminopyridine (8 mg) and 1-ethyl-3-(3'-dimethylaminopropyl)carbodiimide (132 mg). The mixture is stirred at room temperature for 3 hours and then admixed with water. The aqueous phase is removed and extracted with ethyl acetate. The combined organic phases are dried over sodium sulphate and concentrated under reduced pressure. The residue is purified by chromatography. This gives tert-butyl 4-[4-(5-{2-[(cyclopropylmethoxy)carbonyl]phenyl}-4,5-dihydro-1,2-oxazol-3-yl)-1,3-thiazol-2-yl]piperidine-1-carboxylate (270 mg).

$^1$H NMR (DMSO-d$_6$): δ$_{ppm}$: 0.40-0.37 (m, 2H), 0.61-0.56 (m, 2H), 1.30-1.22 (m, 1H), 1.40 (s, 9H), 1.59-1.48 (m, 2H), 2.05-1.98 (m, 2H), 2.88 (bs, 2H), 3.26-3.18 (m, 2H), 4.08-3.96 (m, 3H), 4.15 (dd, 2H), 6.31 (dd, 1H), 7.48 (dd, 1H), 7.56 (d, 1H), 7.65 (dd, 1H), 7.96 (d, 1H), 8.00 (s, 1H)

log P (HCOOH): 4.99

MS (ESI): 412 ([M-COOC(CH$_3$)$_3$+2H]$^+$)

Processes G and H

Cyclopropylmethyl 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}benzoate (I-13)

tert-Butyl 4-[4-(5-{2-[(cyclopropylmethoxy)carbonyl]phenyl}-4,5-dihydro-1,2-oxazol-3-yl)-1,3-thiazol-2-yl]piperidine-1-carboxylate (270 mg) was reacted analogously to I-31 (Processes G and H). This gave cyclopropylmethyl 2-{3-[2-(1-{[3,5-bis(difluoromethyl)-1,1-pyrazol-1-yl]acetyl}piperidin-4-yl)-1,3-thiazol-4-yl]-4,5-dihydro-1,2-oxazol-5-yl}-benzoate (136 mg).

Methyl 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}benzoate (I-43) and methyl 2-{3-[2-(1-{[3,5-bis(difluoromethyl)-1H-pyrazol-1-yl]acetyl}piperidin-4-yl)-5-chloro-1,3-thiazol-4-yl]-4,5-dihydro-1,2-oxazol-5-yl}benzoate (I-46)

4-(4-Formyl-1,3-thiazol-2-yl)piperidinium chloride

To tert-butyl 4-(4-formyl-1,3-thiazol-2-yl)piperidine-1-carboxylate (10 g) was added dropwise, at 0° C. a 4 molar solution of hydrogen chloride in 1,4-dioxane (100 ml). The reaction mixture was stirred at 0° C. and then gradually warmed to room temperature. After stirring overnight, the solvent and excess hydrogen chloride were removed. This gave 4-(4-formyl-1,3-thiazol-2-yl)piperidinium chloride (9 g).

$^1$H NMR (DMSO-d$_6$): δ$_{ppm}$: 2.05-1.94 (m, 2.25-2.17 (m, 2H), 3.09-2.97 (m, 2H), 3.37-3.30 (m, 2H), 3.48-3.40 (m, 1H), 8.68 (s, 1H), 9.15 (bs, 1H), 9.32 (bs, 1H), 9.90 (s, 1H)

2-(1-{[3,5-Bis(difluoromethyl)-1H-pyrazol-1-yl]acetyl}piperidin-4-yl)-1,3-thiazole-4-carbaldehyde (VI-2)

To a solution of [3,5-bis-(difluoromethyl)-1H-pyrazol-1-yl]acetic acid (3.64 g) in dichloromethane (20 ml) are added, at 0° C. oxalyl chloride (3.5 ml) and one drop of N,N-dimethylformamide. The reaction mixture is stirred at room temperature for 10 minutes. The solvent and the excess reagent are removed under reduced pressure. The solid residue is again dissolved in dichloromethane and, at 0° C., added dropwise to a solution of 4-(4-formyl-1,3-thiazol-2-yl)piperidinium chloride (3.11 g) and triethylamine (5.6 ml) in dichloromethane (20 ml). The reaction mixture is stirred at room temperature for 3 hours. Then it is admixed with concentrated sodium hydrogencarbonate solution, and the aqueous phase is removed and extracted with ethyl acetate. The combined organic phases are dried over sodium sulphate and concentrated. Purification by column chromatography gives 2-(1-{[3,5-bis(difluoromethyl)-1H-pyrazol-1-yl]acetyl}piperidin-4-yl)-1,3-thiazole-4-carbaldehyde (4.52 g).

$^1$H NMR (DMSO-d$_6$): δ$_{ppm}$: 1.65-1.53 (m, 1H), 1.89-1.77 (m, 1H), 2.18-2.08 (m, 2H), 2.90-2.80 (m, 1H), 3.48-3.22 (m, 2H), 4.00-3.93 (m, 2H), 4.38-4.31 (m, 1H), 5.34 (d, 1H), 5.39 (d, 1H), 6.90 (s, 1H), 7.02 (t, 1H), 7.18 (t, 1H), 8.65 (s, 1H), 9.90 (s, 1H)

log P (HCOOH): 1.93

MS (ESI): 405 ([M+H]$^+$)

Processes D and E

2-(1-{[3,5-Bis(difluoromethyl)-1H-pyrazol-1-yl]acetyl}piperidin-4-yl)-1,3-thiazole-4-carbaldehyde oxime To a solution of 2-(1-{[3,5-bis(difluoromethyl)-1H-pyrazol-1-yl]acetyl}piperidin-4-yl)-1,3-thiazole-4-carbaldehyde (487 mg) in ethanol (5 ml) was added dropwise hydroxylamine (50% in water, 44 μl) at room temperature. The reaction mixture was stirred at 60° C. for 2 hours, then the solvent was removed under reduced pressure. This gave 2-(1-{[3,5-bis(difluoromethyl)-1H-pyrazol-1-yl]acetyl}piperidin-4-yl)-1,3-thiazole-4-carbaldehyde oxime (454 mg).

log P (HCOOH): 1.93 and 1.98 (2 isomers)

MS (ESI): 420 ([M+H]$^+$)

Methyl 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}benzoate (I-43) and methyl 2-{3-[2-(1-{[3,5-bis(difluoromethyl)-1H-pyrazol-1-yl]acetyl}piperidin-4-yl)-5-chloro-1,3-thiazol-4-yl]-4,5-dihydro-1,2-oxazol-5-yl}benzoate (I-46)

To a solution of 2-(1-{[3,5-bis(difluoromethyl)-1H-pyrazol-1-yl]acetyl}piperidin-4-yl)-1,3-thiazole-4-carbaldehyde oxime (1.00 g) in DMF (4 ml) was added, at 50° C., N-chlorosuccinimide (382 mg) and the mixture was stirred for 30 minutes. At room temperature, triethylamine (1 ml) and methyl 2-vinylbenzoate (0.50 g) were added to the reaction mixture. After stirring at 50° C. for 2 hours, the reaction mixture was admixed with ethyl acetate and water and extracted with ethyl acetate. The organic extracts were dried over sodium sulphate and concentrated under reduced pressure. The residue was purified by chromatography. This gave methyl 2-{3-[2-{[3,5-bis(difluoromethyl)-1H-pyrazol-1-yl]acetyl}piperidin-4-yl)-1,3-thiazol-4-yl]-4,5-dihydro-1,2-oxazol-5-yl}benzoate (287 mg) and methyl 2-{3-[2-(1-{[3,5-bis(difluoromethyl)-1H-pyrazol-1-yl]acetyl}piperidin-4-yl)-5-chloro-1,3-thiazol-4-yl]-4,5-dihydro-1,2-oxazol-5-yl}benzoate (193 mg).

2-{3-[2-(1-{[3,5-Bis(difluoromethyl)-1H-pyrazol-1-yl]acetyl}piperidin-4-yl)-1,3-thiazol-4-yl]-4,5-dihydro-1,2-oxazol-5-yl}-N-cyclopropylbenzamide (I-27)

2-{3-[2-(1-{[3,5-Bis(difluoromethyl)-1H-pyrazol-1-yl]acetyl}piperidin-4-yl)-1,3-thiazol-4-yl]-4,5-dihydro-1,2-oxazol-5-yl}benzoic acid To a solution of methyl 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}benzoate (208 trig) in tetrahydrofuran (1 ml) and water (0.2 ml) is added, at room temperature, lithium hydroxide monohydrate (23 mg). The mixture is stirred at room temperature for 2 h and then admixed with ice-cold 1N HCl solution. The aqueous phase is extracted with ethyl acetate and then the combined organic phases are dried with sodium sulphate. The solids are filtered off and the solvent is distilled off. This gives 2-{3-[2-(1-{[3,5-bis(difluoromethyl)-1H-pyrazol-1-yl]-acetyl}piperidin-4-yl)-1,3-thiazol-4-yl]-4,5-dihydro-1,2-oxa-zol-5-yl}benzoic acid (158 mg).

$^1$H NMR (DMSO-d$_6$): $\delta_{ppm}$: 1.61-1.50 (m, 1H), 1.59-1.73 (m, 1H), 2.15-2.02 (m, 2H), 2.87-2.78 (m, 1H), 3.48-3.15 (m, 3H), 4.05-3.92 (m, 2H), 4.38-4.30 (m, 1H), 5.34 (d, 1H), 5.42 (d, 1H), 6.38 (dd, 1H), 6.89 (s, 1H), 7.02 (t, 1H), 7.17 (t, 1H), 7.43 (dd, 1H), 7.54 (d, 1H), 7.60 (dd, 1H), 7.96 (d, 1H), 8.02 (s, 1H)

log P (HCOOH): 2.63

MS (ESI): 566 ([M+H]$^+$)

2-{3-[2-(1-{[3,5-Bis(difluoromethyl)-1H-pyrazol-1-yl]acetyl}piperidin-4-yl)-1,3-thiazol-4-yl]-4,5-dihydro-1,2-oxazol-5-yl}-N-cyclopropylbenzamide (I-27)

To a solution of 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}benzoic acid (105 mg) in dichloromethane (10 ml) are added, at room temperature, cyclopropanamine (11 mg), 4-dimethylaminopyridine (2 mg) and 1-ethyl-3-(3'-dimethylaminopropyl)carbodiimide (37 mg). The mixture is stirred at room temperature for 3 hours and then admixed with water. The aqueous phase is removed and extracted with ethyl acetate. The combined organic phases are dried over sodium sulphate and concentrated under reduced pressure. The residue is purified by chromatography. This gives 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-N-cyclopropylbenzamide (78 mg).

2-[3,5-Bis(difluoromethyl)-1H-pyrazol-1-yl]-1-[4-(4-{5-[2-(hydroxymethyl)phenyl]-4,5-dihydro-1,2-oxazol-3-yl}-1,3-thiazol-2-yl)piperidin-1-yl]ethanone (I-45)

To a solution of 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-benzaldehyde (1.9 g) in methanol (50 ml) was added, at 0° C., sodium borohydride (0.16 g), and then the mixture was stirred at room temperature for 2 hours. Subsequently, the reaction mixture was admixed at 0° C. with 0.1 molar hydrochloric acid and ethyl acetate. The organic extracts were dried over sodium sulphate and concentrated under reduced pressure. The residue was purified by chromatography. This gave 2-[3,5-bis(difluoromethyl)-1H-pyrazol-1-yl]-1-[4-(4-{5-[2-(hydroxymethyl)phenyl]-4,5-dihydro-1,2-oxazol-3-yl}-1,3-thiazol-2-yl)piperidin-1-yl]-ethanone (1.1 g).

2-[3,5-Bis(difluoromethyl)-1H-pyrazol-1-yl]-1-[4-(4-{5-[2-(chloromethyl)phenyl]-4,5-dihydro-1,2-oxazol-3-yl}-1,3-thiazol-2-yl)piperidin-1-yl]ethanone (I-44)

To a solution of 2-[3,5-bis(difluoromethyl)-1H-pyrazol-1-yl]-1-[4-(4-{5-[2-(hydroxymethyl)phenyl]-4,5-dihydro-1,2-oxazol-3-yl}-1,3-thiazol-2-yl)piperidin-1-yl]ethanone (0.55 g) in dichloromethane (10 ml) were added, at room temperature, thionyl chloride (0.24 g) and one drop of DMF, and the mixture was then refluxed for 2 hours. Subsequently, the reaction mixture was concentrated under reduced pressure. This gave, without further purification, 2-[3,5-bis(difluoromethyl)-1H-pyrazol-1-yl]-1-[4-(4-{5-[2-(chloromethyl)phenyl]-4,5-dihydro-1,2-oxazol-3-yl}-1,3-thiazol-2-yl)piperidin-1-yl]ethanone (0.59 g).

2-[3,5-Bis(difluoromethyl)-1H-pyrazol-1-yl]-1-{4-[4-(5-{2-[(2-methoxyethoxy)methyl]phenyl}-4,5-dihydro-1,2-oxazol-3-yl)-1,3-thiazol-2-yl]piperidin-1-yl}ethanone (I-11)

2-Methoxyethanol (1.5 ml) was admixed at room temperature with sodium hydride (60%, 17 mg) and then stirred at room temperature for 2 hours. To this mixture was added dropwise a solution of 2-[3,5-bis(difluoromethyl)-1H-pyrazol-1-yl]-1-[4-(4-{5-[2-(chloromethyl)phenyl]-4,5-dihydro-1,2-oxazol-3-yl}-1,3-thiazol-2-yl)piperidin-1-yl]ethanone (0.20 g) in 2-methoxyethanol (1.5 g), and the mixture was then stirred at room temperature for 16 hours. Subsequently, the reaction mixture was admixed with water and dichloromethane. The organic extracts were dried over sodium sulphate and concentrated under reduced pressure. The residue was purified by chromatography. This gave 2-[3,5-bis(difluoromethyl)-1H-pyrazol-1-yl]-1-{4-[4-(5-{2[(2-methoxyethoxy)methyl]phenyl}-4,5-dihydro-1,2-oxazol-3-yl)-1,3-thiazol-2-yl]piperidin-1-yl}ethanone (0.11 g).

2-[3,5-Bis(difluoromethyl)-1H-pyrazol-1-yl]-1-{4-[4-(5-{2-[(ethylsulphanyl)methyl]phenyl}-4,5-dihydro-1,2-oxazol-3-yl)-1,3-thiazol-2-yl]piperidin-1-yl}ethanone (I-12)

2-{3-[2-(1-{[3,5-Bis(difluoromethyl)-1H-pyrazol-1-yl]acetyl}piperidin-4-yl)-1,3-thiazol-4-yl]-4,5-dihydro-1,2-oxazol-5-yl}benzyl imidothiocarbamate A mixture of 2-[3,5-bis(difluoromethyl)-1H-pyrazol-1-yl]-1-[4-(4-{5-[2-(chloromethyl)phenyl]-4,5-dihydro-1,2-oxazol-3-yl}-1,3-thiazol-2-yl)piperidin-1-yl]ethanone (0.20 g) and thiourea (29 mg) in ethanol (5 ml) was refluxed for 1 hour. Subsequently, the reaction mixture was concentrated under reduced pressure and the residue was admixed with 5% sodium hydrogencarbonate solution and ethyl acetate. The organic extracts were dried over sodium sulphate and concentrated under reduced pressure. The residue was filtered through silica gel in a mixture of cyclohexane and ethyl acetate (1:2). This gave 2-{3-[2-(1-{[3,5-bis(difluoro-methyl)-1H-pyrazol-1-yl]acetyl}piperidin-4-yl)-1,3-thiazol-4-yl]-4,5-dihydro-1,2-oxazol-5-yl}benzyl imidothiocarbamate (0.15 g).
$^1$H NMR: $\delta_{ppm}$: 1.58 (m, 1H), 1.80 (m, 1H), 2.18-2.05 (m, 2H), 2.82 (m, 1H), 3.42-3.20 (m, 311), 3.97 (m, 2H), 4.32 (m, 2H), 5.40 (dd, 2H), 6.06 (dd, 1H), 6.59 (bs, 1H), 6.91 (s, 1H), 7.03 (t, 1H), 7.18 (t, 1H), 7.45-7.25 (m, 4H), 8.03 (s, 1H)
log P (HCOOH): 1.68

2-[3,5-Bis(difluoromethyl)-1H-pyrazol-1-yl]-1-{4-[4-(5-{2-[(ethylsulphanyl)methyl]phenyl}-4,5-dihydro-1,2-oxazol-3-yl)-1,3-thiazol-2-yl]piperidin-1-yl}ethanone (I-12)

To a solution of 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}benzyl imidothiocarbamate (0.15 g) in toluene (5 ml) were added 50% sodium hydroxide solution (0.5 ml), iodoethane (42 mg) and one drop of tetra-n-butylammonium bromide. Thereafter, the mixture was stirred vigorously at room temperature for 2 hours. Subsequently, the reaction mixture was admixed with water and ethyl acetate. The organic extracts were dried over sodium sulphate and concentrated under reduced pressure. The residue was purified by chromatography. This gave 2-[3,5-bis(difluoromethyl)-1H-pyrazol-1-yl]-1-{4-[4-(5-{2-[(ethylsulphanyl)methyl]phenyl}-4,5-dihydro-1,2-oxazol-3-yl)-1,3-thiazol-2-yl]piperidin-1-yl}ethanone (50 mg).

1-[4-(4-{5-[2-(Allyloxy)phenyl]-4,5-dihydro-1,2-oxazol-3-yl}-1,3-thiazol-2-yl)piperidin-1-yl]-2-[3,5-bis(difluoromethyl)-1H-pyrazol-1-yl]ethanone (I-14)

To a solution of 2-[3,5-bis(difluoromethyl)-1H-pyrazol-1-yl]-1-(4-{4-[5-(2-hydroxyphenyl)-4,5-dihydro-1,2-oxazol-3-yl]-1,3-thiazol-2-yl}piperidin-1-yl)ethanone (81 mg) and potassium carbonate (105 mg) in acetone (5 ml) is added, at room temperature, allyl bromide (73 mg). The reaction mixture is stirred at reflux for 5 h. Then the mixture is admixed with water and extracted with ethyl acetate. The combined organic phases are dried over sodium sulphate and concentrated. Purification by column chromatography gives 1-[4-(4-{5-[2-(allyloxy)phenyl]-4,5-dihydro-1,2-oxazol-3-yl}-1,3-thiazol-2-yl)piperidin-1-yl]-2-[3,5-bis(difluoromethyl)-1H-pyrazol-1-yl]ethanone (48 mg).

2-[3,5-Bis(difluoromethyl)-1H-pyrazol-1-yl]-1-{4-[4-(5-{2-[(3-methylbut-2-en-1-yl)oxy]phenyl}-4,5-dihydro-1,2-oxazol-3-yl)-1,3-thiazol-2-yl]piperidin-1-yl}ethanone (I-20) and 2-[3,5-bis(difluoromethyl)-1H-pyrazol-1-yl]-1-{4-[4-(5-{2-[(2-methylprop-2-en-1-yl)oxy]phenyl}-4,5-dihydro-1,2-oxazol-3-yl)-1,3-thiazol-2-yl]piperidin-1-yl}ethanone (I-18) were reacted analogously to I-14.

2-[3,5-Bis(difluoromethyl)-1H-pyrazol-1-yl]-1-[4-(4-{5-[2-(2-methoxyethoxy)phenyl]-4,5-dihydro-1,2-oxazol-3-yl}-1,3-thiazol-2-yl)piperidin-1-yl]ethanone (I-19)

To a solution of 2-[3,5-bis(difluoromethyl)-1H-pyrazol-1-yl]-1-(4-{4-[5-(2-hydroxyphenyl)-4,5-dihydro-1,2-oxazol-3-yl]-1,3-thiazol-2-yl}piperidin-1-yl)ethanone (81 mg) and potassium carbonate (105 mg) in N,N-dimethylformamide (5 ml) are added, at room temperature, 1-bromo-2-methoxyethane (84 mg) and potassium iodide (2.5 mg). The reaction mixture is stirred at 80° C. for 3 h. Then the mixture is admixed with water and extracted with ethyl acetate. The combined organic phases are dried over sodium sulphate and concentrated. Purification by column chromatography gives 2-[3,5-bis(difluoromethyl)-1H-pyrazol-1-yl]-1-[4-(4-{5-[2-(2-methoxyethoxy)phenyl]-4,5-dihydro-1,2-oxazol-3-yl}-1,3-thiazol-2-yl)piperidin-1-yl]ethanone (41 mg).

2-[3,5-Bis(difluoromethyl)-1H-pyrazol-1-yl]-1-[4-(4-{5-[3-(2-methoxyethoxy)phenyl]-4,5-dihydro-1,2-oxazol-3-yl}-1,3-thiazol-2-yl)piperidin-1-yl]ethanone (I-28)

Processes D and E tert-Butyl 4-(4-{5-[3-(2-methoxyethoxy)phenyl]-4,5-dihydro-1,2-oxazol-3-yl}-1,3-thiazol-2-yl)piperidine-1-carboxylate (X-a-11)

tert-Butyl 4-{4-[(hydroxyimino)methyl]-1,3-thiazol-2-yl}piperidine-1-carboxylate (250 mg) and 1-(2-methoxyethoxy)-3-vinylbenzene were reacted analogously to I-31 (Processes D and E). This gave tert-butyl 4-(4-{5-[3-(2-methoxyethoxy)phenyl]-4,5-dihydro-1,2-oxazol-3-yl}-1,3-thiazol-2-yl)piperidine-1-carboxy late (170 mg)
$^1$H NMR (DMSO-d$_6$): $\delta_{ppm}$: 8.00 (s, 1H), 7.29 (t, 1H), 7.10-6.80 (m, 3H), 5.68 (dd, 1H), 4.15-3.95 (m, 4H), 3.84 (dd, 1H), 3.70-3.60 (m, 2H), 3.45-3.20 (m), 2.95-2.80 (m, 2H), 2.08-1.98 (m, 2H), 1.63-1.48 (m, 2H), 1.40 (s, 9H)
The 1-(2-methoxyethoxy)-3-vinylbenzene reactant was synthesized proceeding from 3-(2-methoxyethoxy)benzaldehyde by methods familiar to those skilled in the art (Wittig reaction: *Chem. Rev.* 1989, 89, 863-927).

Processes G and H

2-[3,5-Bis(difluoromethyl)-1H-pyrazol-1-yl]-1-[4-(4-{5-[3-(2-methoxyethoxy)phenyl]-4,5-dihydro-1,2-oxazol-3-yl}-1,3-thiazol-2-yl)piperidin-1-yl]ethanone (I-28)

tert-Butyl 4-(4-{5-[3-(2-methoxyethoxy)phenyl]-4,5-dihydro-1,2-oxazol-3-yl}-1,3-thiazol-2-yl)piperidine-1-carboxylase (279 mg) was reacted analogously to I-31 (Processes G and H). This gave 2-[3,5-bis(difluoromethyl)-1H-pyrazol-1-yl]-1-[4-(4-{5-[3-(2-methoxyethoxy)-phenyl]-4,5-dihydro-1,2-oxazol-3-yl}-1,3-thiazol-2-yl)piperidin-1-yl]ethanone (180 mg).

2-[3,5-Bis(difluoromethyl)-1H-pyrazol-1-yl]-1-(4-{4-[5-(2-chloro-6-hydroxyphenyl)-4,5-dihydro-1,2-oxazol-3-yl]-1,3-thiazol-2-yl}piperidin-1-yl)ethanone (I-54)

Processes D and E tert-Butyl 4-{4-[5-(2-chloro-6-hydroxyphenyl)-4,5-dihydro-1,2-oxazol-3-yl]-1,3-thiazol-2-yl}piperidine-1-carboxylate (X-a-12)

To a solution of tert-butyl 4-{4-[(hydroxyimino)methyl]-1,3-thiazol-2-yl}piperidine-1-carboxylate (400 mg) in ethyl acetate (10 ml) was added N-chlorosuccinimide (206 mg). The reaction mixture is stirred at reflux for 30 min. To the reaction mixture were added 3-chloro-2-vinylphenol (397 mg) and potassium hydrogencarbonate (257 mg) at room temperature, and then one drop of water. After stirring at room temperature overnight, the reaction mixture was admixed with ethyl acetate and water and extracted with ethyl acetate. The organic extracts were dried over sodium sulphate and concentrated under reduced pressure. The residue was purified by chromatography. This gave tert-butyl 4-{4-[5-(2-chloro-6-hydroxyphenyl)-4,5-dihydro-1,2-oxazol-3-yl]-1,3-thiazol-2-yl}piperidine-1-carboxylate (345 mg).

$^1$H NMR (DMSO-d$_6$): $\delta_{ppm}$: 7.95 (s, 1H), 7.18 (t, 1H), 6.92 (d, 1H), 6.82 (d, 1H), 6.17 (dd, 1H), 4.1-3.95 (m), 3.30-3.15 (m), 3.05-2.75 (m, 2H), 2.08-2.0 (m, 2H), 1.62-1.50 (m, 2H), 1.40 (s, 9H)

In this case too, the 3-chloro-2-vinylphenol reactant was synthesized proceeding from 2-chloro-6-hydroxybenzaldehyde by synthesis methods familiar to those skilled in the an (Wittig reaction: *Chem. Rev.* 1989, 89, 863-927).

Processes G and H

2-[3,5-Bis(difluoromethyl)-1H-pyrazol-1-yl]-1-(4-{4-[5-(2-chloro-6-hydroxyphenyl)-4,5-dihydro-1,2-oxazol-3-yl]-1,3-thiazol-2-yl}piperidin-1-yl)ethanone (I-54)

To a solution of tert-butyl 4-{4-[5-(2-chloro-6-hydroxyphenyl)-4,5-dihydro-1,2-oxazol-3-yl]-1,3-thiazol-2-yl}piperidine-1-carboxylate (346 mg) in dichloromethane was added dropwise, at 0° C., a 4 molar solution of hydrogen chloride (4.0 eq.) in 1,4-dioxane. The reaction mixture was stirred at 0° C. and then gradually warmed to room temperature. After stirring for 5 hours, the solvent and excess hydrogen chloride were removed. This gave 4-{4-[5-(2-chloro-6-hydroxyphenyl)-4,5-dihydro-1,2-oxazol-3-yl]-1,3-thiazol-2-yl}piperidinium chloride (XII-9).

To a solution of [3,5-bis-(difluoromethyl)-1H-pyrazol-1-yl]acetic acid (177 mg) in dichloromethane (40 ml) are added, at 0° C., oxalyl chloride (290 mg) and one drop of N,N-dimethylformamide. The reaction mixture is stirred at room temperature for 2 hours. The solvent and the excess reagent are removed under reduced pressure. The solid residue is again dissolved in dichloromethane and, at 0° C., added dropwise to a solution of 4-{4-[5-(2-chloro-6-hydroxyphenyl)-4,5-dihydro-1,2-oxazol-3-yl]-1,3-thiazol-2-yl}piperidinium chloride and triethylamine (5.0 eq.) in dichloromethane (25 ml). The reaction mixture is stirred at room temperature overnight. Then it is admixed with concentrated sodium hydrogencarbonate solution, and the aqueous phase is removed and extracted with ethyl acetate. The combined organic phases are dried over sodium sulphate and concentrated. Purification by column chromatography gives 2-[3,5-bis(difluoromethyl)-1H-pyrazol-1-yl]-1-(4-{4-[5-(2-chloro-6-hydroxyphenyl)-4,5-dihydro-1,2-oxazol-3-yl]-1,3-thiazol-2-yl}piperidin-1-yl)ethanone (110 mg).

$^1$H NMR (DMSO-d$_6$): $\delta_{ppm}$: 10.28 (s, 1H), 7.98 (s, 1H), 7.30-6.80 (m, 6H), 6.17 (dd, 1H), 5.40 (dd, 2H), 4.36 (d, 1H), 3.97 (d, 1H), 3.71-3.55 (m, 2H), 3.32-3.24 (m, 1H), 2.84 (t, 1H), 2.16-2.08 (m, 2H), 1.85-1.75 (m, 1H), 1.62-1.53 (m, 1H).

Log P (HCOOH): 2.94

1-[4-(4-{5-[2-(Allyloxy)-6-chlorophenyl]-4,5-dihydro-1,2-oxazol-3-yl}-1,3-thiazol-2-yl)piperidin-1-yl]-2-[3,5-bis(difluoromethyl)-1H-pyrazol-1-yl]ethanone (I-51)

To a solution of 2-[3,5-bis(difluoromethyl)-1H-pyrazol-1-yl]-1-(4-{4-[5-(2-chloro-6-hydroxyphenyl)-4,5-dihydro-1,2-oxazol-3-yl]-1,3-thiazol-2-yl}piperidin-1-yl)ethanone (39 mg) and potassium carbonate (47 mg) in acetone (5 ml) is added, at room temperature, allyl bromide (33 mg). The reaction mixture is stirred at reflux for 5 h. Then the mixture is admixed with water and extracted with ethyl acetate. The combined organic phases are dried over sodium sulphate and concentrated. Purification by column chromatography gives 1-[4-(4-{5-[2-(allyloxy)-6-chlorophenyl]-4,5-dihydro-1,2-oxazol-3-yl}-1,3-thiazol-2-yl)piperidin-1-yl]-2-[3,5-bis(difluoromethyl)-1H-pyrazol-1-yl]ethanone (26 mg).

2-[3,5-Bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone (I-49)

To a solution of 2-[3,5-bis(difluoromethyl)-1H-pyrazol-1-yl]-1-(4-{4-[5-(2-chloro-6-hydroxyphenyl)-4,5-dihydro-1,2-oxazol-3-yl]-1,3-thiazol-2-yl}piperidin-1-yl)ethanone (33 mg) and potassium carbonate (12 mg) in N,N-dimethylformamide (5 ml) are added, at room temperature, potassium iodide (5 mg) and 3-bromoprop-1-yne (11 mg). The reaction mixture is stirred at 80° C. for 9 h. Then the mixture is admixed with dilute hydrochloric acid and extracted with ethyl acetate. The combined organic phases are dried over sodium sulphate and concentrated. Purification by column chromatography gives 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone (19 mg).

2-[3,5-Bis(difluoromethyl)-1H-pyrazol-1-yl]-1-[4-(4-{5-[2-chloro-6-(2-methoxyethoxy)phenyl]-4,5-dihydro-1,2-oxazol-3-yl}-1,3-thiazol-2-yl)piperidin-1-yl]ethanone (I-50)

To a solution of 2-[3,5-bis(difluoromethyl)-1H-pyrazol-1-yl]-1-(4-{4-[5-(2-chloro-6-hydroxyphenyl)-4,5-dihydro-1,2-oxazol-3-yl]-1,3-thiazol-2-yl}piperidin-1-yl)ethanone (39 mg) and potassium carbonate (47 mg) in N,N-dimethylformamide (5 ml) are added, at room temperature, 1-bromo-2-methoxyethane (38 mg) and potassium iodide (1.1 mg). The reaction mixture is stirred at 80° C. for 3 h. Then the mixture is admixed with water and extracted with ethyl acetate. The combined organic phases are dried over sodium sulphate and concentrated. Purification by column chromatography gives 2-[3,5-bis(difluoromethyl)-1H-pyrazol-1-yl]-1-[4-(4-{-5-[2-chloro-6-(2-methoxyethoxy)-phenyl]-4,5-dihydro-[1,2-oxazol-3-yl}-1,3-thiazol-2-yl)piperidin-1-yl]ethanone (17 mg).

2-(3-[2-(1-{[3,5-Bis(difluoromethyl)-1H-pyrazol-1-yl]acetyl}piperidin-4-yl)-1,3-thiazol-4-yl]-4,5-dihydro-1,2-oxazol-5-yl}-3-fluorobenzaldehyde (I-17)

3-Fluoro-2-vinylbenzaldehyde

To a solution of 1-bromo-3-fluoro-2-vinylbenzene (900 mg) in THF (40 ml) was added dropwise, at −78° C., n-butyllithium (3.4 ml 1.6 M/hexane). After 60 minutes, N,N-dimethylformamide (0.69 ml) was added dropwise at −78° C. After stirring at −78° C. for 60 minutes, the reaction mixture was admixed with water and then warmed to room temperature. Then the mixture was admixed with water and extracted with ethyl acetate. The combined organic phases were dried over sodium sulphate and concentrated. Purification by column chromatography gives 3-fluoro-2-vinylbenzaldehyde (160 mg).

In this case too, the 1-bromo-3-fluoro-2-vinylbenzene reactant was synthesized proceeding from 2-bromo-6-fluorobenzaldehyde by synthesis methods familiar to those skilled in the an (Wittig reaction: *Chem. Rev.* 1989, 89, 863-927).

Processes D and E tert-Butyl 4-{4-[5-(2-fluoro-6-formylphenyl)-4,5-dihydro-1,2-oxazol-3-yl]-1,3-thiazol-2-yl}piperidine-1-carboxylate (X-a-13)

To a solution of tert-butyl 4-{4-[(hydroxyimino)methyl]-1,3-thiazol-2-yl}piperidine-1-carboxylate (166 mg) in ethyl acetate (10 ml) was added N-chlorosuccinimide (85.5 mg). The reaction mixture was stirred at reflux for 30 min. To this reaction mixture were added, at room temperature, 3-fluoro-2-vinylbenzaldehyde (160 mg) and potassium hydrogencarbonate (106.7 mg), and then one drop of water. After stirring at room temperature overnight, the reaction mixture was admixed with ethyl acetate and water and extracted with ethyl acetate. The organic extracts were dried over sodium sulphate and concentrated under reduced pressure. The residue was purified by chromatography. This gave tert-butyl 4-{4-[5-(2-fluoro-6-formylphenyl)-4,5-dihydro-1,2-oxazol-3-yl]-1,3-thiazol-2-yl}piperidine-1-carboxylate (110 mg)

$^1$H NMR (DMSO-$d_6$): 10.26 (s, 1H), 8.03 (s, 1H), 7.76 (dd, 1H), 7.68-7.64 (m, 1H), 7.62-7.57 (m, 1H), 6.55 (t, 1H), 4.08-3.90 (m, 3H), 3.53 (dd, 1H), 3.40-3.30 (m, 1H), 2.05-2.00 (m, 2H), 1.62-1.52 (m, 2H), 1.40 (s, 9H), log P (HCO2H): 3.62

Processes G and H

2-{3-[2-(1-{[3,5-Bis(difluoromethyl)-1H-pyrazol-1-yl]acetyl}piperidin-4-yl)-1,3-thiazol-4-yl]-4,5-dihydro-1,2-oxazol-5-yl}-3-fluorobenzaldehyde (I-17)

To a solution of tert-butyl 4-{4-[5-(2-fluor-6-formylphenyl)-4,5-dihydro-1,2-oxazol-3-yl]-1,3-thiazol-2-yl}piperidine-1-carboxylate (112 mg) in dichloromethane was added dropwise, at 0° C., a 4 molar solution of hydrogen chloride (4.0 eq.) in 1,4-dioxane. The reaction mixture was stirred at 0° C. and then gradually warmed to room temperature. After stirring for 5 hours, the solvent and excess hydrogen chloride were removed. This gave 4-{4-[5-(2-fluoro-6-formylphenyl)-4,5-dihydro-1,2-oxazol-3-yl]-1,3-thiazol-2-yl}piperidinium chloride (XII-10).

To a solution of [3,5-bis-(difluoromethyl)-1H-pyrazol-1-yl]acetic acid (58 mg) in dichloromethane (20 ml) were added, at 0° C., oxalyl chloride (94.5 mg) and one drop of N,N-dimethylformamide. The reaction mixture was stirred at room temperature for 2 hours. The solvent and the excess reagent were removed under reduced pressure. The solid residue was again dissolved in dichloromethane (5 ml) and, at 0° C., added dropwise to a solution of 4-{4-[5-(2-fluoro-6-formylphenyl)-4,5-dihydro-1,2-oxazol-3-yl]-1,3-thiazol-2-yl}piperidinium chloride and triethylamine (5.0 eq.) in dichloromethane (15 ml). The reaction mixture was stirred at room temperature overnight. Then it was admixed with concentrated sodium hydrogencarbonate solution, and the aqueous phase was removed and extracted with ethyl acetate. The combined organic phases were dried over sodium sulphate and concentrated. Purification by column chromatography gave 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-fluorobenzaldehyde (55 mg).

EXAMPLES

TABLE 1

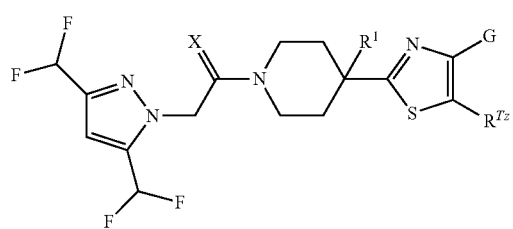

(I)

In Table 1, the G group occurs especially in the specifications G3 and G4:

| Ex. | X | R$^1$ | G | R$^2$ | R$^3$ | R$^{Tz}$ | logp |
|---|---|---|---|---|---|---|---|
| I-1 | O | H | G3 | phenyl | H | H | 3.17[b]; 3.11[c] |
| I-2 | O | H | G3 | 2,6-difluorophenyl | H | H | 3.14[b] |
| I-3 | O | H | G4 | phenyl |  | H | 3.66[b] |
| I-4 | O | Fluoro | G3 | 2-fluorophenyl |  | H | 3.49[b] |
| I-5 | O | Fluoro | G3 | phenyl |  | H | 3.41[b] |
| I-6 | O | Fluoro | G3 | 2,6-difluorophenyl | H | H | 3.43[b]; 3.34[c] |
| I-7 | O | H | G3 | 2-acetylphenyl | H | H | 3.08[b] |
| I-8 | O | H | G3 | 3-acetylphenyl | H | H | 2.78[b] |
| I-9 | O | H | G3 | 2-hydroxyphenyl | H | H | 2.58[a]; 2.6[c] |

-continued

| Ex. | X | R¹ | G | R² | R³ | R^Tz | logp |
|---|---|---|---|---|---|---|---|
| I-10 | O | H | G3 | 2-nitrophenyl | H | H | 3.19[b] |
| I-11 | O | H | G3 | 2-[(2-methoxyethoxy)methyl]phenyl | H | H | 3.21[b] |
| I-12 | O | H | G3 | 2-[(ethylsulphanyl)methyl]phenyl | H | H | 3.9[b] |
| I-13 | O | H | G3 | 2-[(cyclopropylmethoxy)carbonyl]phenyl | H | H | 3.92[c]; 3.99[b] |
| I-14 | O | H | G3 | 2-(allyloxy)phenyl | H | H | 3.63[b]; 3.65[c] |
| I-15 | O | H | G3 | 3-(but-2-yn-1-yloxy)phenyl | H | H | 3.33[c]; 3.29[a] |
| I-16 | O | H | G3 | 2-(butoxymethyl)phenyl | H | H | 4.24[b] |
| I-17 | O | H | G3 | 2-fluoro-6-formylphenyl | H | H | 2.82[c]; 2.92[b] |
| I-18 | O | H | G3 | 2-[(2-methylprop-2-en-1-yl)oxy]phenyl | H | H | 3.96[b]; 3.92[c] |
| I-19 | O | H | G3 | 2-(2-methoxyethoxy)phenyl | H | H | 3.18[c]; 3.26[b] |
| I-20 | O | H | G3 | 2-[(3-methylbut-2-en-1-yl)oxy]phenyl | H | H | 4.19[b]; 4.11[c] |
| I-21 | O | H | G3 | 3-(prop-2-yn-1-yloxy)phenyl | H | H | 3.16[c]; 3.24[a] |
| I-22 | O | H | G3 | 4-(prop-2-yn-1-yloxy)phenyl | H | H | 3.14[a]; 3.08[c] |
| I-23 | O | H | G3 | 3-formylphenyl | H | H | 2.78[b] |
| I-24 | O | H | G3 | 2-(cyclohexylmethoxy)phenyl | H | H | 4.9[a]; 4.9[c] |
| I-25 | O | H | G3 | 2-(pent-2-yn-1-yloxy)phenyl | H | H | 3.91[b] |
| I-26 | O | H | G3 | 2-formylphenyl | H | H | 2.98[b] |
| I-27 | O | H | G3 | 2-(cyclopropylcarbamoyl)phenyl | H | H | 2.64[b] |
| I-28 | O | H | G3 | 3-(2-methoxyethoxy)phenyl | H | H | 3.03[b]; 3.04[c] |
| I-29 | O | H | G3 | 2-(but-2-yn-1-yloxy)-6-fluorophenyl | H | H | 3.46[a]; 3.42[c] |
| I-30 | O | H | G3 | 2-fluoro-6-(prop-2-yn-1-yloxy)phenyl | H | H | 3.18[a]; 3.15[c] |
| I-31 | O | H | G4 | 2-formylphenyl | | H | 3.25[b] |
| I-32 | O | H | G3 | 2-[(cyclohexylcarbonyl)oxy]phenyl | H | H | 4.27[a]; 4.19[c] |
| I-33 | O | H | G3 | 2-[(cyclopropylcarbonyl)oxy]phenyl | H | H | 3.28[c]; 3.34[a] |
| I-34 | O | H | G3 | 3-(pent-2-yn-1-yloxy)phenyl | H | H | 3.74[c]; 3.83[a] |
| I-35 | O | H | G3 | 2-(but-2-yn-1-yloxy)phenyl | H | H | 3.55[c]; 3.65[a] |
| I-36 | O | H | G3 | 2-[(3,3,3-trifluoropropanoyl)oxy]phenyl | H | H | 9.43[a]; 3.52[c] |
| I-37 | O | H | G3 | 2-[(methylsulphonyl)amino]phenyl | H | H | 2.51[b] |
| I-38 | O | H | G3 | 2-ethynylphenyl | H | H | 3.36[b] |
| I-39 | O | H | G3 | 2-(prop-2-yn-1-yloxy)phenyl | H | H | 3.23[c]; 3.28[a] |
| I-40 | O | H | G3 | 4-[(methylsulphonyl)amino]phenyl | H | H | 2.41[b] |
| I-41 | O | H | G3 | 2-aminophenyl | H | H | 2.71[c]; 2.7[a] |
| I-42 | O | H | G3 | 3-hydroxyphenyl | H | H | 2.45[c]; 2.43[a] |
| I-43 | O | H | G3 | 2-(methoxycarbonyl)phenyl | H | H | 3.32[b] |
| I-44 | O | H | G3 | 2-(chloromethyl)phenyl | H | H | 3.36[b] |
| I-45 | O | H | G3 | 2-(hydroxymethyl)phenyl | H | H | 2.45[b] |
| I-46 | O | H | G3 | 2-(methoxycarbonyl)phenyl | H | Chloro | 3.98[b] |
| I-47 | O | H | G3 | 4-(pent-2-yn-1-yloxy)phenyl | H | H | 3.74[c]; 3.76[a] |
| I-48 | O | H | G3 | 4-(but-2-yn-1-yloxy)phenyl | H | H | 3.42[c]; 3.43[a] |
| I-49 | O | H | G3 | 2-chloro-6-(prop-2-yn-1-yloxy)phenyl | H | H | 3.5[b]; 3.34[c] |
| I-50 | O | H | G3 | 2-chloro-6-(2-methoxyethoxy)phenyl | H | H | 3.36[b] |
| I-51 | O | H | G3 | 2-(allyloxy)-6-chlorophenyl | H | H | 3.71[c]; 3.82[b] |
| I-52 | O | H | G3 | 2-[(2,2,2-trifluoroethoxy)methyl]phenyl | H | H | 3.6[c]; 3.4[b] |
| I-53 | O | H | G3 | 2-[(ethylsulphonyl)methyl]phenyl | H | H | 2.76[b] |
| I-54 | O | H | G3 | 2-chloro-6-hydroxyphenyl | H | H | 2.94[b] |

G3 means

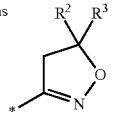

G4 means:

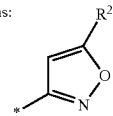

The logP values were determined according to EEC Directive 79/831 Annex V.A8 by HPLC (High-Performance Liquid Chromatography) on reversed-phase columns (C 18) by the following methods:

[a]The determination is effected in the acidic range at pH 2.3 using 0.1% aqueous phosphoric acid and acetonitrile as eluents; linear gradient from 10% acetonitrile to 95% acetonitrile.

[b]The LC-MS determination in the acidic range is effected at pH 2.7 using 0.1% aqueous formic acid and acetonitrile (contains 0.1% formic acid) as eluents; linear gradient from 10% acetonitrile to 95% acetonitrile.

[c]The LC-MS determination in the neutral range is effected at pH 7.8 using 0.001 molar aqueous ammonium hydrogencarbonate solution and acetonitrile as eluents; linear gradient from 10% acetonitrile to 95% acetonitrile.

The calibration is effected with unbranched alkan-2-ones (having 3 to 16 carbon atoms) with known log P values (determination of the log P values using the retention times by linear interpolation between two successive alkanones).

The lambda-max values were determined in the maxima of the chromatographic signals using the UV spectra from 200 nm to 400 nm.

NMR Data of Selected Examples

| Ex. | NMR Data |
|---|---|
| I-1 | $^1$H NMR: $\delta_{ppm}$: 1.63 (m, 1H), 1.79 (m, 1H), 2.18-2.05 (m, 2H), 2.88 (m, 1H), 3.42-3.20 (m, 3H), 3.87 (dd, 1H), 3.98 (m, 1H), 4.32 (m, 1H), 5.35 (bs, 2H), 5.72 (dd, 1H), 6.85 (s, 1H), 6.97 (t, 1H), 7.14 (t, 1H), 7.40-7.30 (m, 5H), 7.97 (s, 1H) |
| I-2 | $^1$H NMR: $\delta_{ppm}$: 1.58 (m, 1H), 1.83 (m, 1H), 2.18-2.07 (m, 2H), 2.85 (m, 1H), 3.25 (m, 1H), 3.41 (m, 1H), 3.52 (dd, 1H), 3.90 (dd, 1H), 3.98 (m, 1H), 4.36 (m, 1H), 5.35 (d, 1H), 5.47 (d, 1H), 6.01 (dd, 1H), 6.90 (s, 1H), 7.02 (t, 1H), 7.18 (t, 1H), 7.19-7.12 (m, 2H), 7.50 (m, 1H), 8.03 (s, 1H) |
| I-3 | $^1$H NMR: $\delta_{ppm}$: 1.66 (m, 1H), 1.85 (m, 1H), 2.22-2.10 (m, 2H), 2.88 (dd, 1H), 3.50-3.45 (m, 2H), 4.00 (d, 1H), 4.39 (d, 1H), 5.37 (d, 1H), 5.45 (d, 1H), 6.91 (s, 1H), 7.03 (t, 1H), 7.19 (t, 1H), 7.44 (s, 1H), 7.60-7.53 (m, 3H), 7.96 (dd, 2H), 8.23 (s, 1H) |
| I-4 | $^1$H NMR: $\delta_{ppm}$: 2.45-2.05 (m, 4H), 3.10 (m, 1H), 3.44 (dd, 1H), 3.47 (m, 1H), 3.98-3.90 (m, 2H), 4.28 (m, 1H), 5.40 (d, 1H), 5.51 (d, 1H), 5.94 (dd, 1H), 6.91 (s, 1H), 7.03 (t, 1H), 7.18 (t, 1H), 7.32-7.20 (m, 2H), 7.48-7.38 (m, 2H), 8.24 (s, 1H) |
| I-5 | $^1$H NMR: $\delta_{ppm}$: 2.45-2.05 (m, 4H), 3.11 (m, 1H), 3.38 (dd, 1H), 3.48 (m, 1H), 3.95-3.86 (m, 2H), 4.26 (m, 1H), 5.39 (d, 1H), 5.50 (d, 1H), 5.76 (dd, 1H), 6.91 (s, 1H), 7.03 (t, 1H), 7.18 (t, 1H), 7.42-7.33 (m, 5H), 8.22 (s, 1H) |
| I-6 | $^1$H NMR (CD$_3$CN): $\delta_{ppm}$: 2.50-2.10 (m, 4H), 3.18 (m, 1H), 3.55 (m, 1H), 3.59 (dd, 1H), 3.89-3.78 (m, 2H), 4.36 (m, 1H), 5.22 (d, 1H), 5.29 (d, 1H), 6.07 (dd, 1H), 6.79 (t, 1H), 6.83 (s, 1H), 6.91 (t, 1H), 7.07-6.99 (m, 2H), 7.42 (m, 1H), 7.88 (s, 1H) |

The chemical NMR shifts in ppm were measured at 400 MHz, unless stated otherwise in the solvent DMSO-d$_6$ with tetramethylsilane as the internal standard.
The following abbreviations describe the signal splitting:
b = broad, s = singlet, d = doublet, t = triplet, q = quadruplet, m = multiplet NMR Data of Selected Examples
NMR Peak List Procedure The 1H NMR data of selected examples are noted in the form of 1H NMR peak lists. For each signal peak, the δ value in ppm and the signal intensity are listed in brackets.

Ex. I-8, Solvent: DMSO-d$_6$ 8.0369 (5.64); 7.953 (3.33); 7.9506 (3.17); 7.9343 (1.15); 7.9312 (1.42); 7.6713 (1.04); 7.652 (1.46); 7.5832 (1.24); 7.5643 (1.87); 7.5446 (0.75); 7.307 (1); 7.1737 (2.29); 7.1587 (1.17); 7.0404 (1.14); 7.0226 (2.57); 6.9004 (2.47); 6.8868 (1.32); 5.8661 (0.82); 5.8458 (1); 5.8389 (0.98); 5.8188 (0.86); 5.4508 (0.47); 5.408 (1.81); 5.3671 (1.73); 5.3247 (0.46); 4.3643 (0.54); 4.33 (0.57); 4.0573 (0.63); 4.0395 (1.85); 4.0217 (1.88); 4.0039 (0.73); 3.984 (0.53); 3.9632 (1.19); 3.9508 (0.62); 3.9359 (1.24); 3.92 (1.23); 3.8927 (1.02); 3.4659 (1.22); 3.4167 (1.62); 3.4071 (0.58); 3.3936 (1.63); 3.3881 (1.26); 3.3735 (1.77); 3.3194 (308.6); 3.2418 (0.85); 2.891 (0.55); 2.8724 (0.42); 2.8441 (0.72); 2.8149 (0.43); 2.7325 (0.4); 2.6704 (0.34); 2.5949 (16); 2.5522 (0.37); 2.5404 (0.69); 2.5235 (1.54); 2.5102 (19.34); 2.5059 (35.33); 2.5015 (45.46); 2.4971 (31.98); 2.4929 (15.8); 2.3283 (0.36); 2.1377 (0.55); 2.1018 (1.05); 2.0693 (0.92); 1.9871 (8.04); 1.8117 (0.49); 1.7902 (0.44); 1.5915 (0.45); 1.5827 (0.5); 1.5611 (0.46); 1.5519 (0.44); 1.398 (2.53); 1.2365 (0.34); 1.193 (2.23); 1.1752 (4.38); 1.1575 (2.15); 0.0078 (0.39); −0.0002 (7.25); −0.0082 (0.34)

Ex. I-9, Solvent: DMSO-d$_6$ 9.7066 (7.97); 8.0287 (0.34); 8.0022 (10.13); 7.3071 (1.98); 7.2167 (2.69); 7.1976 (2.79); 7.1737 (4.5); 7.1591 (2.52); 7.1535 (1.76); 7.1494 (1.48); 7.1338 (2.64); 7.1147 (1.75); 7.1106 (1.5); 7.0405 (2.26); 7.0231 (4.87); 6.8986 (5.15); 6.8873 (2.7); 6.8638 (3.65); 6.8438 (3.23); 6.8125 (1.98); 6.7939 (3.39); 6.7754 (1.61); 5.8556 (1.76); 5.8368 (2.06); 5.8279 (2); 5.8092 (1.77); 5.4492 (0.98); 5.4074 (3.65); 5.3673 (3.74); 5.3251 (0.97); 4.3592 (1.22); 4.3252 (1.24); 4.0571 (1.37); 4.0393 (3.86); 4.0215 (3.89); 4.0038 (1.48); 3.9781 (1.2); 3.9449 (1.26); 3.8484 (1.8); 3.8204 (2.02); 3.8055 (2.29); 3.7778 (1.96); 3.4036 (1.2); 3.3939 (1.1); 3.3846 (1.56); 3.3756 (2.26); 3.3661 (1.82); 3.3464 (2.39); 3.3065 (242.8); 3.2791 (3.62); 3.2656 (2.17); 3.2552 (2.76); 3.2364 (2.8); 3.2685 (0.84); 2.8404 (1.49); 2.8107 (0.85); 2.6692 (0.58); 2.6648 (0.47); 2.5392 (1.55); 2.5046 (63.17); 2.5003 (76.51); 2.4964 (53.38); 2.3316 (0.41); 2.327 (0.5); 2.1301 (1.13); 2.0982 (2.27); 2.0692 (1.31); 1.9869 (16); 1.8411 (0.47); 1.8172 (0.97); 1.811 (1.01); 1.7889 (0.92); 1.759 (0.37); 1.6137 (0.42); 1.6042 (0.48); 1.5829 (0.94); 1.5746 (0.98); 1.5538 (0.95); 1.5452 (0.87); 1.5238 (0.37); 1.3981 (0.73); 1.1928 (4.43); 1.175 (8.57); 1.1572 (4.18); −0.0002 (2.26)

Ex. I-10, Solvent: DMSO-d$_6$ 9.9026 (0.53); 8.7786 (0.82); 8.6473 (0.5); 8.4336 (0.4); 8.1699 (2.2); 8.1671 (2.25); 8.1494 (2.4); 8.1466 (2.37); 8.0449 (8.69); 7.8303 (0.96); 7.8276 (0.99); 7.81 (2.12); 7.7925 (1.53); 7.7897 (1.47); 7.6818 (2.46); 7.665 (1.83); 7.6621 (1.84); 7.6401 (1.46); 7.6366 (1.32); 7.6191 (2.13); 7.6013 (1.16); 7.5979 (1.04); 7.305 (1.64); 7.1717 (3.75); 7.1581 (1.97); 7.0384 (1.89); 7.0221 (4.3); 6.8984 (4.07); 6.8862 (2.33); 6.2689 (1.29); 6.2533 (1.45); 6.2409 (1.46); 6.2251 (1.32); 5.7475 (1.13); 5.4471 (0.79); 5.4048 (2.82); 5.365 (2.87); 5.3233 (0.77); 4.3558 (0.94); 4.3252 (1.02); 4.3078 (0.59); 4.2898 (0.36); 4.1407 (1.39); 4.1124 (1.59); 4.0965 (1.79); 4.0684 (1.57); 4.0573 (1.34); 4.0395 (3.7); 4.0217 (3.75); 4.0039 (1.38); 3.9768 (0.91); 3.9436 (0.96); 3.4422 (1.76); 3.4264 (1.82); 3.4113 (0.58); 3.3982 (2.02); 3.3825 (2.38); 3.3737 (1.46); 3.3641 (0.94); 3.3541 (0.78); 3.3445 (1.03); 3.3352 (0.97); 3.3023 (178.37); 3.2798 (2.37); 3.2613 (1.61); 3.2312 (0.85); 3.0381 (0.37); 2.8638 (0.7); 2.8507 (0.64); 2.8327 (1.16); 2.8038 (0.66); 2.6696 (0.41); 2.6649 (0.32); 2.5396 (0.72); 2.5092 (23.41); 2.5049 (43.1); 2.5005 (56.19); 2.4961 (40.14); 2.4918 (20.08); 2.3319 (0.33); 2.3275 (0.41); 2.1465 (0.37); 2.1243 (0.96); 2.0891 (1.7); 2.0702 (0.87); 2.0549 (0.95); 1.9871 (16); 1.8344 (0.43); 1.8118 (0.79); 1.8063 (0.8); 1.7814 (0.74); 1.6064 (0.38); 1.5981 (0.43); 1.5768 (0.77); 1.5683 (0.78); 1.5476 (0.73); 1.5382 (0.67); 1.3977 (1.14); 1.3202 (0.35); 1.3026 (0.69); 1.2848 (0.36); 1.2363 (0.38); 1.193 (4.46); 1.1752 (8.83); 1.1574 (4.38); 0.0596 (1.49); −0.0002 (3.18)

Ex. I-11, Solvent: CD$_3$CN 7.6716 (4.88); 7.4701 (1.37); 7.4579 (1.37); 7.4558 (1.26); 7.3757 (0.71); 7.366 (1.87); 7.3544 (2); 7.3193 (1.14); 7.3079 (1.33); 7.2958 (0.49); 6.9878 (1.11); 6.898 (2.29); 6.8776 (1.16); 6.8311 (2.32); 6.8083 (1.15); 6.7866 (2.38); 6.6957 (1.19); 5.9944 (1.02); 5.98 (1.14); 5.9761 (1.13); 5.9617 (1.04); 5.2629 (0.75); 5.2346 (2.39); 5.203 (2.4); 5.1748 (0.78); 4.6414 (1.85); 4.6422 (2.48); 4.534 (2.57); 4.5148 (1.92); 4.4734 (0.56); 4.4508 (0.59); 4.0646 (0.52); 4.0527 (0.52); 3.9375 (1.16); 3.919 (1.47); 3.9088 (1.74); 3.8903 (1.81); 3.633 (0.33); 3.6312 (0.34); 3.622 (0.93); 3.6155 (1.02); 3.6127 (1.16); 3.6068 (1.68); 3.6003 (1.56); 3.593 (1.26); 3.5821 (0.5); 3.575 (0.41); 3.5279 (2.27); 3.5209 (2.9); 3.5178 (1.41); 3.5142 (1.25); 3.5114 (1.13); 3.3636 (0.49); 3.3509 (0.52); 3.3445 (1); 3.3381 (0.53); 3.3254 (0.53); 3.3069 (0.46); 3.3023 (0.6); 3.2958 (16); 3.283 (1.39); 3.2669 (1.45); 3.2594 (0.49); 3.2527 (1.3); 3.2383 (1.21); 3.224 (1.19); 2.8775 (0.38); 2.873 (0.42); 2.8557 (0.73); 2.8523 (0.75); 2.8351 (0.45); 2.8306 (0.41); 2.201 (69.88); 2.1761 (1.1); 2.1451 (0.6); 2.1232 (0.61); 1.9733 (2.23); 1.9665 (1.21); 1.9583 (0.58); 1.9504 (8.08); 1.9463 (14.95); 1.9422 (21.76); 1.9381 (14.82); 1.934 (7.55); 1.8641 (0.53); 1.8576 (0.54); 1.8431 (0.5); 1.8364 (0.52); 1.6993 (0.54); 1.6927 (0.57); 1.6786 (0.53); 1.672 (0.51); 1.4358 (0.96); 1.2157 (0.58); 1.2039 (1.15); 1.192 (0.58); 1.1138 (0.43); −0.0002 (3.37)

Ex. I-12, Solvent: DMSO-d$_6$ 8.0249 (9.55); 8.018 (0.5); 7.3706 (1.21); 7.3647 (1.69); 7.348 (2.04); 7.3268 (1.05); 7.3187 (1.26); 7.3109 (2.51); 7.3054 (3.71); 7.3007 (3.98); 7.2948 (1.66); 7.2903 (3.15); 7.2842 (4.3); 7.2772 (1.28); 7.2741 (1.16); 7.2685 (1.2); 7.2553 (0.42); 7.1752 (3.67); 7.1646 (1.82); 7.042 (1.78); 7.0286 (4.12);

6.9069 (3.51); 6.8928 (2); 6.0983 (1.32); 6.0778 (1.61); 6.0706 (1.59); 6.0501 (1.38); 5.4543 (0.81); 5.4117 (2.73); 5.37 (2.71); 5.3271 (0.8); 4.3626 (0.8); 4.3301 (0.86); 4.0165 (1.37); 3.9887 (2.07); 3.9734 (2.27); 3.9457 (2.23); 3.9192 (1.95); 3.8865 (3.67); 3.8314 (3.75); 3.7985 (1.95); 3.5567 (0.35); 3.5284 (0.34); 3.5202 (0.37); 3.5117 (0.33); 3.4896 (0.71); 3.4738 (0.77); 3.4573 (1.27); 3.4434 (1.57); 3.4376 (1.71); 3.3605 (1918.14); 3.3154 (7.54); 3.2944 (5.31); 3.2716 (3.59); 3.2513 (2.77); 3.2419 (1.37); 3.236 (1.44); 3.2 (0.62); 3.153 (0.39); 3.1441 (0.39); 3.1275 (0.39); 3.1088 (0.34); 3.0997 (0.34); 3.0366 (0.38); 2.8643 (0.67); 2.8337 (1.11); 2.8064 (0.66); 2.6818 (0.5); 2.6773 (0.95); 2.6728 (1.31); 2.6682 (0.99); 2.6636 (0.52); 2.5428 (0.86); 2.5258 (3.63); 2.5127 (71.69); 2.5082 (143.99); 2.5036 (190.58); 2.499 (138.34); 2.4945 (68.05); 2.4728 (8.16); 2.4544 (2.6); 2.3396 (0.51); 2.3349 (0.97); 2.3304 (1.33); 2.3257 (0.98); 2.3213 (0.52); 2.1309 (0.76); 2.0983 (1.52); 2.0724 (2.06); 2.0645 (0.89); 1.9887 (1.18); 1.8357 (0.37); 1.814 (0.68); 1.8056 (0.73); 1.7838 (0.68); 1.7757 (0.65); 1.7534 (0.32); 1.6126 (0.35); 1.6031 (0.37); 1.5818 (0.68); 1.5728 (0.74); 1.5511 (0.72); 1.5426 (0.67); 1.5216 (0.33); 1.4083 (0.58); 1.4018 (1.38); 1.3975 (3.65); 1.2468 (0.49); 1.2348 (1.13); 1.2098 (7.77); 1.1915 (16); 1.1815 (0.75); 1.173 (7.39); 1.1632 (0.52); 1.1571 (0.51); −0.0002 (2.47)
Ex. I-13, Solvent: DMSO-$d_6$ 9.6057 (0.54); 8.2467 (0.32); 8.0242 (16); 7.9807 (4.9); 7.9789 (5.09); 7.9613 (5.33); 7.9594 (5.41); 7.6688 (1.95); 7.651 (4.61); 7.6335 (3.5); 7.6311 (3.38); 7.5754 (6.21); 7.5559 (3.99); 7.4997 (3.02); 7.4806 (4.85); 7.462 (2.37); 7.4596 (2.24); 7.4309 (0.6); 7.3103 (3.18); 7.2985 (1.58); 7.2187 (0.36); 7.1926 (0.81); 7.1769 (6.82); 7.1667 (4.6); 7.1588 (1.71); 7.0569 (1.42); 7.0438 (3.68); 7.0306 (7.77); 6.9685 (1.07); 6.9211 (1.09); 6.9073 (8.56); 6.895 (4.7); 6.8611 (0.87); 6.3432 (2.94); 6.3268 (3.57); 6.3227 (2.96); 6.3155 (3.57); 6.3069 (2.32); 6.2992 (3.1); 5.7558 (9.53); 5.4535 (1.72); 5.4109 (6.13); 5.3724 (6.29); 5.3547 (1.01); 5.3299 (1.91); 5.3073 (2.85); 5.0692 (0.44); 4.3568 (1.99); 4.3422 (2.46); 4.2663 (0.93); 4.2552 (1.08); 4.2435 (0.97); 4.2242 (0.45); 4.2144 (0.37); 4.1905 (0.9); 4.1795 (1.43); 4.1621 (8.14); 4.1571 (8.22); 4.1436 (8.48); 4.1391 (7.89); 4.1101 (1.18); 4.0779 (2.79); 4.0499 (3.03); 4.0339 (3.39); 4.006 (3); 3.9757 (1.91); 3.9412 (2.17); 3.9051 (0.41); 3.7197 (0.55); 3.71 (0.93); 3.7025 (1.42); 3.6921 (1.76); 3.6756 (2.52); 3.6662 (2); 3.6626 (1.99); 3.6539 (1.21); 3.3958 (1.33); 3.3856 (1.23); 3.3755 (1.92); 3.3669 (3.52); 3.3372 (183.1); 3.2889 (2.29); 3.2593 (5.73); 3.2434 (4.25); 3.2277 (2.14); 3.2156 (3.76); 3.1994 (3.23); 3.0397 (0.96); 2.8529 (1.59); 2.8294 (2.58); 2.7993 (1.59); 2.5085 (31.73); 2.5042 (40.36); 2.5006 (31.19); 2.1191 (1.74); 2.0847 (3.76); 2.0484 (2.3); 1.9901 (0.75); 1.9116 (0.53); 1.8388 (0.7); 1.8288 (0.81); 1.8077 (1.59); 1.8 (1.7); 1.7771 (1.66); 1.7691 (1.56); 1.7472 (0.89); 1.6014 (0.74); 1.5924 (0.93); 1.5708 (1.64); 1.5626 (1.79); 1.5404 (1.69); 1.532 (1.7); 1.5103 (0.79); 1.5016 (0.72); 1.4187 (0.45); 1.396 (0.45); 1.3124 (0.58); 1.3056 (0.97); 1.2937 (1.9); 1.2858 (1.89); 1.2822 (1.76); 1.2741 (2.96); 1.2624 (2.15); 1.2554 (2.32); 1.2434 (1.7); 1.235 (2.16); 1.1935 (0.39); 1.1757 (0.59); 1.1579 (0.48); 1.145 (0.41); 0.6187 (1.63); 0.6077 (6.47); 0.6032 (7.52); 0.5875 (6.99); 0.5833 (7.15); 0.5745 (2.7); 0.555 (0.38); 0.4071 (2.63); 0.3943 (8.38); 0.385 (8.14); 0.3822 (8.4); 0.371 (2.61); −0.0002 (6.9)
Ex. I-14, Solvent: DMSO-$d_6$ 8.0236 (0.7); 8.0022 (16); 7.3308 (0.39); 7.31 (4.8); 7.3047 (5.83); 7.294 (5.45); 7.2907 (5.94); 7.2867 (3.62); 7.2762 (2.96); 7.272 (1.65); 7.2604 (0.35); 7.1711 (6.22); 7.1574 (3.08); 7.098 (0.36); 7.0613 (4.54); 7.0385 (5.81); 7.0214 (7.05); 6.9759 (2.57); 6.9556 (4.33); 6.9388 (2.08); 6.8984 (6); 6.8855 (3.41); 6.0801 (0.82); 6.0676 (1.68); 6.0539 (1.23); 6.041 (1.97); 6.0369 (1.1); 6.0285 (1.1); 6.0243 (2.09); 6.0112 (1.46); 5.9978 (1.99); 5.9853 (0.98); 5.9175 (2.25); 5.8995 (2.61); 5.8897 (2.54); 5.8715 (2.27); 5.7458 (1.02); 5.4481 (1.46); 5.4408 (1.86); 5.4364 (3.92); 5.4321 (3.92); 5.4278 (1.69); 5.406 (4.76); 5.3977 (2.07); 5.3931 (3.63); 5.3888 (3.51); 5.3846 (1.53); 5.3636 (4.56); 5.3206 (1.24); 5.249 (1.58); 5.2453 (3.35); 5.2413 (3.35); 5.2224 (1.44); 5.2188 (3.21); 5.2148 (3.09); 4.6659 (0.44); 4.6531 (0.55); 4.6319 (5.25); 4.6273 (5.61); 4.6235 (4.66); 4.6195 (5.22); 4.6149 (4.69); 4.5934 (0.44); 4.5807 (0.37); 4.3587 (1.45); 4.3249 (1.48); 4.0571 (1.18); 4.0393 (3.19); 4.0215 (3.25); 4.0036 (1.32); 3.9797 (1.39); 3.943 (1.53); 3.8883 (2.58); 3.8602 (2.89); 3.8454 (3.27); 3.8174 (2.78); 3.6096 (0.34); 3.5899 (0.32); 3.581 (0.32); 3.5439 (0.41); 3.4592 (0.77); 3.4119 (2.02); 3.4044 (2.54); 3.384 (3.45); 3.3751 (4.96); 3.3656 (4.99); 3.3168 (1799.9); 3.2952 (11.71); 3.2702 (5.7); 3.2455 (3.61); 3.2275 (3.65); 2.8652 (1); 2.8349 (1.7); 2.8071 (0.97); 2.6745 (0.73); 2.6699 (0.91); 2.6653 (0.7); 2.54 (1.38); 2.5097 (53.59); 2.5054 (99.23); 2.5009 (128.95); 2.4965 (89.43); 2.4921 (43.1); 2.4526 (0.36); 2.3323 (0.63); 2.3277 (0.83); 2.3232 (0.59); 2.1295 (1.28); 2.0945 (2.65); 2.069 (2.03); 2.0582 (1.46); 1.9868 (13.72); 1.9081 (0.4); 1.8418 (0.51); 1.8321 (0.56); 1.8033 (1.16); 1.7809 (1.08); 1.7503 (0.44); 1.6001 (0.58); 1.5701 (1.17); 1.5485 (1.11); 1.5401 (1.07); 1.5208 (0.44); 1.2365 (0.93); 1.1929 (3.85); 1.1751 (7.58); 1.1573 (3.78); −0.0002 (1.21)
Ex. I-15, Solvent: DMSO-$d_6$ 19.3402 (0.52); 18.635 (0.51); 16.0748 (0.5); 15.6162 (0.51); 10.962 (0.5); 8.7762 (1.87); 8.0216 (12.7); 7.338 (1.94); 7.3172 (3.86); 7.3056 (2.78); 7.2972 (2.3); 7.1726 (5.32); 7.158 (2.83); 7.1274 (0.51); 7.0389 (2.79); 7.0219 (6.63); 6.9886 (2.92); 6.9713 (5.97); 6.9679 (5.9); 6.9426 (2.25); 6.9374 (1.8); 6.9239 (2.13); 6.9204 (2.16); 6.916 (1.65); 6.8985 (5.7); 6.886 (3.09); 5.7459 (2.35); 5.7257 (1.7); 5.7056 (2.21); 5.6986 (2.02); 5.6795 (1.74); 5.4503 (1.08); 5.4065 (3.97); 5.3662 (4.29); 5.3405 (0.56); 5.3239 (1.22); 4.9643 (0.56); 4.8644 (0.94); 4.7451 (2.83); 4.7392 (6.89); 4.7334 (6.77); 4.3597 (1.41); 4.3248 (1.57); 4.2932 (0.57); 4.254 (0.53); 4.0647 (0.54); 4.0492 (0.56); 4.0238 (0.77); 4.0151 (0.8); 3.9841 (1.58); 3.9491 (1.86); 3.9194 (0.74); 3.9007 (1.97); 3.873 (2.14); 3.8577 (2.62); 3.8301 (2.25); 3.8081 (0.75); 3.7756 (0.67); 3.7622 (0.75); 3.7313 (0.88); 3.681 (0.88); 3.6589 (0.97); 3.6381 (1.03); 3.6044 (1.02); 3.6014 (1.13); 3.5919 (1.14); 3.5702 (1.18); 3.5265 (1.44); 3.5016 (1.8); 3.488 (1.94); 3.3406 (2.67); 3.4442 (2.95); 3.3911 (8.54); 3.3836 (9); 3.3714 (11.9); 3.312 (9031.04); 3.2888 (42.26); 3.2562 (4.61); 3.2375 (2.49); 3.2002 (0.97); 2.8742 (1.14); 2.8423 (1.67); 2.8136 (1.06); 2.7557 (0.71); 2.7114 (0.6); 2.689 (0.92); 2.6739 (5.79); 2.6696 (7.64); 2.6649 (5.69); 2.66 (2.96); 2.6526 (1.24); 2.6439 (1.02); 2.6164 (2.23); 2.5395 (10.71); 2.5226 (33.05); 2.5094 (449.88); 2.505 (830.26); 2.5005 (1078.36); 2.4961 (734.7); 2.4916 (343.72); 2.4181 (0.66); 2.3318 (5.5); 2.3272 (7.16); 2.3226 (5.11); 2.318 (2.55); 2.1526 (0.69); 2.1332 (1.28); 2.1035 (2.53); 2.0689 (2.9); 1.8059 (8.69); 1.8001 (16); 1.7943 (7.63); 1.7485 (0.63); 1.6193 (0.53); 1.583 (1.21); 1.5655 (0.81); 1.5568 (1.11); 1.3515 (0.62); 1.2977 (0.67); 1.2593 (1.19); 1.2361 (3.44); 1.1523 (0.5); 1.1082 (0.83); 1.0908 (1.05); 0.8911 (0.5); 0.8613 (1.13); 0.0079 (2.63); −0.0002 (60.11); −0.0085 (2.24); −2.4058 (0.5)
Ex. I-16, Solvent: DMSO-$d_6$ 8.0088 (10.55); 7.3947 (1.35); 7.3898 (1.87); 7.3842 (1.49); 7.3778 (2.38); 7.3724 (3.88); 7.3657 (3.51); 7.3594 (1.85); 7.3461 (2.79); 7.3421 (1.98); 7.3275 (3.4); 7.3219 (2.58); 7.3096 (2.42); 7.3051 (2.79); 7.2924 (0.86); 7.2872 (0.72); 7.1726 (3.67); 7.1632 (1.95); 7.0442 (0.73); 7.0394 (1.84); 7.0272 (4.12); 6.9623 (0.49); 6.9066 (3.51); 6.8914 (2.05); 5.9844 (1.31); 5.9645 (1.63); 5.9566 (1.58); 5.9367 (1.39); 5.6319 (0.74); 5.4476 (0.7); 5.405 (2.7); 5.3699 (2.69); 5.3272 (0.73); 5.2701 (0.39); 4.5849 (1.61); 4.5554 (3.94); 4.5218 (4.01); 4.4922 (1.69); 4.3564 (0.76); 4.3237 (0.85); 4.1907 (0.6); 4.0563 (0.83); 4.0385 (2.51); 4.0207 (2.6); 4.0029 (0.91); 3.9773 (0.35); 3.9441 (0.8); 3.9205 (1.41); 3.8926 (1.52); 3.8773 (1.73); 3.8495 (1.41); 3.5021 (0.56); 3.4856 (1.17); 3.4788 (1.82); 3.4626 (4.53); 3.4471 (4.64); 3.4403 (1.69); 3.4311 (2.29); 3.424 (2.09); 3.4047 (3.38); 3.3648 (663.23); 3.2947 (3.3); 3.2745 (2.64); 3.2675 (1.8); 3.2514 (2.31); 3.2316 (2.44); 3.1937 (0.37); 3.1863 (0.35); 2.8676 (0.6); 2.8366 (1.04); 2.8103 (0.62); 2.6779 (0.33); 2.6733 (0.45); 2.6687 (0.35); 2.5265 (1.15); 2.5133 (25.22); 2.5088 (51.37); 2.5042 (68.85); 2.4996 (50.01); 2.495 (24.56); 2.3354 (0.37); 2.3309 (0.49); 2.3263 (0.36); 2.1286 (0.71); 2.0973 (1.47); 2.0725 (0.98); 2.0611 (0.9); 2.0228 (1.11); 2.0072 (0.51); 1.9889 (11.5); 1.9102 (1.26); 1.8302 (0.37); 1.8086 (0.67); 1.8007 (0.71); 1.7787 (0.69); 1.7706 (0.64); 1.7491 (0.34); 1.6148 (0.38); 1.6044 (0.43); 1.5847 (0.75); 1.5742 (0.87); 1.5686 (0.94); 1.5648 (0.89); 1.5508 (2.22); 1.5482 (2.2); 1.5434 (1.71); 1.5344 (2.8); 1.5304 (2.52); 1.5181 (1.67); 1.513 (3.06); 1.4965 (1.43); 1.4786 (0.59); 1.462 (0.56); 1.4549 (0.41); 1.4407 (0.4); 1.3831 (0.68); 1.3645 (2.01); 1.3454 (3.11); 1.3266 (3.26); 1.3086 (2.13); 1.2903 (0.88); 1.2813 (0.59); 1.235 (2.24); 1.2102 (0.51); 1.2011 (0.58); 1.1929 (3.68); 1.1751 (6.89); 1.1692 (0.96); 1.1573 (3.46); 1.1119 (0.33); 0.8923 (7.76); 0.8739 (8); 0.8554 (7.42); 0.8443 (1.11); 0.8357 (1); −0.0002 (4.51)
Ex. I-17, Solvent: DMSO-$d_6$ 10.2605 (6.56); 9.8996 (1.37); 8.6648 (1.24); 8.048 (14.68); 7.7701 (2.71); 7.7681 (2.95); 7.7574 (3.7); 7.7553 (3.67); 7.6819 (1.07); 7.6733 (1.16); 7.6685 (1.93); 7.6601 (1.93); 7.6554 (1.23); 7.647 (1.1); 7.6113 (1.52); 7.6095 (1.53); 7.5978 (1.16); 7.5957 (1.23); 7.5931 (1.73); 7.5911 (1.61); 7.5794 (1.09); 7.5774 (1.07); 7.3707 (0.39); 7.282 (0.85); 7.2731 (1.85); 7.1934 (0.5); 7.1845 (4.41); 7.1399 (0.46); 7.1277 (2.02); 7.096 (2.12); 7.0495 (1.09); 7.0373 (5.43); 6.9593 (0.54); 6.947 (2.39); 6.9132 (4.67); 6.5802 (1.51); 6.5631 (1.94); 6.5438 (1.51); 5.7615 (16); 5.4563 (1.4); 5.4278 (3.17); 5.3792 (3.33); 5.3508 (1.46); 5.0918 (0.47); 4.3659 (1.01); 4.3437 (1.03); 4.0459 (1.09); 4.0341 (3.28); 4.0222 (3.3); 4.0104 (1.11); 3.979 (1.53); 3.959 (1.77); 3.9561 (1.57); 3.9502 (1.29); 3.9471 (1.24); 3.9273 (1.05); 3.5858 (1.32); 3.568 (1.64); 3.5574 (1.16); 3.5395 (1.13); 3.4304 (0.6); 3.4237 (0.94); 3.417

-continued (0.75); 3.4108 (1.14); 3.4046 (1.86); 3.3984 (1.29); 3.392 (1.08); 3.3854 (1.5); 3.3488 (364.36); 3.3255 (4.74); 3.2936 (0.88); 3.2736 (1.38); 3.2551 (0.76); 3.0367 (0.34); 2.8638 (0.74); 2.8483 (1.28); 2.8264 (0.74); 2.6179 (0.66); 2.6149 (0.95); 2.6119 (0.65); 2.5426 (0.66); 2.5242 (1.66); 2.5211 (2.12); 2.518 (2.39); 2.5092 (54.14); 2.5062 (120.28); 2.5031 (167.97); 2.5001 (118.69); 2.497 (50.51); 2.3903 (0.58); 2.3873 (0.88); 2.3842 (0.6); 2.1466 (0.86); 2.1274 (1.02); 2.1072 (0.92); 2.0877 (0.93); 2.0768 (1.48); 1.99 (14.99); 1.9096 (0.4); 1.8457 (0.37); 1.8257 (0.8); 1.8052 (0.76); 1.6076 (0.34); 1.5888 (0.75); 1.5688 (0.77); 1.234 (0.57); 1.1862 (4.33); 1.1744 (9.3); 1.1626 (4.08); 1.0551 (0.32); 0.0053 (1.57); −0.0002 (50.67); −0.0057 (1.48)
Ex. I-18, Solvent: DMSO-$d_6$ 8.012 (15.01); 7.3025 (4.08); 7.2994 (2.15); 7.2909 (4.11); 7.2897 (4.25); 7.2889 (4.36); 7.2869 (2.41); 7.2792 (2.16); 7.2763 (1.24); 7.2679 (1.71); 7.1793 (4.09); 7.1258 (1.87); 7.0908 (1.96); 7.0511 (2.91); 7.0499 (3.08); 7.0452 (0.57); 7.0353 (7.48); 6.9669 (1.77); 6.9656 (1.74); 6.9545 (3.16); 6.9532 (3.28); 6.945 (2.37); 6.9422 (1.81); 6.9408 (1.62); 6.9111 (4.11); 5.9209 (1.7); 5.9091 (1.96); 5.9025 (1.84); 5.8905 (1.71); 5.7615 (16); 5.4504 (1.42); 5.422 (3.14); 5.3707 (3.11); 5.3424 (1.42); 5.0906 (3.19); 5.0894 (3.21); 4.9454 (3.14); 4.5462 (0.76); 4.5248 (3.65); 4.5148 (3.71); 4.4932 (0.75); 4.3533 (0.93); 4.3316 (0.95); 4.0341 (0.38); 4.0223 (0.37); 3.9698 (0.85); 3.9473 (0.92); 3.8827 (1.89); 3.8642 (2.31); 3.8544 (2.45); 3.8359 (1.99); 3.5679 (1.49); 3.3996 (0.42); 3.3932 (0.79); 3.3869 (0.55); 3.3804 (0.9); 3.3737 (1.81); 3.3692 (1.06); 3.3674 (1.15); 3.3488 (538.95); 3.3251 (3.75); 3.287 (2.31); 3.2751 (2.72); 3.2586 (3.24); 3.2467 (2.29); 3.238 (0.74); 3.2337 (0.58); 2.8506 (0.55); 2.8466 (0.66); 2.826 (1.16); 2.8083 (0.68); 2.618 (0.39); 2.6149 (0.53); 2.6119 (0.39); 2.5242 (0.7); 2.5211 (0.9); 2.518 (0.85); 2.5092 (28); 2.5062 (63.2); 2.5031 (87.71); 2.5001 (61.35); 2.497 (26.88); 2.3904 (0.38); 2.3873 (0.52); 2.3842 (0.36); 2.1173 (0.79); 2.0956 (0.92); 2.0767 (1.37); 2.0573 (0.87); 1.99 (1.75); 1.8163 (0.4); 1.8021 (0.77); 1.7964 (0.99); 1.7845 (15.03); 1.762 (0.35); 1.563 (0.72); 1.5563 (0.76); 1.5427 (0.73); 1.5361 (0.69); 1.2335 (0.41); 1.1862 (0.49); 1.1744 (0.98); 1.1625 (0.49); 0.0052 (0.56); −0.0002 (19.67); −0.0058 (0.48)
Ex. I-19, Solvent: DMSO-$d_6$ 7.9976 (2.12); 7.9829 (16); 7.3208 (2.15); 7.3167 (3.02); 7.3041 (7.32); 7.2999 (8.68); 7.2813 (7.15); 7.2609 (0.49); 7.2412 (0.34); 7.2375 (0.35); 7.1713 (7.18); 7.1576 (3.49); 7.0691 (4.58); 7.0489 (3.89); 7.038 (3.87); 7.0214 (7.92); 6.9888 (0.49); 6.9721 (3.03); 6.9553 (4.72); 6.9362 (2.77); 6.9152 (0.92); 6.8984 (7.15); 6.8856 (3.94); 5.9563 (0.33); 5.9291 (0.33); 5.8518 (2.45); 5.833 (2.84); 5.824 (2.78); 5.8049 (2.47); 5.7461 (10.38); 5.4488 (1.5); 5.4059 (5.41); 5.3629 (5.28); 5.3201 (1.47); 4.8695 (2.28); 4.3592 (1.71); 4.325 (1.83); 4.1728 (0.6); 4.156 (5.47); 4.1449 (8.21); 4.1328 (5.55); 4.1068 (0.33); 4.0571 (0.4); 4.0392 (0.95); 4.0212 (0.98); 4.0037 (0.56); 3.9788 (1.72); 3.9471 (1.77); 3.9125 (0.51); 3.8847 (0.51); 3.869 (0.61); 3.8499 (2.63); 3.8422 (0.77); 3.8218 (3.05); 3.8071 (3.52); 3.779 (2.93); 3.7293 (0.32); 3.6912 (0.34); 3.6615 (0.56); 3.6334 (5.73); 3.6212 (6.37); 3.6112 (4.36); 3.5913 (0.63); 3.5808 (0.53); 3.5098 (0.57); 3.4853 (0.69); 3.4427 (1.07); 3.4066 (2.9); 3.3781 (4.95); 3.3687 (5.02); 3.3123 (2048.24); 3.2908 (15.02); 3.2726 (6.61); 3.233 (53.23); 3.1991 (0.47); 3.1883 (0.43); 2.8704 (1.23); 2.8373 (2.06); 2.8084 (1.11); 2.6742 (1); 2.6696 (1.27); 2.665 (0.94); 2.5394 (1.88); 2.5093 (73.81); 2.505 (136.17); 2.5006 (176.7); 2.4962 (123.71); 2.4919 (60.26); 2.3319 (0.88); 2.3273 (1.19); 2.3226 (0.94); 2.1909 (4.67); 2.1267 (1.5); 2.0943 (3.12); 2.0691 (2.56); 2.0592 (1.75); 1.9868 (3.35); 1.908 (0.6); 1.8417 (0.6); 1.8319 (0.66); 1.8093 (1.34); 1.8028 (1.41); 1.78 (1.28); 1.7503 (0.56); 1.6118 (0.66); 1.605 (0.69); 1.5798 (1.35); 1.5731 (1.39); 1.5494 (1.28); 1.5429 (1.23); 1.5213 (0.52); 1.5111 (0.54); 1.2366 (0.82); 1.1927 (0.99); 1.1749 (1.87); 1.1571 (1); −0.0002 (3.93)
Ex. I-20, Solvent: DMSO-$d_6$ 8.0084 (0.89); 7.9873 (10.75); 7.3268 (0.42); 7.313 (1.28); 7.3089 (1.93); 7.3049 (2.44); 7.2901 (6.41); 7.2714 (5.75); 7.2543 (0.4); 7.1715 (4.74); 7.1572 (2.24); 7.1135 (0.39); 7.0914 (0.41); 7.0734 (2.9); 7.0537 (2.65); 7.0382 (2.36); 7.0212 (5.18); 6.9542 (1.78); 6.9355 (3.12); 6.9169 (1.58); 6.898 (4.6); 6.8852 (2.5); 5.8386 (1.55); 5.8204 (1.85); 5.8104 (1.72); 5.792 (1.62); 5.4479 (0.96); 5.4061 (3.68); 5.3796 (2.33); 5.3761 (2.08); 5.3639 (4.29); 5.3227 (0.87); 4.5753 (4.18); 4.5595 (3.72); 4.5259 (0.51); 4.3602 (1.11); 4.3273 (1.11); 4.0568 (0.71); 4.0392 (2); 4.0213 (2.17); 4.0036 (0.88); 3.98 (1.02); 3.9458 (1.07); 3.8391 (1.71); 3.8104 (1.9); 3.7961 (2.2); 3.7678 (1.82); 3.5678 (0.92); 3.4054 (1.21); 3.3968 (1.19); 3.3868 (1.62); 3.3774 (2.32); 3.3675 (1.99); 3.3076 (966.41); 3.2843 (14.1); 3.2747 (5.11); 3.2497 (2.72); 3.2315 (2.71); 2.8903 (1.83); 2.8675 (0.75); 2.8405 (1.29); 2.8103 (0.68); 2.7313 (1.4); 2.6739 (0.63); 2.6693 (0.8); 2.665 (0.62); 2.5392 (1.1); 2.509 (47.63); 2.5047 (88.76); 2.5003 (115.69); 2.4959 (80.61); 2.4915 (38.79); 2.3314 (0.58); 2.3271 (0.78); 2.3221 (0.57); 2.1247 (0.99); 2.1161 (1.57); 2.0939 (1.98); 2.0692 (1.2); 2.0615 (1.12); 1.9868 (9.1); 1.8411 (0.43); 1.833 (0.48); 1.8037 (0.88); 1.7812 (1.19); 1.7462 (0.85); 1.6883 (16); 1.6711 (13.36); 1.6147 (0.87); 1.5814 (1.04); 1.5507 (0.88); 1.5431 (0.83); 1.5216 (0.43); 1.512 (0.39); 1.3983 (2.96); 1.3523 (0.58); 1.2986 (0.34); 1.2587 (0.51); 1.2359 (1.43); 1.1927 (2.52); 1.175 (5.09); 1.1571 (2.64); 1.1421 (2.46); 1.1205 (0.39); 0.0079 (1.11); −0.0002 (24.37); −0.0085 (1.09)
Ex. I-21, Solvent: DMSO-$d_6$ 19.9888 (0.96); 8.7773 (2.8); 8.0193 (16); 7.3512 (2.89); 7.3311 (6.43); 7.3106 (4.08); 7.3061 (3.56); 7.1727 (6.69); 7.1581 (3.79); 7.0396 (3.35); 7.0221 (8.31); 7.0073 (4.13); 6.9899 (9.48); 6.9708 (3.6); 6.9522 (2.67); 6.8982 (7.66); 6.8863 (4.58); 5.7254 (2.15); 5.7048 (2.75); 5.6978 (2.67); 5.6775 (2.23); 5.4502 (1.34); 5.4072 (5.03); 5.3667 (5.84); 5.325 (1.55); 4.8067 (14.14); 4.8007 (14.52); 4.7457 (0.98); 4.4573 (1.76); 4.3279 (1.93); 3.9827 (1.72); 3.9459 (1.87); 3.9011 (2.58); 3.8738 (2.92); 3.8579 (3.19); 3.8308 (2.68); 3.543 (3.63); 3.5371 (7.54); 3.5309 (3.71); 3.3966 (6.6); 3.3763 (7.98); 3.3535 (11.12); 3.3033 (8172.92); 3.0367 (1.37); 2.8727 (1.94); 2.8404 (2.75); 2.8131 (2.05); 2.6735 (9.82); 2.6688 (15.1); 2.6643 (9.66); 2.6595 (5.58); 2.5389 (17.62); 2.522 (52.17); 2.5087 (690.63); 2.5043 (1289.14); 2.4998 (1683.73); 2.4954 (1157.27); 2.491 (547.17); 2.3358 (4.09); 2.331 (8.04); 2.3265 (11); 2.322 (7.85); 2.1376 (1.7); 2.1029 (3.11); 2.069 (7.23); 1.9865 (1.42); 1.8197 (1.54); 1.7898 (1.46); 1.5909 (1.65); 1.5608 (1.44); 1.3984 (1.61); 1.3517 (1.09); 1.2979 (1.04); 1.2587 (1.67); 1.236 (5.02); 1.1748 (0.98); 0.8542 (0.88); 0.1462 (0.95); 0.0079 (9.36); −0.0002 (181.58); −0.0085 (5.8); −0.1492 (0.7)
Ex. I-22, Solvent: DMSO-$d_6$ 9.9022 (0.44); 8.7772 (0.5); 8.6463 (0.42); 8.013 (16); 7.7728 (0.64); 7.7581 (0.33); 7.7407 (0.5); 7.5929 (0.52); 7.3484 (9.21); 7.3313 (4.39); 7.3267 (10.28); 7.3088 (3.3); 7.2042 (0.38); 7.1754 (7.08); 7.1595 (3.59); 7.0421 (3.74); 7.0234 (8.65); 7.0126 (11.26); 7.0076 (4.29); 6.9955 (3.95); 6.9907 (9.69); 6.9573 (0.62); 6.9001 (7.6); 6.8876 (4.1); 5.7464 (13.29); 5.6954 (2.45); 5.6739 (3.26); 5.6688 (2.96); 5.6472 (2.43); 5.4524 (1.52); 5.4104 (5.36); 5.3688 (5.44); 5.3262 (1.43); 4.8008 (14.95); 4.7949 (14.86); 4.7407 (0.94); 4.3497 (1.74); 4.3317 (1.8); 4.0571 (0.8); 4.0392 (2.27); 4.0214 (2.32); 4.0037 (1.21); 3.985 (1.69); 3.9517 (1.8); 3.853 (2.59); 3.826 (2.95); 3.81 (3.38); 3.7831 (2.88); 3.5499 (3.63); 3.544 (7.26); 3.5382 (3.57); 3.4766 (0.33); 3.4424 (0.49); 3.4165 (1.72); 3.407 (1.58); 3.3895 (5.58); 3.3785 (2.68); 3.3685 (4.75); 3.3595 (2.82); 3.3469 (4.7); 3.3252 (7.94); 3.3047 (416.16); 3.281 (7.73); 3.2426 (1.41); 3.0372 (0.33); 2.8752 (1.34); 2.8491 (2.27); 2.817 (1.23); 2.6737 (0.74); 2.6693 (1.21); 2.6648 (0.7); 2.539 (1.68); 2.5087 (48.88); 2.5045 (86.78); 2.5 (110.03); 2.4957 (76.72); 2.3313 (0.55); 2.3268 (0.72); 2.3222 (0.49); 2.1375 (1.59); 2.1049 (3.18); 2.0691 (2.49); 1.9868 (9.24); 1.908 (0.66); 1.8444 (0.72); 1.8229 (1.38); 1.8154 (1.43); 1.792 (1.34); 1.7626 (0.56); 1.6213 (0.6); 1.6144 (0.71); 1.5938 (1.36); 1.5841 (1.46); 1.563 (1.36); 1.5542 (1.28); 1.534 (0.6); 1.2366 (0.62); 1.1927 (2.59); 1.1749 (5.02); 1.1571 (2.49); −0.0002 (5.18)
Ex. I-23, Solvent: DMSO-$d_6$ 10.0348 (11.5); 9.9019 (0.99); 8.6468 (0.91); 8.0407 (12.2); 7.9296 (4.81); 7.9028 (1.89); 7.8996 (2.76); 7.896 (1.64); 7.884 (2.18); 7.8807 (3.27); 7.8772 (1.89); 7.748 (2.07); 7.7287 (3.1); 7.6642 (3); 7.6453 (4.38); 7.6263 (1.82); 7.3069 (2.13); 7.1736 (4.82); 7.1587 (2.52); 7.0403 (2.41); 7.0227 (5.6); 6.9 (5.04); 6.8868 (2.92); 5.8986 (1.71); 5.8791 (2.02); 5.8715 (1.99); 5.8517 (1.78); 5.4502 (0.99); 5.408 (3.84); 5.3905 (0.39); 5.3673 (3.62); 5.3257 (0.94); 4.3619 (1.13); 4.3302 (1.22); 4.0571 (1.18); 4.0393 (3.62); 4.0215 (3.67); 4.0038 (1.43); 3.9836 (2.98); 3.956 (3.18); 3.9405 (3.28); 3.913 (2.22); 3.4478 (2.55); 3.4282 (2.8); 3.4158 (1.2); 3.4046 (2.91); 3.3965 (1.55); 3.3874 (3.77); 3.3778 (1.74); 3.3681 (1.5); 3.3583 (2.17); 3.3118 (463.38); 3.2415 (1.71); 3.1651 (0.35); 2.8729 (0.84); 2.8451 (1.48); 2.8132 (0.86); 2.6744 (0.56); 2.6698 (0.75); 2.6651 (0.54); 2.5399 (1.48); 2.5229 (3.26); 2.5096 (43.45); 2.5053 (80.56); 2.5008 (105.01); 2.4964 (74.11); 2.4921 (36.83); 2.3322 (0.66); 2.3276 (0.82); 2.3231 (0.6); 2.1344 (1.13); 2.1019 (2.17); 2.0695 (2.7); 1.987 (16); 1.8408 (0.54); 1.8113 (1); 1.7883 (0.92); 1.7607 (0.41); 1.7493 (0.34); 1.6199 (0.42); 1.6115 (0.54); 1.5916 (0.94); 1.582 (1.03); 1.5595 (0.93); 1.5512 (0.88); 1.5303 (0.4); 1.5208 (0.37); 1.1929 (4.42); 1.1751 (8.81); 1.1573 (4.38); −0.0002 (3.62)

-continued

Ex. I-24, Solvent: DMSO-d$_6$ 7.9871 (15.6); 7.3167 (1.71); 7.3126 (2.43); 7.3058 (3.38); 7.2929 (8.88); 7.2741 (7.96); 7.1725 (6.27); 7.1576 (3.14); 7.0391 (3.35); 7.0217 (9.55); 7.0049 (4.02); 6.9437 (2.71); 6.9251 (4.79); 6.8992 (6.78); 6.8856 (3.65); 5.8162 (2.25); 5.7963 (2.72); 5.7877 (2.66); 5.7676 (2.35); 5.4527 (1.31); 5.4103 (4.62); 5.3648 (4.6); 5.3221 (1.31); 4.3603 (1.48); 4.3274 (1.53); 4.0577 (1.28); 4.04 (3.76); 4.0222 (3.87); 4.0044 (1.53); 3.9836 (1.42); 3.9495 (1.52); 3.8159 (2.63); 3.7978 (6.32); 3.7859 (7.44); 3.7735 (4.14); 3.7589 (0.74); 3.7447 (2.63); 3.4189 (0.72); 3.4098 (1.27); 3.3928 (4.03); 3.3813 (2.86); 3.3729 (4.36); 3.3622 (1.64); 3.3505 (4.06); 3.3424 (2.18); 3.33 (5.88); 3.3135 (263.23); 3.2723 (2.56); 3.2422 (1.28); 2.875 (1.04); 2.846 (1.83); 2.8169 (1.04); 2.5099 (12.34); 2.5057 (22.74); 2.5012 (29.39); 2.4969 (20.73); 2.4927 (10.24); 2.1255 (1.36); 2.0925 (2.77); 2.0697 (1.29); 2.0584 (1.57); 1.9873 (16); 1.8358 (0.72); 1.8063 (1.55); 1.7849 (2.84); 1.7543 (2.27); 1.7232 (1.96); 1.6931 (1.74); 1.6095 (4.67); 1.5851 (3.35); 1.5554 (2.26); 1.5252 (0.62); 1.3974 (9.05); 1.1933 (4.55); 1.1755 (8.83); 1.1577 (4.64); 1.1322 (1.11); 1.1016 (2.23); 1.0756 (5.25); 1.0597 (4.86); 1.0278 (2.56); 1.0205 (2.72); 0.9908 (1.63); 0.9689 (0.46); 0.9607 (0.46); −0.0002 (0.72)

Ex. I-25, Solvent: DMSO-d$_6$ 18.8254 (0.66); 18.584 (0.69); 16.784 (0.68); 14.5953 (0.66); 13.1838 (0.64); 12.04 (0.63); 8.0258 (0.91); 8.007 (10.22); 7.3381 (1.45); 7.3338 (1.18); 7.3145 (5.76); 7.3028 (2.82); 7.2953 (5.13); 7.1697 (4.63); 7.1561 (2.21); 7.1342 (2.74); 7.1143 (2.48); 7.0359 (2.08); 7.0204 (4.96); 7.0039 (2.08); 6.9865 (2.96); 6.9669 (1.89); 6.8968 (4.55); 6.8846 (2.48); 5.8754 (1.85); 5.8574 (1.62); 5.8472 (1.87); 5.8309 (1.76); 5.4464 (1.25); 5.4029 (3.77); 5.3627 (3.42); 5.3494 (0.86); 5.3178 (1.35); 5.0603 (0.66); 4.8497 (0.85); 4.8244 (7.6); 4.8186 (4.48); 4.5358 (0.68); 4.4958 (0.67); 4.4923 (0.77); 4.4719 (0.65); 4.3876 (0.7); 4.3572 (1.55); 4.3262 (1.69); 4.2932 (0.75); 4.2478 (0.68); 4.1998 (0.66); 4.1293 (0.86); 4.1155 (0.69); 4.0578 (0.98); 4.0393 (1.27); 4.0211 (1.5); 3.9724 (1.72); 3.9609 (1.59); 3.9432 (2.01); 3.8852 (2.18); 3.8568 (2.79); 3.8418 (2.82); 3.8355 (1.21); 3.8138 (2.72); 3.8021 (1.23); 3.7875 (1.24); 3.7714 (1.34); 3.7587 (1.21); 3.7525 (1.26); 3.742 (1.25); 3.7382 (1.11); 3.724 (1.34); 3.7016 (1.31); 3.6484 (1.54); 3.6357 (1.73); 3.5352 (2.74); 3.4997 (3.05); 3.491 (3.38); 3.3112 (8889.96); 3.2453 (2.66); 3.2272 (4.55); 3.1928 (1.43); 3.1604 (0.94); 3.1517 (0.71); 3.1382 (0.84); 2.9122 (0.75); 2.8934 (0.67); 2.8612 (1.1); 2.8509 (1.04); 2.8326 (1.86); 2.8017 (1.35); 2.7871 (0.76); 2.7498 (1.06); 2.7227 (1.1); 2.6948 (2.09); 2.6738 (7.06); 2.6694 (8.98); 2.6648 (6.83); 2.643 (1.9); 2.5394 (19.3); 2.5091 (540.65); 2.5048 (961.58); 2.5003 (1221.22); 2.496 (846.06); 2.4916 (407.46); 2.356 (0.67); 2.3316 (5.95); 2.3271 (8.06); 2.3226 (5.63); 2.2293 (1.48); 2.2095 (4.15); 2.2045 (2.56); 2.1911 (3.93); 2.178 (1.22); 2.172 (1.42); 2.1328 (1.02); 2.1278 (1.22); 2.0901 (2.25); 2.069 (6.74); 2.0555 (1.26); 1.9866 (3.01); 1.8043 (1.08); 1.7803 (0.92); 1.5694 (1.02); 1.5662 (0.79); 1.5526 (1.06); 1.3985 (14.05); 1.2973 (0.72); 1.259 (1.04); 1.2367 (2.77); 1.1927 (1.09); 1.1749 (2.08); 1.1572 (1.15); 1.0542 (8.06); 1.0356 (16); 1.0168 (7.48); 0.9469 (0.73); 0.89 (0.75); 0.1461 (0.63); 0.0379 (0.8); 0.008 (6.36); −0.0002 (113.74); −0.0085 (4.98); −0.0292 (0.66); −2.0597 (0.67)

Ex. I-27, Solvent: DMSO-d$_6$ 8.4981 (3.72); 8.4875 (3.58); 8.0129 (16); 7.4941 (1.02); 7.4744 (3.45); 7.4711 (3.81); 7.4585 (10.06); 7.4554 (9.77); 7.4388 (5.13); 7.4208 (6); 7.3851 (3.4); 7.3799 (2.95); 7.3689 (2.71); 7.3656 (2.94); 7.3604 (1.95); 7.3508 (1.33); 7.3451 (1.27); 7.3055 (2.93); 7.1721 (6.57); 7.1578 (3.56); 7.039 (3.29); 7.0219 (7.47); 6.8975 (6.96); 6.886 (3.78); 6.002 (2.73); 5.9834 (3.3); 5.9746 (3.2); 5.9557 (2.71); 5.7468 (7.45); 5.4471 (1.31); 5.4042 (5.11); 5.366 (5.11); 5.3238 (1.29); 4.3531 (1.67); 4.3222 (1.77); 4.0389 (0.69); 4.021 (0.68); 3.9765 (1.68); 3.9408 (4.14); 3.9128 (3.2); 3.8967 (3.34); 3.8695 (2.77); 3.7691 (0.34); 3.7614 (0.32); 3.6672 (0.39); 3.6627 (0.33); 3.6586 (0.36); 3.6261 (0.34); 3.6154 (0.36); 3.5911 (0.42); 3.5384 (0.54); 3.5283 (0.57); 3.5165 (0.61); 3.5024 (0.64); 3.4819 (0.77); 3.405 (2.62); 3.3969 (2.62); 3.377 (4.86); 3.3672 (4.57); 3.3061 (1839.02); 3.2826 (19.62); 3.257 (5.23); 3.2318 (4.35); 3.213 (3.12); 3.1892 (0.36); 2.8688 (1.52); 2.859 (1.85); 2.8485 (3.18); 2.8406 (4.71); 2.8307 (3.61); 2.822 (2.42); 2.8122 (2.55); 2.6736 (1.25); 2.6693 (1.66); 2.6646 (1.26); 2.6474 (0.36); 2.6296 (0.41); 2.6127 (0.49); 2.5391 (2.86); 2.5087 (94.6); 2.5045 (172.38); 2.5001 (221.82); 2.4957 (155.71); 2.4914 (76.1); 2.4284 (0.34); 2.4204 (0.33); 2.3269 (1.41); 2.3222 (1.02); 2.1264 (1.41); 2.0946 (2.99); 2.0695 (1.74); 2.0607 (1.74); 1.9867 (2.17); 1.8377 (0.63); 1.8099 (1.31); 1.7842 (1.25); 1.7573 (0.61); 1.6026 (0.73); 1.58 (1.31); 1.5735 (1.33); 1.5506 (1.34); 1.5411 (1.24); 1.5203 (0.57); 1.2354 (0.95); 1.1926 (0.65); 1.1749 (1.1); 1.1573 (0.61); 0.8903 (0.39); 0.8804 (0.54); 0.7214 (1.61); 0.7075 (4.67); 0.7033 (6.63); 0.6913 (5.83); 0.6851 (5.31); 0.674 (2.23); 0.6533 (0.45); 0.6338 (0.7); 0.6234 (0.45); 0.5933 (2.69); 0.5829 (7.2); 0.5754 (6.42); 0.5664 (4.87); 0.5552 (1.83); 0.0664 (0.33); 0.0079 (0.82); −0.0002 (13.42)

Ex. I-28, Solvent: DMSO-d$_6$ 9.9013 (0.53); 8.6464 (0.53); 8.0179 (15.28); 7.3196 (2.72); 7.3066 (3.18); 7.299 (5.35); 7.2797 (2.76); 7.1734 (6.02); 7.1587 (2.95); 7.0402 (3.1); 7.0227 (6.79); 6.9616 (3.89); 6.9443 (8.41); 6.9407 (8.6); 6.919 (3.44); 6.913 (2.72); 6.8993 (8.65); 6.8904 (3.05); 6.8869 (3.66); 5.7459 (1.42); 5.7185 (2.22); 5.6983 (2.65); 5.6917 (2.59); 5.6714 (2.26); 5.4494 (1.23); 5.4075 (4.65); 5.367 (4.47); 5.3239 (1.16); 4.3609 (1.49); 4.3283 (1.5); 4.1321 (0.32); 4.105 (5.25); 4.0938 (5.94); 4.0896 (5); 4.0819 (5.91); 4.057 (1.44); 4.0392 (3.89); 4.0214 (3.85); 4.0036 (1.51); 3.9823 (1.43); 3.9484 (1.53); 3.8922 (2.43); 3.8649 (2.72); 3.8492 (3.13); 3.8221 (2.69); 3.6592 (6.77); 3.6515 (5.61); 3.6476 (6.96); 3.6443 (5.51); 3.6362 (6); 3.5682 (0.37); 3.4945 (0.54); 3.4891 (0.54); 3.4738 (0.81); 3.454 (0.72); 3.421 (1.55); 3.4132 (2.22); 3.3957 (5.44); 3.3848 (4.28); 3.3756 (6.39); 3.3529 (8.44); 3.3143 (1657.1); 3.2997 (69.45); 3.2708 (3.69); 3.2406 (1.59); 3.1928 (0.32); 3.1214 (0.30); 2.872 (0.94); 2.844 (1.7); 2.8143 (1); 2.6743 (0.71); 2.6698 (0.93); 2.6653 (0.73); 2.5657 (1.67); 2.5395 (1.44); 2.5095 (56.57); 2.5052 (103.94); 2.5007 (134.27); 2.4964 (93.13); 2.492 (44.99); 2.4479 (0.38); 2.3322 (0.71); 2.3276 (0.85); 2.3227 (0.68); 2.1347 (1.33); 2.1026 (2.58); 2.069 (2.13); 1.9868 (16); 1.9081 (0.57); 1.8414 (0.58); 1.8114 (1.2); 1.7888 (1.09); 1.7601 (0.49); 1.6225 (0.56); 1.6109 (0.66); 1.5902 (1.12); 1.5809 (1.22); 1.5612 (1.08); 1.552 (1.02); 1.53 (0.49); 1.5202 (0.42); 1.3983 (0.86); 1.2375 (0.41); 1.1928 (4.44); 1.175 (8.82); 1.1572 (4.31); −0.0002 (1.96)

Ex. I-29, Solvent: DMSO-d$_6$ 7.9726 (11.82); 7.4193 (1.12); 7.3983 (2.39); 7.3812 (2.34); 7.3608 (1.18); 7.3089 (2.02); 7.1757 (4.66); 7.1592 (2.23); 7.0424 (2.27); 7.0231 (5.17); 6.9821 (3.52); 6.961 (3.13); 6.8999 (4.73); 6.8875 (3.85); 6.8642 (2.22); 6.8429 (1.67); 6.0641 (1.51); 6.0423 (1.98); 6.0345 (1.89); 6.0117 (1.64); 5.4562 (0.97); 5.413 (3.42); 5.3697 (3.39); 5.3271 (1); 4.8073 (0.37); 4.7737 (5.62); 4.768 (5.6); 4.3713 (1.13); 4.3692 (1.17); 4.3406 (1.14); 3.9911 (1.17); 3.9584 (1.19); 3.7947 (1.21); 3.7659 (1.47); 3.7544 (1.85); 3.7222 (1.59); 3.6983 (0.36); 3.6678 (0.43); 3.6525 (0.39); 3.5964 (0.45); 3.5693 (0.5); 3.5395 (2.27); 3.5178 (2.32); 3.4968 (1.94); 3.4754 (2.07); 3.4274 (2.13); 3.398 (3.64); 3.3882 (3.45); 3.3797 (3.8); 3.3127 (2744.28); 3.2894 (25.2); 3.257 (2.1); 2.8782 (0.78); 2.8521 (1.41); 2.8219 (0.8); 2.6739 (1.19); 2.6696 (1.62); 2.665 (1.2); 2.6259 (0.33); 2.6072 (0.34); 2.5855 (0.5); 2.5395 (2.35); 2.5093 (97.19); 2.505 (179.71); 2.5006 (232.83); 2.4962 (162.42); 2.4919 (78.86); 2.332 (1.16); 2.3271 (1.52); 2.3222 (1.05); 2.1515 (0.98); 2.1201 (1.96); 2.0786 (1.21); 2.0689 (6.74); 1.8494 (0.51); 1.8217 (0.93); 1.7992 (0.89); 1.759 (8.2); 1.7533 (16); 1.7477 (7.73); 1.6309 (0.41); 1.6235 (0.49); 1.5999 (0.95); 1.592 (0.98); 1.5718 (0.86); 1.5395 (0.39); 1.3983 (0.42); 1.2369 (0.61); −0.0002 (14.45)

Ex. I-30, Solvent: DMSO-d$_6$ 7.9681 (16); 7.433 (1.5); 7.416 (1.98); 7.4119 (3.1); 7.3952 (3.13); 7.391 (1.89); 7.3739 (1.51); 7.3085 (2.56); 7.175 (5.8); 7.1585 (2.74); 7.0418 (2.83); 7.0226 (6.92); 7.0121 (4.36); 6.9908 (3.84); 6.9093 (3.01); 6.9008 (5.87); 6.8865 (5.33); 6.8644 (1.87); 6.074 (1.94); 6.0516 (2.36); 6.0436 (2.19); 6.0213 (1.96); 5.4545 (1.14); 5.411 (4.19); 5.369 (4.16); 5.3271 (1.09); 4.887 (0.53); 4.8816 (0.59); 4.8472 (6.66); 4.8417 (10.99); 4.8361 (6.08); 4.802 (0.48); 4.7962 (0.58); 4.3673 (1.31); 4.3338 (1.42); 3.9904 (1.39); 3.9536 (1.47); 3.8311 (0.43); 3.8095 (1.58); 3.7769 (1.77); 3.7681 (2.13); 3.7375 (1.93); 3.5278 (3.35); 3.5207 (4.59); 3.5148 (8.43); 3.5088 (5); 3.4848 (3.01); 3.4631 (3.39); 3.3942 (7.5); 3.3307 (5101.71); 3.3077 (39.28); 3.2505 (2.33); 3.214 (0.93); 3.1513 (0.33); 2.8803 (0.83); 2.8505 (1.57); 2.8219 (0.84); 2.6753 (1.19); 2.6708 (1.61); 2.6661 (1.17); 2.6613 (0.59); 2.5407 (2.04); 2.5107 (94.07); 2.5063 (176.46); 2.5017 (231.85); 2.4973 (160.85); 2.4929 (77.91); 2.3331 (1.24); 2.3283 (1.57); 2.1548 (1.15); 2.11.71 (2.28); 2.0796 (1.44); 2.0684 (11.58); 1.8497 (0.53); 1.8211 (1.07); 1.7995 (1.06); 1.6243 (0.49); 1.5944 (1.06); 1.5722 (1.05); 1.5414 (0.42); 1.2375 (0.37); −0.0002 (12.57)

Ex. I-31, Solvent: DMSO-d$_6$ 10.2929 (9.8); 8.7763 (4.66); 8.2983 (15.34); 8.0298 (3.08); 8.0268 (3.07); 8.0104 (3.61); 8.0074 (3.55); 7.9472 (2.56); 7.9445 (2.64); 7.9278 (4.4); 7.925 (4.28); 7.8912 (2.38); 7.8878 (2.33); 7.8727 (3.9); 7.8692 (3.55); 7.8536 (1.98); 7.8502 (1.68); 7.7879 (2.19); 7.7685 (3.22); 7.7506 (1.42); 7.4325 (16); 7.3636 (0.36); 7.3559 (0.57); 7.3182 (2.51); 7.3032 (1.2); 7.284 (0.51); 7.1849 (5.51); 7.1696 (3.14); 7.1643 (3.27); 7.157 (1.77); 7.1516 (1.2); 7.1117 (0.6); 7.0519 (2.69); 7.0363 (1.62); 7.0284 (6.38); 7.021 (3.52); 6.9056 (6.47); 6.8924 (4); 6.8853 (1.94); 5.7459 (7.44); 5.4676 (1.16); 5.4256 (4.12); 5.3959 (2.55); 5.3844 (4.4); 5.3658 (1.99); 5.3538 (2.02); 5.3425 (1.57); 5.3066 (1.18); 5.1928 (0.67); 4.5401 (0.32); 4.486 (0.36); 4.3976 (1.37); 4.3587 (1.65); 4.3162 (0.88); 4.2906 (0.34); 4.2601 (0.36); 4.2022 (0.33); 4.1853 (0.33); 4.1801 (0.4); 4.149 (0.45); 4.1315 (1.07); 4.114 (0.98); 4.0994 (0.42); 4.0962 (0.51); 4.0567 (0.9); 4.0391 (2.37); 4.0214 (3.01); 4.0035 (1.62); 3.9809 (1.98); 3.9407 (0.89); 3.8995 (0.43); 3.8305 (0.46); 3.8229 (0.47); 3.8148 (0.51); 3.8009 (0.56); 3.7917 (0.49); 3.7729 (0.5); 3.739 (0.58); 3.7245 (0.59); 3.7066 (0.58); 3.6805 (0.67); 3.6669 (0.75); 3.6348 (0.77); 3.5909 (0.8); 3.5762 (0.89); 3.544 (1.01); 3.5038 (1.37); 3.4839 (2.13); 3.456 (3.53); 3.4474 (3.04); 3.4271 (3.51); 3.4141 (3.55); 3.3145 (4026.52); 3.2023 (0.7); 3.1638 (0.36); 3.037 (2.37); 2.9084 (0.93); 2.8737 (1.7); 2.8499 (3.05); 2.8096 (0.56); 2.6992 (0.37); 2.6746 (1.93); 2.6698 (2.51); 2.6651 (1.88); 2.6417 (0.45); 2.6177 (0.56); 2.6052 (0.65); 2.5399 (3.63); 2.5096 (137.51); 2.5053 (254.27); 2.5008 (329.93); 2.4964 (227.27); 2.492 (107.64); 2.332 (1.47); 2.3275 (2.04); 2.3231 (1.54); 2.1956 (1.21); 2.1611 (2.32); 2.1257 (1.67); 2.102 (1.16); 2.0848 (14.59); 2.0692 (1.6); 2.0476 (0.5); 2.0429 (0.41); 2.0149 (0.32); 1.9868 (8.85); 1.8984 (0.58); 1.8707 (1.17); 1.8491 (1.21); 1.8178 (0.85); 1.7906 (0.67); 1.7861 (0.59); 1.7788 (0.61); 1.7388 (0.38); 1.6831 (0.78); 1.651 (1.48); 1.6215 (1.46); 1.589 (0.85); 1.5803 (0.66); 1.5602 (0.51); 1.5561 (0.55); 1.5531 (0.5); 1.5286 (0.47); 1.525 (0.44); 1.3986 (1.68); 1.2402 (1.4); 1.2221 (2.07); 1.2043 (0.95); 1.1928 (2.53); 1.175 (4.9); 1.1572 (2.49); 1.1471 (0.43); 0.9453 (0.33); −0.0002 (13.04); −0.0086 (0.54)

Ex. I-32, Solvent: DMSO-d$_6$ 8.0564 (0.67); 8.0421 (16); 7.4458 (3.11); 7.442 (3.43); 7.4268 (3.82); 7.4227 (4.75); 7.4155 (1.9); 7.4005 (3.86); 7.3961 (3.09); 7.3811 (2.97); 7.3767 (2.33); 7.3042 (5.74); 7.2881 (4.13); 7.2853 (4.14); 7.2692 (1.72); 7.2665 (1.62); 7.202 (0.34); 7.171 (6.68); 7.1569 (3.32); 7.1431 (4.64); 7.1406 (4.46); 7.1231 (4.07); 7.1206 (3.69); 7.0377 (3.28); 7.0209 (7.38); 6.8985 (6.33); 6.885 (3.66); 5.7504 (2.42); 5.7304 (2.9); 5.7216 (2.69); 5.7019 (2.48); 5.4518 (1.33); 5.4089 (4.58); 5.3638 (4.56); 5.3213 (1.3); 4.3853 (0.42); 4.3618 (1.57); 4.3593 (1.58); 4.3289 (1.54); 4.0569 (0.94); 4.0391 (2.62); 4.0214 (2.58); 4.0034 (1.17); 3.9821 (1.51); 3.9509 (1.7); 3.8783 (2.45); 3.8498 (2.86); 3.8355 (3.33); 3.8219 (0.49); 3.8068 (2.77); 3.7302 (0.35); 3.7053 (0.35); 3.6846 (0.39); 3.633 (0.44); 3.6077 (0.5); 3.58 (0.49); 3.5626 (0.57); 3.4258 (2.02); 3.4165 (2.62); 3.3882 (4.64); 3.3779 (4.5); 3.3103 (1658.59); 3.262 (5.58); 3.2419 (4.22); 3.0574 (14.26); 2.8746 (0.98); 2.8433 (1.78); 2.8131 (0.98); 2.6738 (1.19); 2.6694 (1.65); 2.6647 (1.19); 2.6604 (0.69); 2.5863 (1.14); 2.5775 (1.86); 2.5687 (1.53); 2.5587 (2.41); 2.5497 (3.93); 2.5397 (3.62); 2.5092 (90.95); 2.5048 (169.36); 2.5003 (221.44); 2.4959 (153.89); 2.4915 (73.81); 2.3316 (1.05); 2.3268 (1.46); 2.3226 (1.08); 2.1566 (0.5); 2.1534 (0.47); 2.1288 (1.46); 2.0952 (2.79); 2.069 (4.5); 2.0094 (1.48); 1.9867 (12.07); 1.937 (1.48); 1.9072 (1.58); 1.8514 (0.38); 1.8366 (0.59); 1.8075 (1.63); 1.7742 (1.62); 1.691 (2.87); 1.6777 (2.37); 1.6661 (2.03); 1.6382 (1.11); 1.6104 (2.08); 1.6039 (2.28); 1.583 (2.59); 1.553 (1.62); 1.5441 (1.47); 1.5219 (0.68); 1.5096 (1.04); 1.5009 (1.3); 1.4939 (1); 1.4719 (2.77); 1.4428 (2.64); 1.422 (1.04); 1.4121 (1.32); 1.3984 (4.82); 1.3599 (0.49); 1.3522 (0.4); 1.3237 (0.97); 1.3161 (0.74); 1.2936 (1.53); 1.2855 (1.57); 1.2775 (1.47); 1.2539 (2.13); 1.221 (3.2); 1.1927 (6.06); 1.1749 (7.28); 1.1571 (3.48); 1.1511 (0.66); 1.0561 (0.62); 0.8896 (0.33); 0.008 (1.07); −0.0002 (23.89); −0.0084 (1.03)

Ex. I-33, Solvent: DMSO-d$_6$ 8.0449 (0.85); 8.0307 (16); 7.4467 (3.19); 7.4426 (3.33); 7.4274 (3.8); .7.4236 (4.09); 7.4145 (1.89); 7.4098 (1.62); 7.3954 (3.73); 7.3906 (2.89); 7.3757 (2.96); 7.3713 (2.2); 7.3109 (3.24); 7.3078 (3.83); 7.2921 (3.92); 7.2892 (3.94); 7.2733 (1.65); 7.2338 (0.34); 7.1715 (10.39); 7.1572 (3.81); 7.1538 (4.36); 7.1511 (3.68); 7.0383 (3.11); 7.0214 (7.15); 6.8995 (6.18); 6.8855 (3.42); 5.7594 (2.31); 5.74 (2.86); 5.7311 (2.73); 5.7112 (2.3); 5.4498 (1.37); 5.4085 (4.59); 5.3638 (4.67); 5.3202 (1.27); 4.7805 (0.32); 4.7391 (0.32); 4.3623 (1.62); 4.3289 (1.63); 4.26 (0.32); 4.2317 (0.37); 4.2084 (0.37); 4.192 (0.35); 4.186 (0.41); 4.1654 (0.39); 4.1349 (0.4); 4.1203 (0.4); 4.0568 (1.39); 4.0392 (3.53); 4.0213 (3.67); 4.0034 (1.64); 3.9822 (1.64); 3.9482 (1.7); 3.8942 (2.81); 3.8653 (3.21); 3.8509 (3.36); 3.8224 (2.98); 3.7494 (0.57); 3.6821 (0.69); 3.6683 (0.77); 3.6417 (0.8); 3.6015 (1.59); 3.5876 (1.16); 3.5664 (1.08); 3.5378 (1.18); 3.5131 (1.33); 3.4823 (1.59); 3.4764 (1.78); 3.3833 (8.42); 3.3191 (4565.63); 3.2922 (16.26); 3.272 (8.14); 3.2484 (4.61); 3.2289 (3.64); 3.1704 (0.37); 3.0574 (3.22); 2.8707 (1.03); 2.8433 (1.69); 2.8113 (1.01); 2.6746 (1.55); 2.6701 (2.23); 2.6655 (1.58); 2.6609 (0.87); 2.54 (3.1); 2.5098 (135.46); 2.5054 (250.35); 2.501 (325.5); 2.4965 (224.28); 2.4921 (106.69); 2.3322 (1.5); 2.3275 (2.16); 2.3234 (1.54); 2.1319 (1.58); 2.0953 (2.73); 2.0687 (6.45); 1.9868 (14.8); 1.9080 (0.38); 1.8733 (0.76); 1.8565 (1.63); 1.8414 (2.92); 1.8356 (1.89); 1.8307 (2.09); 1.823 (1.8); 1.8106 (1.92); 1.7703 (1.41); 1.7605 (1.37); 1.7529 (0.81); 1.7439 (0.83); 1.601 (0.65); 1.5799 (1.23); 1.5733 (1.29); 1.5522 (1.15); 1.5199 (0.57); 1.3984 (5.98); 1.3499 (0.37); 1.2364 (1.21); 1.1928 (4.43); 1.175 (8.37); 1.1572 (4.29); 1.1241 (0.46); 1.107 (0.42); 1.0735 (1.13); 1.0654 (1.2); 1.0527 (2.77); 1.0472 (3.27); 1.0319 (5.75); 1.021 (4.22); 1.0149 (4.83); 1.0087 (4.54); 1.0042 (2.9); 0.998 (2.4); 0.9888 (2.88); 0.9834 (2.07); 0.9757 (2.28); 0.964 (2.97); 0.95 (1.67); 0.9445 (1.47); 0.9312 (0.76); 0.8904 (0.66); 0.8346 (0.33); 0.7914 (0.38); 0.7855 (0.37); 0.768 (0.32); 0.008 (1.2); −0.0002 (26.72); −0.0085 (1.09)

Ex. I-34, Solvent: DMSO-d$_6$ 8.7767 (1.01); 8.0195 (10.27); 7.3364 (2.01); 7.3283 (0.48); 7.3162 (4.18); 7.306 (2.23); 7.2959 (2.57); 7.1727 (4.18); 7.1582 (2.25); 7.0395 (2.09); 7.0222 (4.95); 6.9869 (3.67); 6.9805 (3.48); 6.9752 (3.68); 6.9439 (1.88); 6.9421 (1.89); 6.9378 (1.57); 6.9234 (1.72); 6.9214 (1.68); 6.9173 (1.56); 6.9152 (1.42); 6.8992 (4.59); 6.8863 (2.54); 5.7461 (6.78); 5.7267 (1.38); 5.7067 (1.64); 5.6996 (1.6); 5.6795 (1.4); 5.4492 (0.78); 5.4067 (3.05); 5.3633 (3.24); 5.3236 (0.83); 4.7544 (4.46); 4.7491 (8.07); 4.7438 (4.45); 4.3597 (0.92); 4.3273 (1); 3.9814 (0.9); 3.9469 (0.99); 3.9041 (1.5); 3.8767 (1.71); 3.861 (1.94); 3.8337 (1.62); 3.4219 (0.62); 3.4121 (0.92); 3.4018 (0.85); 3.3904 (2.75); 3.3835 (1.97); 3.3702 (2.79); 3.3542 (2.09); 3.3471 (3.57); 3.3113 (921.47); 3.2763 (3.03); 3.2402 (1.32); 2.8904 (0.52); 2.8715 (0.76); 2.8421 (1.27); 2.8138 (0.71); 2.7311 (0.35); 2.6741 (0.56); 2.6696 (0.75); 2.665 (0.56); 2.6541 (0.51); 2.5697 (0.39); 2.5396 (0.86); 2.5227 (2.51); 2.5094 (40.17); 2.505 (76.36); 2.5005 (101.04); 2.4961 (70.54); 2.4917 (34.3); 2.3362 (0.35); 2.3319 (0.57); 2.3273 (0.77); 2.3226 (0.56); 2.22 (0.79); 2.2148 (1.38); 2.2094 (0.92); 2.2013 (1.96); 2.196 (3.73); 2.1907 (2.01); 2.1825 (2.06); 2.1773 (3.84); 2.172 (1.98); 2.164 (0.93); 2.1586 (1.52); 2.1354 (1.27); 2.0999 (1.92); 2.069 (1.62); 1.9868 (1); 1.8389 (0.44); 1.8096 (0.86); 1.7859 (0.8); 1.7782 (0.76); 1.7567 (0.38); 1.6199 (0.38); 1.6092 (0.46); 1.588 (0.8); 1.5795 (0.88); 1.5576 (0.82); 1.5498 (0.8); 1.5292 (0.39); 1.439 (0.7); 1.4171 (0.63); 1.3982 (9.94); 1.3845 (0.84); 1.3525 (0.44); 1.2989 (0.35); 1.2588 (0.52); 1.2359 (0.97); 1.1928 (0.36); 1.175 (0.61); 1.1572 (0.34); 1.0618 (0.37); 1.0419 (7.86); 1.0232 (16); 1.0045 (7.35); 0.9857 (0.4); −0.0002 (5.44)

Ex. I-35, Solvent: DMSO-d$_6$ 8.0082 (11.59); 7.3952 (0.36); 7.3372 (1.11); 7.3331 (1.49); 7.3138 (6.53); 7.3043 (2.48); 7.2949 (6.01); 7.2628 (0.73); 7.2251 (0.37); 7.1709 (4.28); 7.157 (2.11); 7.1289 (3.52); 7.1089 (2.94); 7.09 (0.84); 7.0377 (2.14); 7.021 (4.87); 7.0024 (1.97); 6.985 (3.29); 6.9666 (1.54); 6.9549 (0.45); 6.8983 (4.09); 6.8851 (2.38); 5.9134 (0.58); 5.9074 (0.64); 5.8763 (1.66); 5.8583 (2.03); 5.8485 (2.25); 5.8304 (1.74); 5.7452 (3.89); 5.4469 (0.79); 5.4047 (3.02); 5.3634 (2.99); 5.321 (0.78); 4.8129 (6.5); 4.807 (6.58); 4.3596 (0.94); 4.3268 (0.95); 3.9783 (0.88); 3.9439 (0.93); 3.8847 (1.63); 3.8568 (1.89); 3.8418 (2.12); 3.814 (1.78); 3.4127 (0.72); 3.4036 (1.12); 3.3947 (1.14); 3.3846 (1.56); 3.3752 (2.37); 3.3656 (2.18); 3.3185 (1355.83); 3.2952 (14.91); 3.2803 (4.54); 3.2621 (4.23); 3.2372 (2.85); 3.2192 (2.45); 2.8632 (0.68); 2.8339 (1.16); 2.8055 (0.69); 2.6793 (0.39); 2.6747 (0.72); 2.6701 (0.98); 2.6657 (0.73); 2.6608 (0.38); 2.5401 (1.07); 2.5233 (3.57); 2.5099 (54.86); 2.5055 (103.8); 2.501 (136.66); 2.4966 (94.58); 2.4922 (45.14); 2.3369 (0.42); 2.3324 (0.74); 2.3277 (0.99); 2.3232 (0.73); 2.3185 (0.39); 2.1279 (0.99); 2.094 (1.88); 2.0688 (2.48); 2.0602 (1.07); 1.9869 (0.33); 1.8234 (7.69); 1.8177 (16); 1.812 (8.61); 1.7817 (0.84); 1.7746 (0.79); 1.7526 (0.37); 1.6799 (0.38); 1.6512 (0.33); 1.6118 (0.38); 1.6008 (0.41); 1.5806 (0.76); 1.5708 (0.8); 1.5502 (0.75); 1.541 (0.71); 1.5201 (0.34); 1.3524 (0.58); 1.2985 (0.97); 1.259 (1.38); 1.2362 (1.58); 0.0079 (0.45); −0.0002 (10.51); −0.0085 (0.43)

-continued

Ex. I-36, Solvent: DMSO-$d_6$ 8.0517 (0.55); 8.0421 (9.39); 7.487 (1.77); 7.483 (2.13); 7.468 (2.33); 7.4639 (2.89); 7.4565 (1.15); 7.4416 (2.4); 7.437 (1.9); 7.422 (1.97); 7.4176 (1.52); 7.3704 (1.79); 7.3678 (1.9); 7.3517 (2.43); 7.3489 (2.47); 7.3327 (1.03); 7.3302 (0.94); 7.3034 (1.8); 7.2377 (2.9); 7.2349 (2.76); 7.2177 (2.46); 7.215 (2.29); 7.17 (4.06); 7.157 (2.01); 7.0368 (2.04); 7.021 (4.53); 6.8989 (4.2); 6.8851 (2.3); 5.8325 (1.5); 5.8127 (1.73); 5.8042 (1.7); 5.7843 (1.5); 5.4469 (0.77); 5.4051 (3.05); 5.3656 (3); 5.3234 (0.79); 4.3588 (0.94); 4.3279 (1); 4.0806 (1.41); 4.0539 (4.47); 4.0391 (4.17); 4.0269 (4.73); 4.0214 (4.41); 4.0033 (1.92); 4.0002 (1.89); 3.9825 (0.99); 3.9466 (1.04); 3.9162 (1.61); 3.8879 (1.82); 3.873 (1.94); 3.8448 (1.68); 3.4712 (0.35); 3.413 (1.18); 3.4024 (1.14); 3.3936 (1.6); 3.3845 (2.21); 3.3755 (1.94); 3.355 (2.83); 3.3075 (760.65); 3.261 (3.18); 3.2408 (2.56); 3.2176 (1.78); 3.1978 (1.63); 2.8708 (0.64); 2.8411 (1.16); 2.8112 (0.64); 2.6738 (0.6); 2.6691 (0.78); 2.6648 (0.58); 2.5392 (1.14); 2.509 (44.2); 2.5047 (81.04); 2.5003 (104.48); 2.4959 (71.67); 2.4915 (33.77); 2.3317 (0.47); 2.3269 (0.69); 2.3225 (0.49); 2.1308 (0.83); 2.0988 (1.7); 2.0691 (1.76); 1.9867 (16); 1.84 (0.33); 1.8353 (0.35); 1.8234 (0.38); 1.8038 (0.77); 1.7819 (0.73); 1.6165 (0.51); 1.5845 (0.78); 1.5529 (0.73); 1.5438 (0.7); 1.5234 (0.35); 1.3983 (4.85); 1.2592 (0.37); 1.236 (0.78); 1.1927 (4.49); 1.1749 (8.81); 1.1571 (4.35); 0.0079 (1.6); −0.0002 (33.58); −0.0085 (1.31)

Ex. I-37, Solvent: DMSO-$d_6$ 9.286 (0.77); 8.0342 (0.41); 8.0227 (6.59); 7.4384 (1.2); 7.4218 (1.56); 7.4179 (1.38); 7.4022 (0.48); 7.3983 (0.44); 7.378 (1.63); 7.3675 (2.98); 7.3618 (4.85); 7.359 (4.72); 7.3489 (1.31); 7.3418 (1.25); 7.3362 (1); 7.326 (0.42); 7.3199 (0.42); 7.3059 (1.22); 7.1727 (2.75); 7.1577 (1.34); 7.0393 (1.33); 7.0217 (3.07); 6.8983 (2.75); 6.8858 (1.55); 6.1213 (1); 6.1009 (1.24); 6.0939 (1.18); 6.0731 (1.03); 5.7462 (4.79); 5.4499 (0.57); 5.4078 (2.02); 5.3661 (2.03); 5.3244 (0.54); 4.3621 (0.65); 4.3289 (0.68); 4.057 (0.43); 4.0391 (1.24); 4.0214 (1.28); 4.0035 (0.54); 3.98 (0.7); 3.9542 (1.5); 3.9265 (1.25); 3.9104 (1.33); 3.8829 (1.06); 3.4406 (0.38); 3.4149 (0.94); 3.4044 (0.87); 3.3859 (1.6); 3.3769 (1.44); 3.3562 (2.16); 3.3105 (820.01); 3.2875 (8.8); 3.2661 (2.52); 3.2457 (1.52); 3.2383 (0.81); 3.0528 (0.75); 3.0357 (16); 2.8685 (0.27); 2.8395 (0.8); 2.8139 (0.48); 2.6741 (0.63); 2.6694 (0.85); 2.6651 (0.6); 2.5396 (1.07); 2.5225 (3.59); 2.5092 (46.39); 2.5049 (85.81); 2.5004 (111.31); 2.4961 (77.41); 2.4918 (37.22); 2.3316 (0.51); 2.3272 (0.72); 2.3226 (0.53); 2.1304 (0.57); 2.101 (1.15); 2.069 (1.34); 1.9867 (5.13); 1.8115 (0.51); 1.7875 (0.47); 1.5885 (0.52); 1.5789 (0.52); 1.5569 (0.5); 1.549 (0.47); 1.1927 (1.42); 1.1749 (2.77); 1.1571 (1.36); −0.0002 (3.8)

Ex. I-38, Solvent: DMSO-$d_6$ 8.045 (16); 7.7484 (0.42); 7.5602 (3.52); 7.5418 (4.61); 7.478 (0.38); 7.4714 (0.79); 7.4685 (0.79); 7.4518 (3.13); 7.4487 (3.22); 7.4363 (8); 7.4329 (10.02); 7.4188 (1.4); 7.3968 (0.35); 7.3804 (2.83); 7.3742 (2.42); 73615 (2.72); 7.3587 (2.27); 7.355 (2.18); 7.346 (1.48); 7.3395 (1.46); 7.3056 (2.68); 7.1723 (6.13); 7.158 (3.08); 7.039 (3.04); 7.0219 (7.05); 6.9004 (6.15); 6.8861 (3.37); 6.0236 (2.56); 6.0054 (3); 5.9958 (2.9); 5.9775 (2.56); 5.7443 (11.99); 5.4496 (1.18); 5.4071 (4.43); 5.3648 (4.59); 5.3223 (1.19); 4.542 (13.91); 4.522 (0.34); 4.3622 (1.38); 4.3285 (1.5); 4.0575 (0.54); 4.0398 (1.48); 4.0219 (1.67); 4.0127 (2.68); 4.0042 (0.87); 3.9848 (4); 3.9696 (4.08); 3.9418 (3.99); 3.8728 (0.33); 3.5684 (1.48); 3.4573 (0.73); 3.4092 (2.36); 3.3992 (2.48); 3.3798 (5.27); 3.3333 (1502.56); 3.3141 (12.84); 3.3103 (13.57); 3.2958 (5.87); 3.2647 (2.23); 3.2351 (1.18); 2.8911 (0.39); 2.8659 (0.95); 2.8361 (1.67); 2.8077 (0.91); 2.676 (0.65); 2.6715 (0.81); 2.667 (0.59); 2.5415 (1.24); 2.5246 (3.49); 2.5113 (47.16); 2.507 (88.52); 2.5025 (115.82); 2.4981 (80.76); 2.4937 (38.83); 2.3339 (0.6); 2.3291 (0.78); 2.3245 (0.57); 2.1301 (1.22); 2.0971 (2.53); 2.0688 (1.68); 2.0381 (0.44); 1.9873 (6.06); 1.8376 (0.53); 1.817 (1.07); 1.8084 (1.14); 1.7853 (1.06); 1.7774 (1.02); 1.7566 (0.44); 1.6124 (0.49); 1.6027 (0.57); 1.5815 (1.08); 1.573 (1.18); 1.5512 (1.13); 1.5423 (1.05); 1.522 (0.49); 1.2365 (3.92); 1.1933 (1.69); 1.1755 (3.37); 1.1657 (1.98); 1.1577 (1.87); 0.8542 (0.44); −0.0002 (3.1)

Ex. I-39, Solvent: DMSO-$d_6$ 8.7771 (2.11); 8.0267 (0.4); 8.0235 (0.36); 8.006 (16); 7.9817 (1.67); 7.5997 (0.93); 7.3469 (1.88); 7.3426 (2.19); 7.3238 (9.44); 7.3048 (11.46); 7.171 (7.57); 7.1571 (4.87); 7.1515 (4.97); 7.1318 (3.93); 7.0377 (3.99); 7.0213 (11.21); 7.0032 (4.63); 6.9848 (2.64); 6.9642 (0.53); 6.8979 (7.65); 6.8855 (4.6); 5.8875 (2.21); 5.8695 (2.62); 5.8598 (2.63); 5.8418 (2.35); 5.7464 (6.68); 5.4479 (1.38); 5.4053 (5.11); 5.3641 (5.49); 5.3214 (1.43); 4.8769 (12.77); 4.871 (12.92); 4.7991 (1.38); 4.3569 (1.65); 4.3255 (1.77); 4.1206 (0.91); 4.1143 (0.93); 4.039 (0.77); 4.0213 (0.89); 4.0032 (0.45); 3.9751 (1.7); 3.946 (1.94); 3.919 (0.49); 3.8967 (2.45); 3.8688 (2.85); 3.8537 (3.11); 3.8259 (2.56); 3.5666 (3.33); 3.5607 (7.23); 3.5548 (3.28); 3.4323 (0.43); 3.4124 (1.05); 3.4032 (1.62); 3.3932 (1.55); 3.3835 (2.24); 3.3747 (3.41); 3.365 (3.02); 3.3084 (1959.21); 3.2859 (20.62); 3.2716 (9.69); 3.2536 (7.04); 3.2286 (5.39); 3.2105 (4.11); 3.155 (0.95); 3.1487 (1.16); 3.1424 (0.94); 3.1116 (0.56); 3.0552 (0.43); 3.0369 (0.75); 2.9398 (0.48); 2.9243 (0.36); 2.9089 (0.36); 2.8899 (0.59); 2.8646 (1.51); 2.8491 (1.15); 2.8376 (2.33); 2.8047 (1.39); 2.7322 (0.36); 2.695 (0.48); 2.6737 (1.99); 2.6692 (5.8); 2.5654 (0.83); 2.5394 (4.15); 2.5224 (9.75); 2.5091 (122.25); 2.5047 (229.43); 2.5002 (302.8); 2.4958 (216.89); 2.4914 (108.87); 2.4039 (0.74); 2.3316 (1.84); 2.327 (2.36); 2.3225 (1.8); 2.2882 (0.41); 2.2805 (0.44); 2.2698 (0.37); 2.2532 (0.4); 2.2371 (0.36); 2.2001 (0.39); 2.1792 (0.43); 2.1286 (1.81); 2.0942 (3.42); 2.0691 (3.06); 2.0221 (0.37); 2.0091 (0.41); 1.9867 (3.55); 1.9078 (0.34); 1.8345 (0.85); 1.8054 (1.56); 1.7828 (1.53); 1.7525 (0.72); 1.6103 (0.74); 1.5994 (0.81); 1.5803 (1.56); 1.5702 (1.54); 1.5491 (1.56); 1.5415 (1.36); 1.5207 (0.71); 1.4701 (1.14); 1.4062 (2.26); 1.3982 (0.81); 1.3522 (0.8); 1.337 (0.35); 1.2983 (1.38); 1.2844 (0.38); 1.259 (2.18); 1.2363 (3.16); 1.1927 (1.18); 1.1749 (2.11); 1.1571 (1.17); 0.8706 (0.35); 0.8542 (0.53); 0.8374 (0.36); 0.0079 (1.18); −0.0002 (23.73); −0.0084 (1.06)

Ex. I-40, Solvent: DMSO-$d_6$ 9.7795 (2.15); 8.0164 (4.15); 7.3719 (1.96); 7.3505 (2.62); 7.3073 (0.7); 7.2321 (2.84); 7.2106 (2.14); 7.1739 (1.6); 7.159 (0.81); 7.0407 (0.8); 7.023 (1.82); 6.8997 (1.61); 6.8871 (0.92); 5.7081 (0.57); 5.687 (0.73); 5.6815 (0.7); 5.6602 (0.59); 5.4515 (0.34); 5.4089 (1.22); 5.3673 (1.2); 4.3633 (0.38); 4.3298 (0.4); 4.0569 (1.23); 4.0391 (3.66); 4.0213 (3.7); 4.0035 (1.32); 3.9825 (0.39); 3.9505 (0.41); 3.8743 (0.6); 3.8471 (0.69); 3.8313 (0.79); 3.8043 (0.67); 3.5676 (0.45); 3.4145 (0.47); 3.387 (1.51); 3.3765 (0.78); 3.3661 (1.4); 3.3576 (1.06); 3.344 (1.94); 3.3089 (349.24); 3.242 (0.49); 2.9856 (11.18); 2.8443 (0.49); 2.674 (0.35); 2.6693 (0.43); 2.6647 (0.34); 2.5393 (0.77); 2.5223 (2.25); 2.509 (25.66); 2.5047 (46.92); 2.5003 (60.77); 2.4959 (42.78); 2.4915 (20.9); 2.3316 (0.33); 2.327 (0.43); 2.1462 (0.33); 2.1378 (0.36); 2.1018 (0.72); 2.0692 (0.49); 1.9867 (16); 1.8234 (0.32); 1.8106 (0.33); 1.5813 (0.33); 1.1927 (4.46); 1.1749 (8.83); 1.1571 (4.3); 0.0079 (0.33); −0.0002 (6.07)

Ex. I-41, Solvent: DMSO-$d_6$ 8.7994 (0.47); 8.4174 (0.9); 8.2839 (0.36); 8.2697 (0.35); 8.0449 (0.54); 8.0402 (10.68); 7.2726 (1.64); 7.2052 (0.34); 7.1838 (3.6); 7.1299 (1.86); 7.1248 (0.46); 7.0951 (1.84); 7.0875 (2.13); 7.0852 (2.25); 7.0747 (2.17); 7.0724 (2.24); 7.0499 (0.42); 7.0393 (4.58); 7.0249 (1.31); 7.0223 (1.23); 7.0116 (2.05); 7.0103 (1.98); 6.9995 (1.42); 6.9969 (1.33); 6.9488 (2.1); 6.9259 (0.47); 6.9138 (4.9); 6.6961 (2.67); 6.6945 (2.7); 6.6828 (2.55); 6.6811 (2.46); 6.5725 (1.38); 6.5709 (1.35); 6.5601 (2.51); 6.5586 (2.39); 6.5478 (1.31); 6.5461 (1.24); 5.7809 (1.45); 5.7643 (16); 5.7492 (1.47); 5.4542 (1.24); 5.4257 (2.63); 5.4082 (0.39); 5.3775 (3.26); 5.349 (1.46); 5.0277 (5.17); 4.357 (0.98); 4.3351 (1.06); 3.9735 (0.97); 3.9504 (1.06); 3.8413 (1.49); 3.8232 (1.73); 3.8129 (1.83); 3.7948 (1.55); 3.4055 (0.41); 3.3991 (0.75); 3.3928 (0.53); 3.3862 (0.85); 3.3799 (1.46); 3.3737 (0.93); 3.3672 (0.66); 3.3607 (0.98); 3.3462 (82.73); 3.3226 (1.35); 3.2793 (0.79); 3.2593 (1.37); 3.2524 (2.16); 3.2375 (2.58); 3.23 (0.42); 3.2239 (1.86); 3.2091 (1.7); 3.1955 (1.72); 2.8489 (0.87); 2.8292 (1.24); 2.8103 (0.71); 2.6183 (0.45); 2.6153 (0.62); 2.6122 (0.45); 2.565 (0.84); 2.5427 (0.34); 2.5243 (1.2); 2.5212 (1.52); 2.5181 (1.48); 2.5093 (32.91); 2.5063 (73.12); 2.5032 (101.55); 2.5002 (73.05); 2.4972 (32.78); 2.3902 (0.43); 2.3871 (0.59); 2.3841 (0.42); 2.1241 (0.84); 2.1025 (1.06); 2.1 (1.06); 2.0869 (1.05); 2.0652 (1.02); 1.8294 (0.37); 1.8156 (0.74); 1.8095 (0.84); 1.795 (0.81); 1.7891 (0.8); 1.7753 (0.41); 1.7681 (0.38); 1.766 (0.39); 1.5923 (0.32); 1.5855 (0.38); 1.5717 (0.78); 1.5654 (0.86); 1.5513 (0.86); 1.545 (0.85); 1.5314 (0.44); 1.5244 (0.39); 1.4077 (0.38); 1.3509 (0.49); 1.2987 (1.71); 1.258 (2.56); 1.234 (1.6); 0.8535 (0.36); −0.0001 (1.81)

-continued

Ex. I-42, Solvent: DMSO-d$_6$ 9.4493 (7.94); 8.7772 (0.82); 8.4303 (0.53); 8.0283 (0.8); 8.0179 (7.95); 7.308 (1.64); 7.2965 (0.35); 7.209 (0.44); 7.1937 (1.66); 7.1745 (6.63); 7.1597 (2.59); 7.1549 (2.47); 7.0415 (1.86); 7.0235 (4.22); 7.0145 (0.94); 6.9974 (0.37); 6.9001 (4.83); 6.8877 (2.35); 6.8786 (0.55); 6.7924 (2.09); 6.7697 (3.43); 6.7634 (3.24); 6.7228 (1.76); 6.721 (1.78); 6.7169 (1.49); 6.7027 (1.59); 6.7006 (1.53); 6.6969 (1.39); 5.6685 (1.23); 5.649 (1.52); 5.6413 (1.44); 5.622 (1.29); 5.5927 (0.65); 5.4513 (0.76); 5.409 (2.91); 5.3689 (3.36); 5.3259 (0.87); 4.3621 (0.97); 4.329 (1.06); 4.0571 (1.25); 4.0393 (3.76); 4.0216 (3.82); 4.0037 (1.47); 3.9832 (0.95); 3.9469 (1.09); 3.8812 (1.39); 3.8537 (1.5); 3.8382 (1.7); 3.8108 (1.45); 3.4222 (0.58); 3.4129 (0.84); 3.4038 (0.77); 3.3938 (1.08); 3.3846 (1.54); 3.3758 (1.09); 3.3643 (0.97); 3.3557 (1.28); 3.3355 (3.2); 3.3073 (237.48); 3.2837 (4.75); 3.2733 (3.42); 3.2409 (1.06); 2.874 (0.79); 2.8447 (1.37); 2.8145 (0.77); 2.6694 (0.4); 2.5656 (0.51); 2.5393 (0.89); 2.5087 (24.65); 2.5047 (42.64); 2.5003 (53.05); 2.4961 (36.83); 2.3314 (0.34); 2.3271 (0.4); 2.3225 (0.32); 2.1358 (1.03); 2.1026 (2.05); 2.069 (1.35); 1.9868 (16); 1.8419 (0.45); 1.823 (0.87); 1.8133 (0.91); 1.7906 (0.85); 1.7625 (0.39); 1.6224 (0.38); 1.6116 (0.45); 1.5906 (0.87); 1.5821 (0.91); 1.5603 (0.89); 1.5521 (0.84); 1.5307 (0.43); 1.3979 (0.61); 1.1928 (4.39); 1.175 (8.6); 1.1572 (4.23); −0.0002 (0.79)

Ex. I-43, Solvent: DMSO-d$_6$ 8.7778 (0.33); 8.0198 (5.88); 7.9699 (1.46); 7.967 (1.51); 7.9504 (1.6); 7.9475 (1.57); 7.668 (0.58); 7.6648 (0.6); 7.6487 (1.35); 7.6301 (1.08); 7.6269 (1.02); 7.573 (1.76); 7.5557 (1.09); 7.4867 (0.94); 7.4835 (0.88); 7.4677 (1.45); 7.465 (1.36); 7.4491 (0.72); 7.4458 (0.65); 7.3042 (1.08); 7.1709 (2.45); 7.1579 (1.29); 7.0377 (1.24); 7.0219 (2.86); 6.8984 (2.52); 6.8861 (1.46); 6.3307 (0.91); 6.3144 (1.04); 6.3028 (1.02); 6.2866 (0.9); 5.7471 (1.24); 5.4458 (0.47); 5.403 (1.82); 5.3634 (1.83); 5.3207 (0.47); 4.3556 (0.57); 4.3222 (0.64); 4.066 (1.02); 4.0384 (1.29); 4.022 (1.63); 3.9941 (1.12); 3.9744 (0.58); 3.9402 (0.65); 3.896 (0.51); 3.882 (16); 3.8764 (2.11); 3.4031 (0.42); 3.3947 (0.62); 3.3847 (0.54); 3.3754 (0.76); 3.3659 (1.16); 3.3561 (0.96); 3.3096 (206.94); 3.2574 (0.88); 3.2373 (1.34); 3.2211 (1.51); 3.1932 (1.1); 3.1771 (1.05); 2.8592 (0.39); 2.8301 (0.71); 2.8006 (0.42); 2.5099 (10.14); 2.5056 (18.43); 2.5011 (23.66); 2.4968 (16.39); 2.4925 (7.85); 2.1203 (0.51); 2.0857 (1.04); 2.0701 (0.82); 2.0479 (0.61); 1.9873 (1.86); 1.8084 (0.45); 1.7991 (0.46); 1.7779 (0.45); 1.7692 (0.4); 1.573 (0.44); 1.5639 (0.48); 1.5416 (0.45); 1.5338 (0.43); 1.3978 (0.45); 1.1931 (0.5); 1.1754 (0.99); 1.1576 (0.49); −0.0002 (0.69)

Ex. I-44, Solvent: DMSO-d$_6$ 8.0475 (5.06); 7.495 (1.24); 7.4826 (1.6); 7.4102 (1.83); 7.4041 (3.54); 7.3971 (0.34); 7.3692 (0.83); 7.3634 (0.77); 7.3604 (0.54); 7.3566 (0.75); 7.3501 (0.61); 7.342 (0.43); 7.2712 (0.78); 7.1826 (1.81); 7.1267 (0.87); 7.094 (0.87); 7.0363 (2.12); 6.9459 (0.98); 6.9113 (2.22); 6.1015 (0.88); 6.0881 (1); 6.083 (0.96); 6.0696 (0.87); 5.7625 (0.41); 5.453 (0.7); 5.4246 (1.58); 5.3741 (1.55); 5.3457 (0.71); 4.9788 (1.52); 4.9595 (2.11); 4.8775 (2.19); 4.8582 (1.56); 4.3593 (0.5); 4.3374 (0.52); 4.024 (0.84); 4.0055 (0.96); 3.9953 (1.04); 3.9768 (1.33); 3.9536 (0.52); 3.5692 (16); 3.405 (0.43); 3.3921 (0.47); 3.386 (0.78); 3.3797 (0.47); 3.3665 (0.43); 3.3179 (0.96); 3.3045 (0.96); 3.2891 (1.01); 3.2846 (0.4); 3.2758 (1.06); 3.2601 (0.69); 3.2413 (0.38); 2.9439 (4.47); 2.8484 (0.35); 2.8279 (0.64); 2.8105 (0.35); 2.7838 (3.59); 2.6147 (0.39); 2.5647 (2.32); 2.524 (0.48); 2.5209 (0.66); 2.5178 (0.79); 2.5088 (22.38); 2.506 (47.3); 2.503 (64.84); 2.5 (47.32); 2.4972 (22.18); 2.3872 (0.4); 2.1253 (0.44); 2.1059 (0.53); 2.0882 (0.49); 2.0771 (0.56); 2.0671 (0.48); 1.958 (3.87); 1.9096 (0.52); 1.8112 (0.39); 1.8049 (0.43); 1.7908 (0.41); 1.7849 (0.38); 1.5726 (0.4); 1.5662 (0.42); 1.5519 (0.43); 1.5458 (0.4); −0.0002 (7.43)

Ex. I-45, Solvent: DMSO-d$_6$ 9.8994 (0.63); 8.6648 (0.61); 8.0229 (16); 7.4357 (1.96); 7.4324 (2.4); 7.4236 (1.91); 7.4213 (2.43); 7.3478 (1.87); 7.3445 (1.38); 7.3368 (3.12); 7.3327 (3.24); 7.3236 (0.36); 7.3188 (0.75); 7.3155 (1.2); 7.3066 (3.51); 7.3034 (2.83); 7.2992 (3.06); 7.2958 (5.35); 7.2914 (2.5); 7.2872 (2.31); 7.2844 (1.96); 7.2752 (0.76); 7.272 (0.84); 7.2686 (1.88); 7.18 (4.51); 7.1262 (2.14); 7.0915 (2.15); 7.0358 (5.68); 6.9455 (2.53); 6.9112 (4.84); 5.9981 (1.98); 5.985 (2.2); 5.9797 (2.14); 5.9666 (1.95); 5.4504 (1.65); 5.422 (3.66); 5.3725 (3.49); 5.3442 (1.59); 5.2615 (2.95); 5.2525 (6.4); 5.2434 (3.09); 4.5916 (5.58); 4.5828 (6.19); 4.3573 (1.04); 4.3356 (1.09); 4.0458 (0.36); 4.0339 (1.18); 4.022 (1.16); 4.0102 (0.41); 3.9728 (1.02); 3.9502 (1.11); 3.9242 (2.07); 3.9057 (2.46); 3.8955 (2.62); 3.8774 (1.44); 3.8408 (0.53); 3.399 (0.98); 3.3921 (0.76); 3.3858 (1.32); 3.3796 (2.18); 3.3733 (1.71); 3.3708 (1.53); 3.3455 (1366.81); 3.3281 (1.18); 3.3219 (7.12); 3.2787 (0.87); 3.2676 (2.65); 3.2545 (3.25); 3.2389 (3.08); 3.2259 (2.39); 2.8468 0.77); 2.8292 (1.33); 2.8093 (0.77); 2.6345 (0.44); 2.6205 (0.48); 2.6175 (1.06); 2.6144 (1.48); 2.6114 (1.06); 2.6083 (0.44); 2.564.5 (7.75); 2.5421 (0.9); 2.5237 (2.39); 2.5207 (3.2); 2.5175 (3.58); 2.5088 (77.52); 2.5057 (170.79); 2.5027 (231.96); 2.4996 (165.03); 2.4966 (71.78); 2.3929 (0.47); 2.3899 (1.05); 2.3869 (1.45); 2.3838 (1.01); 2.3806 (0.47); 2.2874 (0.42); 2.1221 (0.94); 2.1026 (1.13); 2.0865 (1.06); 2.0767 (2.1); 2.0628 (1.01); 1.9898 (5.36); 1.9087 (0.57); 1.8306 (0.39); 1.8242 (0.4); 1.811 (0.84); 1.8039 (0.89); 1.7902 (0.88); 1.7837 (0.81); 1.7698 (0.36); 1.5906 (0.36); 1.5839 (0.47); 1.5703 (0.89); 1.5637 (1.01); 1.5495 (0.96); 1.5436 (0.89); 1.5297 (0.41); 1.397 (2.51); 1.3003 (0.45); 1.2339 (0.42); 1.186 (1.58); 1.1742 (3.29); 1.1623 (1.47); −0.0002 (4.77)

Ex. I-46, Solvent: DMSO-d$_6$ 8.0198 (0.55); 7.9687 (1.48); 7.9658 (1.51); 7.9492 (1.63); 7.9462 (1.59); 7.6807 (0.58); 7.6774 (0.6); 7.6615 (1.34); 7.6427 (1.06); 7.6394 (0.96); 7.5663 (1.7); 7.5478 (1.16); 7.4963 (0.94); 7.4933 (0.87); 7.4773 (1.47); 7.4746 (1.37); 7.4586 (0.74); 7.4555 (0.65); 7.2868 (1.01); 7.1535 (2.44); 7.1487 (1.38); 7.0205 (1.47); 7.0125 (2.57); 6.8914 (2.33); 6.8765 (1.25); 6.3284 (0.9); 6.3115 (1.04); 6.3002 (1.01); 6.2834 (0.89); 5.7472 (1.05); 5.4238 (0.46); 5.3815 (1.75); 5.3629 (0.38); 5.3439 (1.73); 5.3017 (0.44); 4.3222 (0.6); 4.2884 (0.56); 4.1332 (0.95); 4.1048 (1.14); 4.0886 (1.26); 4.0603 (1.09); 4.0395 (0.55); 4.0216 (0.6); 3.946 (0.59); 3.9122 (0.64); 3.8815 (2.97); 3.8756 (16); 3.364 (0.67); 3.3066 (262.77); 3.2665 (1.62); 3.2497 (1.65); 3.2364 (0.45); 3.2219 (1.75); 3.2053 (1.2); 3.1923 (0.49); 2.8275 (0.43); 2.7989 (0.68); 2.7687 (0.36); 2.5396 (0.5); 2.5094 (17.55); 2.5052 (31.81); 2.5007 (40.84); 2.4963 (28.27); 2.492 (13.58); 2.0699 (0.96); 2.0428 (1.01); 2.0081 (0.55); 1.9871 (2.09); 1.7583 (0.42); 1.7513 (0.45); 1.726 (0.4); 1.5359 (0.46); 1.5279 (0.46); 1.5054 (0.43); 1.4963 (0.38); 1.398 (0.61); 1.1971 (0.4); 1.1931 (0.61); 1.1789 (0.84); 1.1753 (1.24); 1.1575 (0.61); −0.0002 (1.5)

Ex. I-47, Solvent: DMSO-d$_6$ 8.0201 (8.85); 7.3382 (4.89); 7.3163 (5.8); 7.1785 (3.4); 7.1663 (1.65); 7.0454 (1.74); 7.0304 (3.94); 6.997 (0.61); 6.99 (6.2); 6.9849 (1.95); 6.9681 (5.65); 6.9068 (3.57); 6.8946 (1.86); 5.6895 (1.29); 5.6676 (1.57); 5.6625 (1.56); 5.6404 (1.34); 5.4585 (0.77); 5.4161 (2.59); 5.3737 (2.58); 5.3312 (0.82); 4.7544 (3.69); 4.7492 (7.22); 4.7439 (3.96); 4.3653 (0.77); 4.333 (0.82); 3.9834 (0.7); 3.9527 (0.77); 3.85 (1.3); 3.8228 (1.57); 3.8068 (1.82); 3.78 (1.47); 3.4279 (0.53); 3.416 (0.87); 3.3975 (0.94); 3.3891 (2.92); 3.3789 (1.33); 3.3676 (2.99); 3.3445 (134.57); 3.3385 (175); 3.3322 (300.5); 3.3307 (334.71); 3.2696 (1.14); 3.2393 (0.64); 2.8687 (0.53); 2.8378 (0.96); 2.8109 (0.55); 2.6752 (0.67); 2.6705 (0.79); 2.6661 (0.62); 2.5411 (0.49); 2.5243 (1.49); 2.506 (90.88); 2.5019 (122.12); 2.3333 (0.65); 2.3287 (0.84); 2.2509 (0.5); 2.2454 (1.08); 2.2402 (0.63); 2.2319 (1.53); 2.2267 (3.22); 2.2215 (1.51); 2.2133 (1.6); 2.2081 (1.58); 2.2028 (1.58); 2.1945 (0.68); 2.1893 (1.18); 2.1843 (0.56); 2.1395 (0.65); 2.1052 (1.39); 2.073 (2.87); 1.9885 (0.63); 1.8206 (0.61); 1.8124 (0.65); 1.7915 (0.6); 1.7816 (1.59); 1.589 (0.61); 1.5782 (0.73); 1.5562 (0.62); 1.5494 (0.63); 1.2354 (0.59); 1.1745 (0.37); 1.0686 (7.63); 1.05 (16); 1.0312 (7.23); −0.0002 (6.53)

Ex. I-48, Solvent: DMSO-d$_6$ 16.1708 (0.4); 14.1949 (0.4); 8.0206 (11.08); 7.338 (5.82); 7.3163 (6.87); 7.179 (4.05); 7.1667 (2.13); 7.0617 (0.39); 7.0457 (2.11); 7.0308 (4.58); 6.9876 (7.25); 6.9657 (6.39); 6.9072 (4.18); 6.8949 (2.24); 5.689 (1.51); 5.6685 (1.95); 5.6626 (1.9); 5.6414 (1.54); 5.4595 (1.02); 5.4162 (3.18); 5.3737 (3.01); 5.332 (0.97); 4.7412 (6.34); 4.7355 (6.31); 4.3661 (1.06); 4.3351 (1.05); 3.9863 (1.05); 3.9515 (1.06); 3.8497 (1.47); 3.823 (1.89); 3.8067 (2.08); 3.7799 (1.76); 3.7105 (0.49); 3.5114 (0.41); 3.4946 (0.43); 3.4615 (0.44); 3.4534 (0.43); 3.4442 (0.43); 3.4258 (0.72); 3.4162 (1.25); 3.3984 (1.64); 3.3899 (3.87); 3.3679 (4.4); 3.3449 (249.75); 3.3367 (240.68); 3.3323 (386.08); 3.3309 (361.35); 3.27 (1.58); 3.2389 (0.98); 3.2014 (0.41); 2.8672 (0.79); 2.8447 (1.24); 2.8112 (0.76); 2.6749 (0.79); 2.6706 (1.02); 2.5411 (0.71); 2.502 (150.05); 2.4522 (0.46); 2.3283 (1.08);

-continued 2.1327 (0.91); 2.1207 (0.73); 2.1032 (1.79); 2.0824 (0.86); 2.0731 (5.8); 1.8308 (7.32); 1.825 (16); 1.8192 (7.93); 1.7909 (0.87); 1.7561 (0.44); 1.6181 (0.52); 1.6114 (0.44); 1.5873 (0.95); 1.5788 (0.88); 1.5577 (0.82); 1.5486 (0.91); 1.5296 (0.4); 1.3503 (0.49); 1.235 (1.1); −0.0002 (10.3); −0.0086 (0.6)
Ex. I-49, Solvent: DMSO-$d_6$ 11.229 (0.54); 7.966 (16); 7.4173 (2.95); 7.3966 (4.92); 7.3761 (4.16); 7.3179 (2.23); 7.1847 (5.22); 7.1669 (4.74); 7.1615 (5.88); 7.1453 (3.62); 7.1416 (4.91); 7.0517 (2.56); 7.0355 (6.07); 6.915 (4.71); 6.8997 (2.8); 6.2406 (2.1); 6.2163 (2.68); 6.2101 (2.45); 6.1853 (2.05); 5.7564 (15.94); 5.465 (1.16); 5.4225 (3.63); 5.3806 (3.49); 5.3384 (1.02); 4.8414 (0.53); 4.8327 (0.44); 4.8008 (4.39); 4.7923 (5.49); 4.7861 (4.32); 4.7524 (0.41); 4.7463 (0.7); 4.3743 (1.09); 4.3494 (0.99); 4.3439 (1.12); 4.3259 (0.33); 4.0615 (0.36); 4.0438 (0.77); 4.0262 (0.84); 3.9972 (1); 3.962 (1.2); 3.94 (0.32); 3.7713 (1.63); 3.7403 (1.93); 3.7292 (2.67); 3.6985 (2.21); 3.6491 (0.37); 3.6262 (0.36); 3.5878 (2.63); 3.5632 (2.64); 3.5457 (1.97); 3.5213 (1.92); 3.4969 (0.85); 3.4939 (0.8); 3.4682 (0.64); 3.4604 (0.9); 3.4441 (4.22); 3.4381 (8.78); 3.432 (4.65); 3.4194 (2.93); 3.4063 (5.77); 3.3984 (9.03); 3.3738 (6048.35); 3.3513 (14.05); 3.3368 (2.07); 3.3303 (1.971; 3.3266 (1.93); 3.3129 (2.2); 3.3005 (0.77); 3.2958 (0.91); 3.2834 (1.83); 3.2569 (0.7); 3.2521 (0.65); 3.2462 (0.81); 3.211 (0.37); 3.1698 (0.33); 3.0422 (0.5); 2.8868 (0.73); 2.8551 (1.62); 2.827 (0.71); 2.6837 (1.2); 2.6792 (1.71); 2.6745 (1.24); 2.5491 (0.92); 2.5323 (2.93); 2.5141 (178.87); 2.51 (245.29); 2.5065 (161.43); 2.3413 (1.23); 2.3367 (1.66); 2.3319 (1.19); 2.1629 (0.95); 2.1277 (1.77); 2.1053 (0.73); 2.0879 (1.15); 2.0777 (8.97); 2.064 (0.33); 1.9944 (3.02); 1.8555 (0.4); 1.8254 (0.94); 1.8012 (0.74); 1.7724 (0.36); 1.7665 (0.4); 1.6364 (0.44); 1.6299 (0.44); 1.6067 (0.88); 1.5972 (0.86); 1.5749 (0.87); 1.5455 (0.39); 1.5364 (0.32); 1.2404 (1.04); 1.1983 (0.95); 1.1806 (1.86); 1.1628 (0.91)
Ex. I-50, Solvent: DMSO-$d_6$ 7.9628 (8.19); 7.3715 (1.63); 7.3509 (3.36); 7.3303 (2.22); 7.3138 (1.26); 7.1805 (2.8); 7.1668 (1.22); 7.0973 (2.07); 7.0951 (2.69); 7.0771 (3.29); 7.0747 (2.48); 7.059 (1.6); 7.0475 (1.37); 7.0307 (3.32); 6.906 (2.65); 6.8947 (1.57); 6.2186 (1.65); 6.1935 (1.5); 6.188 (1.16); 6.1631 (1.07); 5.4691 (0.61); 5.4256 (1.83); 5.3719 (1.71); 5.3299 (0.68); 4.3718 (0.59); 4.3368 (0.61); 4.0802 (1.56); 4.0687 (2.85); 4.0561 (2.58); 4.0379 (3.55); 4.02 (3.62); 4.002 (1.46); 3.9563 (0.55); 3.7289 (0.61); 3.6982 (0.69); 3.6875 (1.65); 3.6572 (1.48); 3.6468 (1.72); 3.6219 (1.72); 3.6049 (0.64); 3.5803 (0.62); 3.4316 (0.52); 3.4211 (0.54); 3.4035 (2.04); 3.394 (2.91); 3.3859 (2.57); 3.3741 (1.78); 3.3248 (939.63); 3.3013 (2.75); 3.2753 (0.86); 3.2465 (0.57); 3.2427 (0.52); 2.8975 (14.63); 2.8755 (0.52); 2.845 (0.8); 2.818 (0.48); 2.6892 (0.51); 2.6752 (0.85); 2.6703 (1.23); 2.6658 (0.89); 2.661 (0.49); 2.5406 (0.8); 2.5238 (2.07); 2.519 (2.95); 2.5095 (70.63); 2.5056 (125.01); 2.5014 (171.49); 2.4977 (112.07); 2.3327 (0.87); 2.3282 (1.15); 2.3235 (0.88); 2.1441 (0.52); 2.1087 (0.94); 2.0734 (1.28); 1.9883 (16); 1.8217 (0.51); 1.7923 (0.51); 1.5881 (0.51); 1.5784 (0.49); 1.553 (0.47); 1.3982 (0.39); 1.2354 (0.63); 1.1922 (4.44); 1.1744 (8.98); 1.1566 (4.44); 0.008 (1.76); −0.0002 (62.49); −0.0085 (1.59)
Ex. I-51, Solvent: DMSO-$d_6$ 18.3412 (0.34); 16.7383 (0.35); 11.2347 (0.37); 7.9496 (16); 7.3773 (3.08); 7.3568 (6.3); 7.3362 (4.28); 7.316 (2.07); 7.1829 (5.12); 7.1688 (2.45); 7.1095 (3.66); 7.1073 (5.16); 7.0892 (7.26); 7.0871 (7.11); 7.0678 (3.07); 7.0497 (2.44); 7.0328 (6.11); 6.914 (4.66); 6.897 (2.75); 6.2663 (1.9); 6.2426 (2.59); 6.2352 (2.3); 6.2115 (2.14); 5.8335 (0.54); 5.8191 (1.11); 5.8067 (1.1); 5.7929 (1.49); 5.7761 (1.48); 5.7632 (1.26); 5.7525 (9.43); 5.7367 (0.81); 5.4692 (1.2); 5.4258 (3.44); 5.3759 (3.36); 5.3345 (1.1); 5.3208 (0.38); 5.2722 (2.98); 5.2681 (2.86); 5.2289 (2.45); 5.2249 (2.31); 5.2027 (0.33); 5.0209 (2.38); 5.0174 (2.36); 4.9948 (2.27); 4.991 (2.11); 4.5849 (0.71); 4.5724 (0.67); 4.5534 (2.13); 4.5398 (2.08); 4.5254 (2.05); 4.5114 (2.11); 4.4939 (0.74); 4.4799 (0.81); 4.3733 (1.01); 4.3187 (1.08); 4.0427 (0.45); 4.025 (0.51); 4.0042 (0.66); 3.9904 (0.91); 3.9604 (1.08); 3.7645 (1.44); 3.7334 (1.98); 3.7227 (2.79); 3.6918 (2.14); 3.6016 (0.34); 3.5818 (2.4); 3.5584 (2.31); 3.5402 (1.84); 3.5238 (0.68); 3.5166 (1.92); 3.4894 (0.61); 3.4847 (0.6); 3.4676 (0.7); 3.4573 (1.65); 3.451 (1.02); 3.4347 (2.84); 3.4252 (4.94); 3.4185 (6.74); 3.3951 (4801.39); 3.3751 (10.98); 3.3728 (10.61); 3.3624 (3.24); 3.3589 (3.53); 3.3523 (1.67); 3.3463 (1.79); 3.336 (1.28); 3.3269 (1.53); 3.3207 (1.35); 3.3148 (1.9); 3.3068 (0.92); 3.3036 (0.71); 3.2846 (1.77); 3.2573 (0.92); 3.2337 (0.34); 3.2137 (0.38); 3.1704 (0.36); 3.1667 (0.4); 2.8926 (0.66); 2.8576 (1.27); 2.8278 (0.72); 2.6837 (0.67); 2.6789 (0.93); 2.6745 (0.77); 2.5482 (0.41); 2.5324 (1.54); 2.5241 (95.3); 2.5099 (131.13); 2.5066 (86.18); 2.3416 (0.66); 2.3366 (0.9); 2.3277 (0.42); 2.1521 (0.97); 2.1182 (1.79); 2.0754 (6.83); 1.9929 (1.72); 1.8512 (0.48); 1.8218 (0.92); 1.8002 (0.9); 1.7666 (0.4); 1.6333 (0.5); 1.6214 (0.42); 1.6023 (0.87); 1.5911 (0.87); 1.5705 (0.88); 1.5304 (0.39); 1.2393 (0.73); 1.197 (0.5); 1.1792 (1.04); 1.1612 (0.48)
Ex. I-52, Solvent: $CD_3CN$ 7.7021 (16); 7.4902 (4.15); 7.4886 (4.26); 7.4772 (5.81); 7.4758 (5.79); 7.4465 (4.28); 7.4446 (4.55); 7.434 (5.64); 7.4321 (6.12); 7.4177 (2.57); 7.4156 (2.55); 7.4053 (5.48); 7.4031 (4.76); 7.3926 (3.16); 7.3904 (2.61); 7.3628 (4.04); 7.3606 (4.01); 7.3504 (5.48); 7.3481 (5.25); 7.3379 (2.08); 7.3357 (1.97); 6.9894 (4.29); 6.8994 (8.98); 6.878 (4.59); 6.8321 (8.64); 6.8094 (4.5); 6.7868 (9.78); 6.6957 (4.81); 6.0769 (3.71); 6.0626 (4.14); 6.0584 (4.1); 6.0441 (3.79); 5.2659 (2.73); 5.2377 (8.2); 5.203 (8.19); 5.1747 (2.82); 4.8399 (6.89); 4.8202 (10.83); 4.7567 (11.1); 4.737 (7.03); 4.4764 (1.97); 4.454 (2.03); 3.9819 (3.93); 3.9633 (4.06); 3.9533 (4.5); 3.9347 (4.24); 3.9091 (1.9); 3.8858 (2.04); 3.3625 (0.82); 3.3561 (1.71); 3.3489 (5.54); 3.3434 (2); 3.3347 (5.88); 3.3307 (2.11); 3.3239 (1.36); 3.3202 (4.98); 3.3112 (1.1); 3.306 (4.54); 3.2997 (1.62); 3.2952 (1.73); 3.279 (2.1); 3.2756 (2.78); 3.2563 (1.64); 3.2518 (1.47); 2.867 (1.34); 2.8265 (1.49); 2.8452 (2.48); 2.8418 (2.54); 2.8244 (1.52); 2.82 (1.41); 2.1905 (1.72); 2.1691 (18.57); 2.1374 (1.79); 2.1164 (1.9); 1.9653 (7.38); 1.9572 (0.58); 1.953 (0.79); 1.9493 (7.87); 1.9452 (14.91); 1.9411 (21.83); 1.937 (14.88); 1.9328 (7.49); 1.878 (0.74); 1.8711 (0.82); 1.8577 (1.71); 1.851 (1.8); 1.8366 (1.66); 1.8302 (1.68); 1.8166 (0.7); 1.8096 (0.61); 1.7099 (0.79); 1.7028 (0.88); 1.6896 (1.79); 1.6828 (1.87); 1.6685 (1.76); 1.6618 (1.7); 1.6485 (0.77); 1.6414 (0.69); −0.0001 (5.97)

The intensity of the sharp signals correlates to the height of the signals in a printed example of an NMR spectrum in cm, and shows the true ratios of the signal intensities. In the case of broad signals, several peaks or the middle of the signal and the relative intensity thereof may be shown in comparison to the most intense signal in the spectrum.

The lists of 1H NMR peaks are similar to the conventional 1H NMR printouts, and therefore usually contain all peaks listed in a conventional NMR interpretation.

In addition, like conventional 1H NMR printouts, they can show solvent signals, signals for stereoisomers of the target compounds, which likewise form part of the subject-matter of the invention, and/or peaks for impurities.

In the reporting of compound signals in the delta range of solvents and/or water, the usual solvent peaks are in our lists of 1H NMR peaks.

USE EXAMPLES

Example A

*Phytoplithora* Test (Tomato)/Protective
Solvent: 24.5 parts by weight of acetone
24.5 parts by weight of dimethylacetamide
Emulsifier: 1 part by weight of alkylaryl polyglycol ether To prepare an appropriate active ingredient preparation, 1 part by weight of active ingredient is mixed with the stated amounts of solvent and emulsifier, and the concentrate is diluted with water to the desired concentration.

To test for protective efficacy, young plants are sprayed with the active ingredient preparation at the stated application rate. After the spray coating has dried on, the plants are inoculated with an aqueous spore suspension of *Phytophthora infestans*. The plants are then placed in an incubation cabinet at approx. 20° C. and 100% relative air humidity.

Evaluation follows 3 days after the inoculation. 0% means an efficacy which corresponds to that of the control, whereas an efficacy of 100% means that no infection is observed.

In this test, the following inventive compounds exhibit an efficacy of 70% or more at an active ingredient concentration of 10 ppm: I-1 (95%), I-2 (99%), I-3 (100%), I-5 (93%), I-6 (94%), I-7 (97%), I-8 (97%), I-9 (96%), I-10 (97%), I-14 (98%), I-15 (95%), I-19 (96%), I-20 (95%), I-21 (98%), I-22 (98%), I-23 (97%), I-25 (95%), I-26 (97%), I-35 (88%), I-39 (99%), I-40 (95%), I-41 (94%), I-42 (94%).

Example B

*Plasmopara* Test (Grapevine)/Protective
Solvent: 24.5 parts by weight of acetone
24.5 parts by weight of dimethylacetamide
Emulsifier: 1 part by weight of alkylaryl polyglycol ether To prepare an appropriate active ingredient preparation, 1 part by weight of active ingredient is mixed with the stated amounts of solvent and emulsifier, and the concentrate is diluted with water to the desired concentration.

To test for protective efficacy, young plants are sprayed with the active ingredient preparation at the stated application rate. After the spray coating has dried on, the plants are inoculated with an aqueous spore suspension of *Plasmopara viticola* and then remain in an incubation cabinet at about 20° C. and 100% relative atmospheric humidity for 1 day. The plants are then placed in a greenhouse at approx. 21° C. and approx. 90% air humidity for 4 days. The plants are then moistened and placed in an incubation cabinet for 1 day.

Evaluation follows 6 days after the inoculation. 0% means an efficacy which corresponds to that of the control, whereas an efficacy of 100% means that no infection is observed.

In this test, the following inventive compounds exhibit an efficacy of 70% or more at an active ingredient concentration of 10 ppm: I-1 (100%), I-2 (100%), I-3 (100%), I-4 (100%), I-5 (97%), I-6 (100%), I-7 (100%), I-8 (99%), I-9 (99%), I-10 (100%), I-14 (100%), I-15 (93%), I-19 (96%), I-20 (98%), I-21 (100%), I-22 (97%), I-23 (99%), I-25 (74%), I-26 (100%), I-39 (99%), I-40 (91%), I-41 (100%), I-42 (97%).

Example C

*Peronospora* Test (Rapeseed)/Seed Treatment
The test was carried out under greenhouse conditions.

To produce an active ingredient preparation, the active ingredient was dissolved in N-methyl-2-pyrrolidone and the concentrate was diluted with water to the desired concentration. The rapeseeds treated with this solution were sown in 6*6 cm pots which had been filled to a height of 4 cm with a 1:1 mixture of steam-treated soil and sand. Then the plants were cultivated at 10° C.

After 14 days, the plants were inoculated with an aqueous spore suspension of *Peronospora brassicae*. Subsequently, the plants were placed in a greenhouse at approx. 15° C. and 100% air humidity for 7 days.

The evaluation was effected by assessing the infected leaf area per plant. 0% means an efficiency which corresponds to that of the control, while an efficiency or 100% means that no infestation is observed.

In this test, the following inventive compounds at an active ingredient concentration of 50 g/dt exhibited an efficiency of 80% or more: I-1 (100%), I-6 (100%), I-7 (100%).

The invention claimed is:
1. A compound of formula (I)

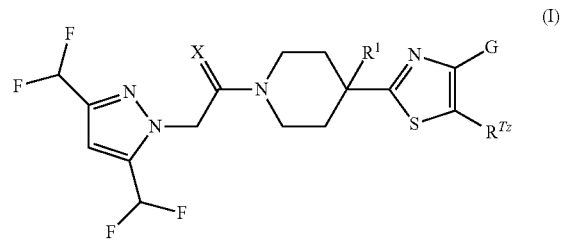

in which the symbols are each defined as follows:
X is oxygen or sulphur,

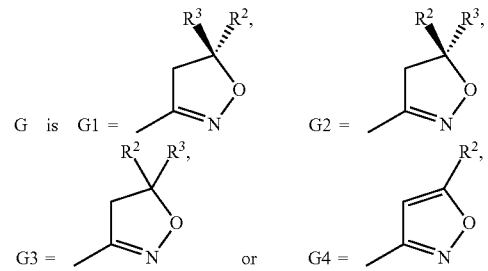

$R^1$ is hydrogen or halogen,
$R^2$ is a $C_3$-$C_8$-cycloalkyl which may contain up to two substituents, where the substituents are each independently selected from the group consisting of:
cyano, halogen, hydroxyl, oxo, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio and phenyl,
or
$R^2$ is a phenyl which may contain up to two substituents, where the substituents are each independently selected from the group consisting of: amino, halogen, cyano, hydroxyl, SH, nitro, C(=O)H, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_4$-$C_{10}$-alkyl-cycloalkyl, $C_4$-$C_{10}$-cycloalkylalkyl, $C_6$-$C_{14}$-cycloalkylcycloalkyl, $C_4$-$C_{10}$-halocycloalkylalkyl, $C_5$-$C_{10}$-alkylcycloalkylalkyl, $C_3$-$C_8$-cycloalkenyl, $C_3$-$C_8$-halocycloalkenyl, $C_2$-$C_6$-alkoxyalkyl, $C_4$-$C_{10}$-cycloalkoxyalkyl, $C_3$-$C_8$-alkoxyalkoxyalkyl, $C_2$-$C_6$-alkylthioalkyl, $C_2$-$C_6$-alkylsulphinylalkyl, $C_2$-$C_6$-alkylsulphonylalkyl, $C_2$-$C_6$-alkylaminoalkyl, $C_3$-$C_8$-dialkylaminoalkyl, $C_2$-$C_6$-haloalkylaminoalkyl, $C_4$-$C_{10}$-cycloalkylaminoalkyl, $C_2$-$C_6$-alkylcarbonyl, $C_2$-$C_6$-haloalkylcarbonyl, $C_4$-$C_8$-cycloalkylcarbonyl, $C_2$-$C_6$-alkoxycarbonyl, $C_4$-$C_8$-cycloalkoxycarbonyl, $C_5$-$C_{10}$-cycloalkylalkoxycarbonyl, $C_2$-$C_6$-alkylaminocarbonyl, $C_3$-$C_8$-dialkylaminocarbonyl, $C_4$-$C_8$-cycloalkylaminocarbonyl, $C_2$-$C_6$-haloalkoxyalkyl, $C_1$-$C_6$-hydroxyalkyl, $C_1$-$C_6$-alkoxy, $C_1$-$C_6$-haloalkoxy, $C_3$-$C_8$-cycloalkoxy, $C_3$-$C_8$-halocycloalkoxy, $C_4$-$C_{10}$-cycloalkylalkoxy, $C_2$-$C_6$-alkenyloxy, $C_2$-$C_6$-haloalkenyloxy, $C_2$-$C_6$-alkynyloxy, $C_2$-$C_6$-haloalkynyl-oxy, $C_2$-$C_6$-alkoxyalkoxy, $C_2$-$C_6$-alkylcarbonyloxy, $C_2$-$C_6$-haloalkyl-carbonyloxy, $C_4$-$C_8$-cycloalkylcarbonyloxy, $C_3$-$C_6$-alkylcarbonylalkoxy, $C_1$-$C_6$-alkylthio, $C_1$-$C_6$-haloalkylthio, $C_3$-$C_6$-cycloalkylthio, $C_1$-$C_6$-alkyl-sulphinyl, $C_1$-$C_6$-haloalkylsulphinyl, $C_1$-$C_6$-alkylsulphonyl, $C_1$-$C_6$-halo-alkylsulphonyl, $C_3$-$C_8$-cycloalkylsulphonyl, tri($C_1$-$C_4$-alkyl)silyl, $C_1$-$C_6$-alkylsulphonylamino, $C_1$-$C_6$-haloalkylsulphonylamino and -LQ, or $R^2$ is a 5- or 6-membered heteroaryl radical which may contain up to two substituents, where the substituents are each independently selected from the group consisting of:

substituents on carbon: halogen, cyano, nitro, hydroxyl, SH, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkyl-cycloalkyl, $C_4$-$C_{10}$-cycloalkylalkyl, $C_6$-$C_{14}$-cycloalkylcycloalkyl, $C_5$-$C_{10}$-alkylcycloalkylalkyl, $C_2$-$C_4$-alkoxyalkyl, $C_2$-$C_4$-alkylcarbonyl, $C_2$-$C_6$-alkoxycarbonyl, $C_2$-$C_6$-alkylaminocarbonyl, $C_3$-$C_8$-dialkylaminocarbonyl, $C_1$-$C_4$-hydroxyalkyl, $C_1$-$C_4$-alkoxy, $C_1$-$C_4$-haloalkoxy, $C_2$-$C_6$-alkyl-carbonyloxy, $C_2$-$C_6$-alkylcarbonylthio, $C_1$-$C_4$-alkylthio, $C_1$-$C_4$-halo-alkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, tri($C_1$-$C_4$-alkyl)silyl, and -LQ, substituents on nitrogen: $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_1$-$C_4$-alkylsulphonyl, C(=O)H, C(=O)Me, C(O)OMe, benzyl and phenyl, $R^3$ is hydrogen, cyano, $C_1$-$C_3$-alkyl or $C_1$-$C_3$-haloalkyl, $R^{Tz}$ is halogen or hydrogen L is a direct bond, —$CH_2$—, —(C=O)—, sulphur or oxygen, Q is a phenyl which may contain up to two substituents, where the substituents are each independently selected from the group consisting of:

halogen, cyano, nitro, hydroxyl, SH, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_2$-$C_6$-alkoxyalkyl, $C_2$-$C_6$-alkyl-carbonyl, $C_2$-$C_6$-haloalkylcarbonyl, $C_2$-$C_6$-alkoxycarbonyl, $C_1$-$C_6$-alkoxy, $C_1$-$C_6$-haloalkoxy, $C_3$-$C_8$-cycloalkoxy, $C_3$-$C_8$-halocycloalkoxy, $C_2$-$C_6$-alkenyloxy, $C_2$-$C_6$-alkynyloxy, $C_2$-$C_6$-alkoxyalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, tri($C_1$-$C_4$-alkyl)silyl and phenyl, or Q is a 5- or 6-membered heteroaryl radical which may contain up to two substituents, where the substituents are each independently selected from the group consisting of:

substituents on carbon: halogen, cyano, nitro, hydroxyl, SH, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkyl-cycloalkyl, $C_4$-$C_{10}$-cycloalkylalkyl, $C_6$-$C_{14}$-cycloalkylcycloalkyl, $C_5$-$C_{10}$-alkylcycloalkylalkyl, $C_2$-$C_4$-alkoxyalkyl, $C_2$-$C_4$-alkylcarbonyl, $C_2$-$C_6$-alkoxycarbonyl, $C_1$-$C_4$-alkoxy, $C_1$-$C_4$-haloalkoxy, $C_2$-$C_6$-alkylcarbonyl-oxy, $C_2$-$C_4$-alkylcarbonylthio, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, tri($C_1$-$C_4$-alkyl)silyl, and phenyl, substituents on nitrogen: $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_4$-haloalkynyl, $C_3$-$C_6$-cycloalkyl, $C_1$-$C_4$-alkylsulphonyl, C(=O)H, C(=O)Me, C(=O)OMe and phenyl, and agrochemically active salts, metal complexes and N-oxides thereof.

2. The compound of formula (I) according to claim 1, in which the symbols are each defined as follows:

X is oxygen, $R^1$ is hydrogen or fluorine,

G is G1, G3 or G4, $R^2$ is a $C_3$-$C_8$-cycloalkyl which may contain up to two substituents, where the substituents are each independently selected from the group consisting of:

cyano, halogen, hydroxyl, oxo, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio and phenyl, or $R^2$ is a phenyl which may contain up to two substituents, where the substituents are each independently selected from the group consisting of:

amino, halogen, cyano, hydroxyl, SH, nitro, C(=O)H, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_1$-$C_8$-cycloalkyl, $C_3$-$C_8$-halocycloalkyl, $C_4$-$C_{10}$-alkyl-cycloalkyl, $C_4$-$C_{10}$-cycloalkylalkyl, $C_6$-$C_{14}$-cycloalkylcycloalkyl, $C_4$-$C_{10}$-halocycloalkylalkyl, $C_5$-$C_{10}$-alkylcycloalkylalkyl, $C_3$-$C_8$-cycloalkenyl, $C_3$-$C_8$-halocycloalkenyl, $C_2$-$C_6$-alkoxyalkyl, $C_4$-$C_{10}$-cycloalkoxyalkyl, $C_3$-$C_8$-alkoxyalkoxyalkyl, $C_2$-$C_6$-alkylthioalkyl, $C_2$-$C_6$-alkylsulphinylalkyl, $C_2$-$C_6$-alkylsulphonylalkyl, $C_2$-$C_6$-alkylaminoalkyl, $C_3$-$C_8$-dialkyl-aminoalkyl, $C_2$-$C_6$-haloalkylaminoalkyl, $C_4$-$C_{10}$-cycloalkylaminoalkyl, $C_2$-$C_6$-alkylcarbonyl, $C_2$-$C_6$-haloalkylcarbonyl, $C_4$-$C_8$-cycloalkylcarbonyl, $C_2$-$C_6$-alkoxycarbonyl, $C_4$-$C_8$-cycloalkoxycarbonyl, $C_5$-$C_{10}$-cycloalkylalkoxycarbonyl, $C_2$-$C_6$-alkylaminocarbonyl, $C_3$-$C_8$-dialkylaminocarbonyl, $C_4$-$C_8$-cycloalkylaminocarbonyl, $C_2$-$C_6$-haloalkoxyalkyl, $C_1$-$C_6$-hydroxy-alkyl, $C_1$-$C_6$-alkoxy, $C_1$-$C_6$-haloalkoxy, $C_1$-$C_8$-cycloalkoxy, $C_3$-$C_8$-halo-cycloalkoxy, $C_4$-$C_{10}$-cycloalkylalkoxy, $C_2$-$C_6$-alkenyloxy, $C_2$-$C_6$-halo-alkenyloxy, $C_2$-$C_6$-alkynyloxy, $C_2$-$C_6$-haloalkynyloxy, $C_2$-$C_6$-alkoxyalkoxy, $C_2$-$C_6$-alkylcarbonyloxy, $C_2$-$C_6$-haloalkylcarbonyloxy, $C_4$-$C_8$-cyclo-alkylcarbonyloxy, $C_3$-$C_6$-alkylcarbonylalkoxy, $C_1$-$C_6$-alkylthio, $C_1$-$C_6$-haloalkylthio, $C_3$-$C_6$-cycloalkylthio, $C_1$-$C_6$-alkylsulphinyl, $C_1$-$C_6$-halo-alkylsulphinyl, $C_1$-$C_6$-alkylsulphonyl, $C_1$-$C_6$-haloalkylsulphonyl, $C_3$-$C_8$-cycloalkylsulphonyl, tri($C_1$-$C_4$-alkyl)silyl, $C_1$-$C_6$-alkylsulphonylamino, $C_1$-$C_6$-haloalkylsulphonylamino and -LQ, or $R^2$ is a 5- or 6-membered heteroaryl radical which may contain up to two substituents, where the substituents are each independently selected from the group consisting of:

substituents on carbon: halogen, cyano, nitro, hydroxyl, SH, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkyl-cycloalkyl, $C_4$-$C_{10}$-cycloalkylcycloalkyl, $C_6$-$C_{14}$-cycloalkylcycloalkyl, $C_5$-$C_{10}$-alkylcycloalkylalkyl, $C_2$-$C_4$-alkoxyalkyl, $C_2$-$C_4$-alkylcarbonyl, $C_2$-$C_6$-alkoxycarbonyl, $C_2$-$C_6$-alkylaminocarbonyl, $C_3$-$C_8$-dialkylaminocarbonyl, $C_1$-$C_4$-hydroxyalkyl, $C_1$-$C_4$-alkoxy, $C_1$-$C_4$-haloalkoxy, $C_2$-$C_6$-alkyl-carbonyloxy, $C_2$-$C_6$-alkylcarbonylthio, $C_1$-$C_4$-alkylthio, $C_1$-$C_4$-halo-alkylthio, $C_1$-$C_4$-alkylsulphinyl, $C_1$-$C_4$-haloalkylsulphinyl, $C_1$-$C_4$-alkyl-sulphonyl, $C_1$-$C_4$-haloalkylsulphonyl, tri($C_1$-$C_4$-alkyl)silyl, and -LQ, substituents on nitrogen: $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_1$-$C_4$-alkylsulphonyl, C(=O)H, C=O)Me, C(=O)OMe, benzyl and phenyl, $R^3$ is hydrogen, cyano or $C_1$-$C_3$-alkyl, L is a direct bond or oxygen, Q is a phenyl which may contain up to two substituents, where the substituents are each independently selected from the group consisting of:

halogen, cyano, hydroxyl, nitro, SH, $C_1$-$C_6$-alkyl, $C_1$-$C_6$-haloalkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-haloalkylthio and phenyl, or Q is a 5- or 6-membered heteroaryl radical which may contain up to two substituents, where the substituents are each independently selected from the group consisting of:

substituents on carbon: halogen, cyano, hydroxyl, nitro, SH, $C_1$-$C_6$-alkyl, $C_1$-$C_6$-haloalkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-haloalkylthio, and phenyl, substituents on nitrogen: $C_1$-$C_6$-alkyl, $C_2$-$C_6$-alkenyl, $C_2$-$C_6$-alkynyl, $C_3$-$C_6$-cycloalkyl and phenyl, and agrochemically active salts, metal complexes and N-oxides thereof.

3. The compound of formula (I) according to claim 1, in which the symbols are each defined as follows:

G is G3 or G4, and agrochemically active salts, metal complexes and N-oxides thereof.

4. The compound of formula (I) according to claim 1, in which the symbols are each defined as follows:

$R^2$ is a phenyl which may contain up to two substituents, where the substituents are each independently selected from the group consisting of:

amino, halogen, cyano, nitro, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_2$-$C_6$-alkoxyalkyl, $C_2$-$C_6$-alkylcarbonyl, $C_2$-$C_6$-haloalkylcarbonyl, $C_2$-$C_6$-alkoxycarbonyl, $C_1$-$C_6$-alkoxy, $C_1$-$C_6$-haloalkoxy, $C_3$-$C_8$-cycloalkoxy, $C_3$-$C_8$-halocycloalkoxy, $C_2$-$C_6$-alkenyloxy, $C_2$-$C_6$-alkynyloxy, $C_2$-$C_6$-alkoxyalkoxy, $C_1$-$C_6$-alkylthio, $C_1$-$C_6$-haloalkyl-thio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, and phenyl, and agrochemically active salts, metal complexes and N-oxides thereof.

5. The compound of formula (I) according to claim 4, in which $R^2$ is selected from the group consisting of phenyl, 2-fluorophenyl, 2,6-difluorophenyl, 2-acetylphenyl, 3-acetylphenyl, 2-hydroxyphenyl, 2-nitrophenyl, 2-[(2-methoxyethoxy)methyl]phenyl, 2-[(ethylsulphanyl)methyl]phenyl, 2-[(cyclopropylmethoxy)carbonyl]phenyl, 2-(allyloxy)-phenyl, 3-(but-2-yn-1-yloxy)phenyl, 2-(butoxymethyl)phenyl, 2-fluoro-6-formylphenyl, 2-[(2-methylprop-2-en-1-yl)oxy]phenyl, 2-(2-methoxy-ethoxy)phenyl, 2-[(3-methylbut-2-en-1-yl)oxy]phenyl, 3-(prop-2-yn-1-yloxy)phenyl, 4-(prop-2-yn-1-yloxy)phenyl, 3-formylphenyl, 2-(cyclohexylmethoxy)phenyl, 2-(pent-2-yn-1-yloxy)phenyl, 2-formyl-phenyl, 2-(cyclopropylcarbamoyl)phenyl, 2-(but-2-yn-1-yloxy)-6-fluorophenyl, 2-fluoro-6-(prop-2-yn-1-yloxy)phenyl, 2-[(cyclo-hexylcarbonyl)oxy]phenyl, 2-[(cyclopropylcarbonyl)oxy]phenyl, 3-(pent-2-yn-1-yloxy)phenyl, 2-(but-2-yn-1-yloxy)phenyl, 2-[(3,3,3-trifluoro-propanoyl)oxy]phenyl, 2-[(methylsulphonyl)amino]phenyl, 2-ethynyl-phenyl, 2-(prop-2-yn-1-yloxy)phenyl, 4-[(methylsulphonyl)amino]phenyl, 2-aminophenyl, 3-hydroxyphenyl, 2-(methoxycarbonyl)phenyl, 2-(chloromethyl)phenyl, 4-(pent-2-yn-1-yloxy)phenyl, 4-(but-2-yn-1-yloxy)phenyl, 2-chloro-6-(prop-2-yn-1-yloxy)phenyl, 2-chloro-6-(2-methoxyethoxy)phenyl, 2-(allyloxy)-6-chlorophenyl, 2-[(2,2,2-trifluoro-ethoxy)methyl]phenyl, 2-[(ethylsulphonyl)methyl]phenyl and 2-(hydroxymethyl)phenyl, and agrochemically active salts, metal complexes and N-oxides thereof.

6. The compound of formula (I) according to claim 1, in which $R^3$ is hydrogen, and agrochemically active salts, metal complexes and N-oxides thereof.

7. The compound of formula (I) according to claim 1, in which $R^{Tz}$ is hydrogen and agrochemically active salts, metal complexes and N-oxides thereof.

8. The compound of formula (I) according to claim 1, wherein G is G3, $R^2$ is a phenyl which may contain up to two substituents, where the substituents are each independently selected from the group consisting of:

amino, halogen, cyano, nitro, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_2$-$C_6$-alkoxyalkyl, $C_2$-$C_6$-alkylcarbonyl, $C_2$-$C_6$-haloalkyl-carbonyl, $C_2$-$C_6$-alkoxycarbonyl, $C_1$-$C_6$-alkoxy, $C_1$-$C_6$-haloalkoxy, $C_3$-$C_8$-cycloalkoxy, $C_3$-$C_8$-halocycloalkoxy, $C_2$-$C_6$-alkenyloxy, $C_2$-$C_6$-alkynyloxy, $C_2$-$C_6$-alkoxyalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, and phenyl, and agrochemically active salts, metal complexes and N-oxides thereof.

9. The compound of formula (I) according to claim 8, wherein $R^2$ is selected from the group consisting of phenyl, 2-fluorophenyl, 2,6-difluorophenyl, 2-acetylphenyl, 3-acetylphenyl, 2-hydroxyphenyl, 2-nitrophenyl, 2-[(2-methoxyethoxy)methyl]phenyl, 2-[(ethylsulphanyl)methyl]phenyl, 2-[(cyclopropylmethoxy)carbonyl]phenyl, 2-(allyloxy)phenyl, 3-(but-2-yn-1-yloxy)phenyl, 2-(butoxymethyl)phenyl, 2-fluoro-6-formylphenyl, 2-[(2-methylprop-2-en-1-yl)oxy]phenyl, 2-(2-methoxyethoxy)phenyl, 2-[(3-methylbut-2-en-1-yl)oxy]phenyl, 3-(prop-2-yn-1-yloxy)phenyl, 4-(prop-2-yn-1-yloxy)phenyl, 3-formylphenyl, 2-(cyclohexylmethoxy)phenyl, 2-(pent-2-yn-1-yloxy)phenyl, 2-formylphenyl, 2-(cyclopropylcarbamoyl)phenyl, 2-(but-2-yn-yloxy)-6-fluorophenyl, 2-fluoro-6-(prop-2-yn-1-yloxy)phenyl,

[(cyclohexylcarbonyl)oxy]phenyl, 2-[(cyclopropylcarbonyl)oxy]phenyl, 3-(pent-2-yn-1-yloxy)phenyl, 2-(but-2-yn-1-yloxy)phenyl, 2-[(3,3,3-trifluoropropanoyl)oxy]phenyl, 2-[(methylsulphonyl)amino]phenyl, 2-ethynylphenyl, 2-(prop-2-yn-1-yloxy)phenyl, 4-[(methylsulphonyl)amino]phenyl, 2-aminophenyl, 3-hydroxyphenyl, 2-(methoxycarbonyl)phenyl, 2-chlorophenyl, 2-(chloromethyl)phenyl, 4-(pent-2-yn-1-yloxy)phenyl, 4-(but-2-yn-1-yloxy)phenyl, 2-chloro-6-(prop-2-yn-1-yloxy)phenyl, 2-chloro-6-(2-methoxyethoxy)phenyl, 2-(allyloxy)-6-chlorophenyl, 2-[(2,2,2-trifluoroethoxy)methyl]phenyl, 2-[(ethylsulphonyl)methyl]phenyl and 2-(hydroxymethyl)phenyl,
and agrochemically active salts, metal complexes and N-oxides thereof.

10. The compound of formula (I) according to claim 9, wherein $R^3$ is hydrogen.

11. A composition for controlling phytopathogenic harmful fungi, said composition comprises at least one compound of formula (I) according to claim 1, in addition to extenders and/or surfactants.

12. A method for controlling phytopathogenic harmful fungi, said method comprises applying one or more compounds of formula (I) according to claim 1 to the phytopathogenic harmful fungi and/or their habitat.

13. A compound of formula (I)

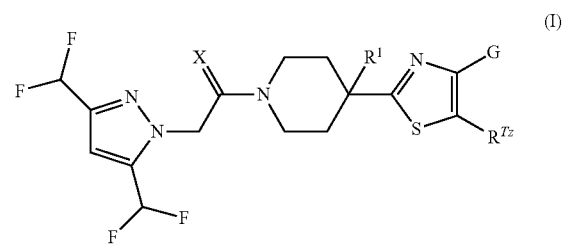

wherein X is oxygen, $R^1$ is hydrogen, G is G3, $R^2$ is 2-(prop-2-yn-1-yloxy)phenyl, $R^3$ is hydrogen, $R^{Tz}$ is hydrogen, and agrochemically active salts, metal complexes and N-oxides thereof.

14. A composition for controlling phytopathogenic harmful fungi, said composition comprises the compound of formula (I) according to claim 13, in addition to extenders and/or surfactants.

* * * * *